(12) United States Patent
Lu et al.

(10) Patent No.: US 12,054,714 B2
(45) Date of Patent: Aug. 6, 2024

(54) PEPTIDE DOCKING VEHICLE FOR TARGETED NUCLEIC ACID DELIVERY

(71) Applicant: Sirnaomics, Inc., Gatithersburg, MD (US)

(72) Inventors: Xiaoyong Lu, Gaithersburg, MD (US); Patrick Y. Lu, Gaithersburg, MD (US); David M. Evans, Gaithersburg, MD (US)

(73) Assignee: Sirnaomics, Inc., Germantown, MD (US)

( * ) Notice: Subject to any disclaimer, the term of this patent is extended or adjusted under 35 U.S.C. 154(b) by 290 days.

(21) Appl. No.: 17/114,443

(22) Filed: Dec. 7, 2020

(65) Prior Publication Data
US 2021/0214726 A1 Jul. 15, 2021

Related U.S. Application Data

(60) Provisional application No. 62/945,042, filed on Dec. 6, 2019.

(51) Int. Cl.
| | |
|---|---|
| C07K 7/08 | (2006.01) |
| A61K 47/64 | (2017.01) |
| C07K 7/06 | (2006.01) |
| C12N 15/113 | (2010.01) |
| C12N 15/117 | (2010.01) |

(52) U.S. Cl.
CPC ............ *C12N 15/113* (2013.01); *A61K 47/64* (2017.08); *C07K 7/08* (2013.01); *C12N 15/117* (2013.01); *C07K 7/06* (2013.01); *C12N 2310/11* (2013.01); *C12N 2310/127* (2013.01);
(Continued)

(58) Field of Classification Search
CPC .......... C12N 15/113; C12N 2310/3513; C12N 2310/16; C12N 2310/141; C12N 2310/13; C12N 2310/127; C12N 2310/11; C12N 15/117; C07K 7/06; C07K 7/08
See application file for complete search history.

(56) References Cited

U.S. PATENT DOCUMENTS

2011/0123520 A1 * 5/2011 Manoharan ........ A61K 48/0008
435/325

FOREIGN PATENT DOCUMENTS

| WO | WO-2017083368 A1 * | 5/2017 | ........... A61K 47/545 |
| WO | 2018/013525 A1 | 1/2018 | |

(Continued)

OTHER PUBLICATIONS

Guo et al. Oligomerized alpha-helical KALA peptides with pendant arms bearing cell adhesion, DNA-binding and endosome-buffering domains as efficient gene transfection vectors, Biomaterials 33 (2012) 6284e6291 (Year: 2012).*
(Continued)

*Primary Examiner* — Kevin S Orwig
*Assistant Examiner* — John Michael Cronin
(74) *Attorney, Agent, or Firm* — Edell, Shapiro & Finnan, LLC

(57) ABSTRACT

Peptide docking vehicle compositions containing a therapeutic compound, such as an siRNA molecule, and a targeting ligand are provided, together with methods for their preparation and use. The compositions and methods allow targeted cell/tissue delivery of the therapeutic compound to a subject by linking a targeting ligand to the compound to provide enhanced therapeutic benefit. The subject may be an animal or a human.

13 Claims, 16 Drawing Sheets

Specification includes a Sequence Listing.

Representative example of construction of the siRNA-PDoV-ligand compound 1 siRNA-PDoV-trivalent beta GalNAc₃

(52) U.S. Cl.
CPC .... *C12N 2310/13* (2013.01); *C12N 2310/141* (2013.01); *C12N 2310/16* (2013.01); *C12N 2310/3513* (2013.01)

(56) References Cited

FOREIGN PATENT DOCUMENTS

| WO | WO-2018075373 A1 * | 4/2018 | ........... A61K 31/713 |
| WO | 2019226940 A1 | 11/2019 | |

OTHER PUBLICATIONS

Winkler, J., "Oligonucleotide Conjugates for Therapeutic Applications", Ther. Deliv., vol. 4(7), pp. 791-809 (2013), on IDS. (Year: 2013).*

Farzan, V., et al. "Automated Solid-Phase Click Synthesis of Oligonucleotide Conjugates: From Small Molecules to Diverse N-Acetylgalactosamine Clusters", Bioconjugate Chemistry, vol. 28(10), pp. 2599-2607, 2017.

Supplementary Partial European Search Report in corresponding EP Application No. 20896972.5, Jan. 5, 2023, 13 pages.

Ma, L., et al., "Peptide-Drug Conjugate: A Novel Drug Design Approach", Current Medicinal Chemistry, vol. 24, pp. 1-24 (2017).

Winkler, J., "Oligonucleotide Conjugates for Therapeutic Applications", Ther. Deliv., vol. 4(7), pp. 791-809 (2013).

Yu, B., et al., "Targeted Delivery Systems for Oligonucleotide Therapeutics", The AAPS Journal, vol. 11(1), pp. 195-203 (2009).

Int'l Search Report and Written Opinion in corresponding International Patent Application No. PCT/US20/63676, mailed May 21, 2021.

* cited by examiner

Structure of the PDoV construct.

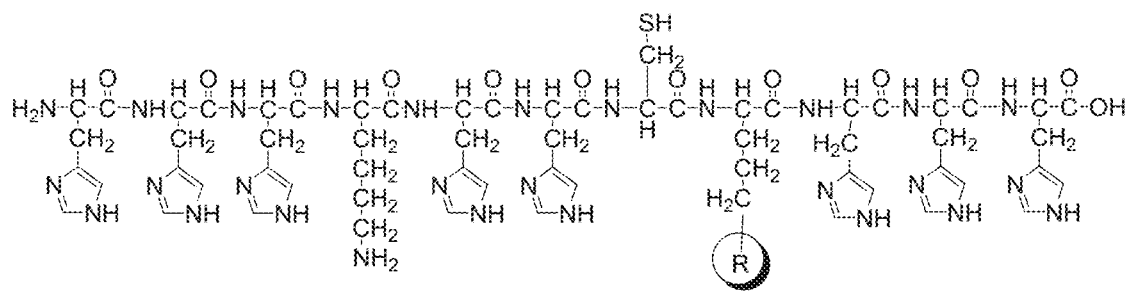
when R= CH₂NH₂ (PDoV1),
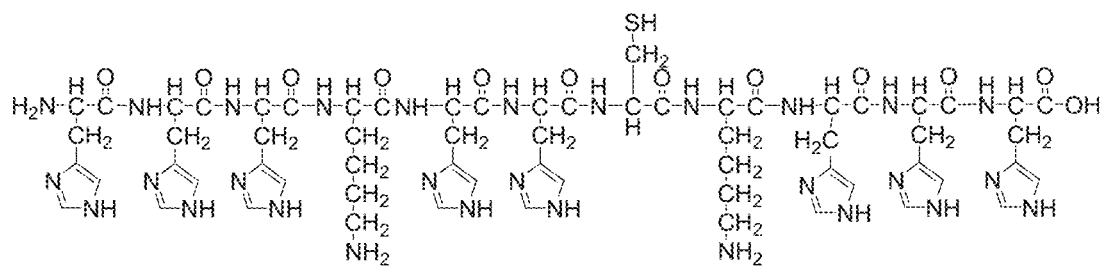
when R= NHC(NH₂)₂ (PDoV2);
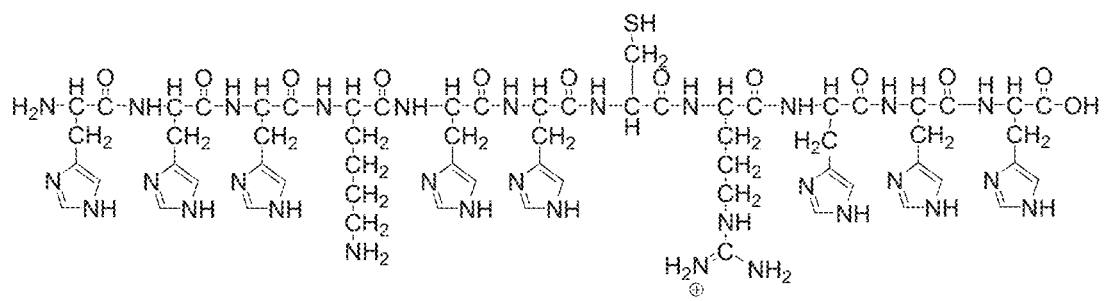
An example of a control peptide,
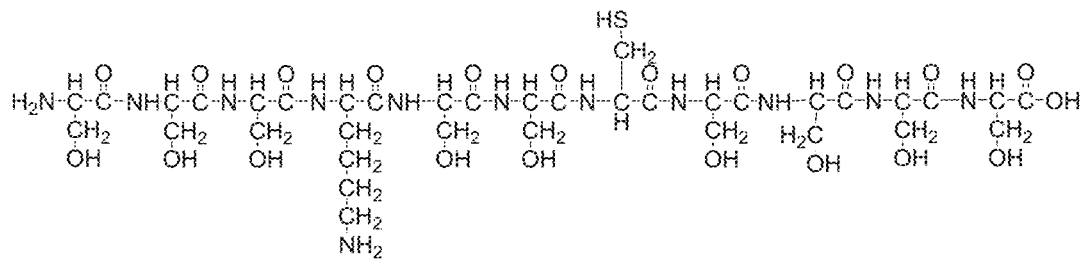
Where the peptide sequence is shorter:
Fig. 6

X-R_L = ligand conjugating site, such as SH, N3, maleimide etc.
X-R_S = siRNA, oligonucleotide conjugation site.

Linker 2 =
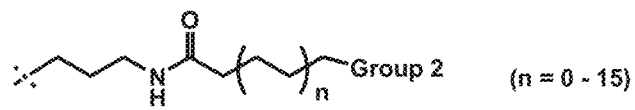 (n = 0 - 15)
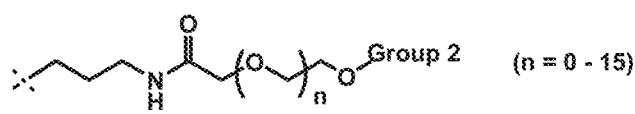 (n = 0 - 15)
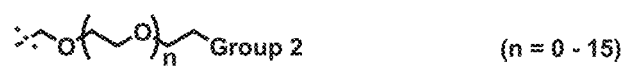 (n = 0 - 15)
Group 2 =
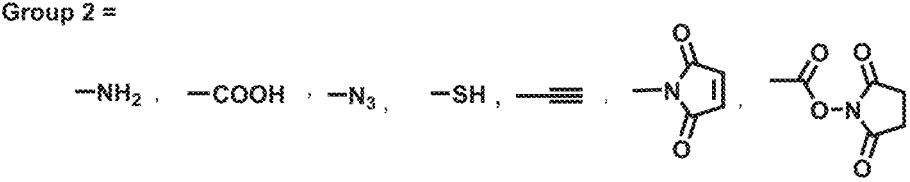
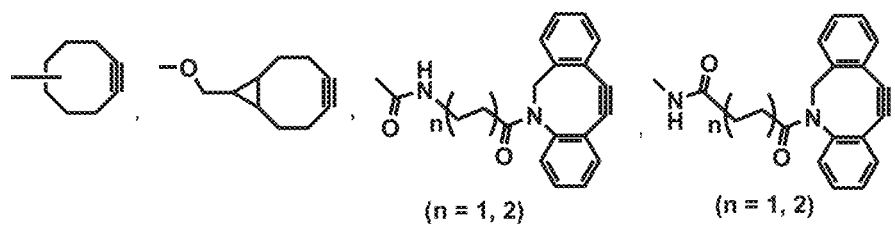
Fig. 9C

Example of the linkage selection for the ligand conjugation sites.
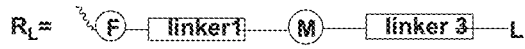
L = ligands, GalNAc, peptide, protein
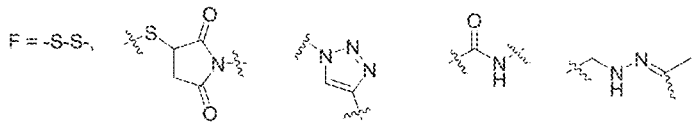
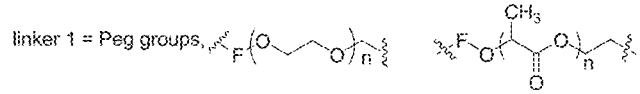
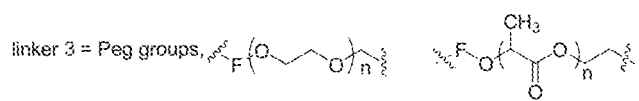
M = bridge site, signle branch or multi branch
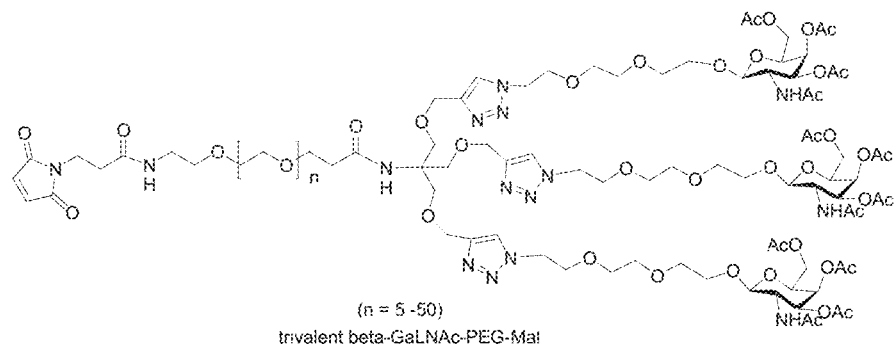
(n = 5 -50)
trivalent beta-GaLNAc-PEG-Mal
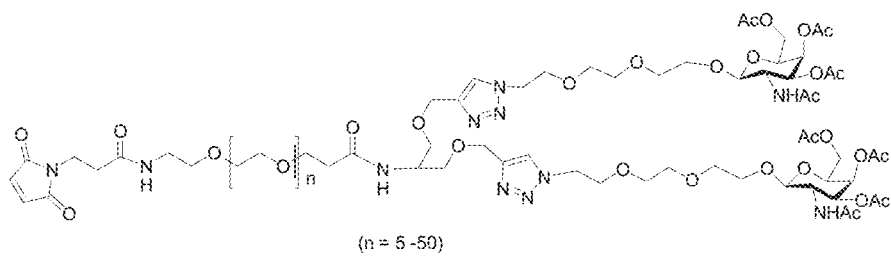
(n = 5 -50)
divalent beta-GaLNAc-PEG-Mal
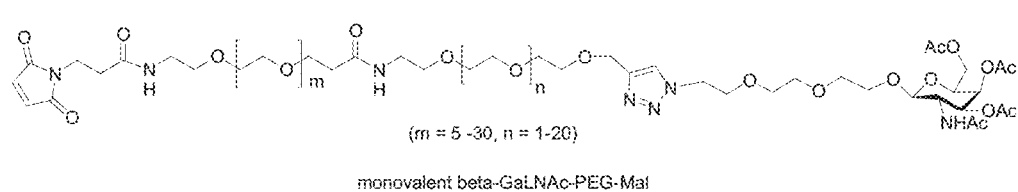
(m = 5 -30, n = 1-20)
monovalent beta-GaLNAc-PEG-Mal
Fig. 10

Representative example of construction of the siRNA- PDoV-ligand compound 2.

Example of construction of the dual siRNA- PDoV-ligand compound 3.

siRNA sequence and structure modifications.

| Sequence | Sequence and modifications |
|---|---|
| ApoB100a sense | 5'-DBCO-C6NHS)(NHC6)GGAAUCuuAuAuuuGAUCcAA-3' (5' end DBCO modification) |
| ApoB100a Antisense | 5'-uuGGAUcAAAuAuAAGAuUCccu-3' |
| ApoB100b sense | S: 5'-DBCO-C6NHS)(NHC6)GGAAUCuuAuAuuuGAUCcAA-3' (5' end DBCO modification) |
| ApoB100b Antisense | AS: 5'-uuGGAUcAAAuAuAAGAuUCccu-(Fluor 647 fluoro)-3' |
| Fully modified ApoB100c sense: | Sense 5'-(DBCO-C6NHS)(NHC6)ggaaucUfuAfUfAfuuugauccaa-3' |
| ApoB100c Antisense-Dye | Antisense 5'-uUfggaUfcaaauauAfaGfauucccu-3' |
| mTTR1 Sense: | 5'-(DBCO-C6NHS)(NHC6)AfaCfaGfuGfuUfcUfuGfcUfcUfaUfaAf-3' |
| mTTR1 antisense | 5'-uUfaUfaGfaGfcAfaGfaAfcAfcUfgUfusUfsu-3' |
| mTTR2 Sense: | 5'-(DBCO-C6NHS)(NHC6)AfsasCfaGfuGfuUfCfUfuGfcUfcUfaUfaAf-3' |
| mTTR2 antisense | 5'-usUfsaUfaGfaGfcAfaGfaAfcAfcUfgUfusUfsu-3' |
| 25 NSC control Sense: | 5'- DBCO-C6NHS)(NHC6)cGfagcaggguaucGfacgauuacaaa-3' |
| 25 NSC control Antisense: | 5'-uuuGfTaaucgucgauAfcccugcucg-3' |
| 21 NSC control Sense: | Sense -5'-(DBCO-C6NHS)(NHC6)caggguAfuCfGfAfcgauuacaaa-3' |
| 21 NSC control Antisense: | Antisense 5'- uUfuguAfaucgucgAfuAfcccug-3' |
| Notes | 2'-modification in all sequence: Uppercase letters indicate 2'-OH; lower case letters indicate 2'-O-methyl(2'-OMe) modification, upper case X= normal nucleotide, Xf=2'-F modification. |

Fig. 14

PEPTIDE DOCKING VEHICLE FOR TARGETED NUCLEIC ACID DELIVERY

SEQUENCE LISTING

The instant application contains a Sequence Listing which has been submitted electronically in ASCII format and is hereby incorporated by reference in its entirety. Said ASCII copy, created on Feb. 4, 2021, is named 4690_0025C_SL.txt and is 26,277 bytes in size.

FIELD OF THE INVENTION

Delivery systems are provided in which single or multi-nucleic acids are covalently conjugated to an endosomal releasing peptide, and are further covalently linked to at least one small molecular ligand. Novel compositions of matter are provided, together with methods for their preparation and use. With the selected ligand and linker, the compositions and systems provide targeted delivery of nucleic acid molecules to the liver and other tissue.

BACKGROUND

Double-stranded RNA has been shown to silence the gene expression (Fire et. al., Nature 391:806-811 (1998), and Elbashir et. al., Nature, 411, 494-498 (2001)) and this phenomenon has been named RNA interference or "RNAi", or interfering RNA molecule (RNAi). Short-interfering RNA (siRNA) induced RNAi regulation shows great potential to treat a wide variety of human diseases from cancer to other traditional undruggable diseases. There are three major advantages of RNA-based therapeutics over traditional small-molecule and antibody therapeutics. First, once delivery to a specific cell type or tissue has been devised (e.g., siRNA/anti-sense oligonucleotide (ASO) delivery to hepatocytes; ASO delivery to the CNS), it is likely that every disease-promoting gene in that cell type can be targeted. Second, RNA therapeutics can selectively target single genes and can be readily engineered to avoid regulating off-target genes, whereas small-molecule inhibitors often hit multiple targets and have unknown off-target side effect. Third, unlike static small molecules and antibodies, RNA therapeutics can pharmacoevolve their sequence to keep pace with, for example, cancer mutations or pandemic influenza. These attributes provide RNA-based therapeutics with great potential to treat undruggable human diseases, provided delivery can be properly solved.

In the field, ASO, RNAi and mRNA chemistry has advanced to enable the improved stability and avoid the innate immune response. It also allows industrial scale production of therapeutic ASO and RNA compounds on a large scale via automated synthesis at relatively low cost compared to antibody or small molecule development. However, two areas still need further development: (a) targeting of these molecules to specific cell types or tissues; and (b) the devising of non-toxic endosomal escape agents. Dowdy, Nature Biotechnology, 35:222-229 (2017).

Two types of effective delivery method are used in marketed ASO or RNAi drugs. One uses lipid based nanoparticle called liposomes that contain multiple components. The other one uses a GalNAc molecule-conjugated ASGPR-targeted (asialoglycoprotein receptor) approach.

A major challenge for RNA-based therapeutics is that all pathways for delivery to cells eventually lead to endosomal escape. ASO and siRNA delivery to the liver can be achieved using ASGPR-targeted GalNAc-siRNA conjugates due to the properties of ASGPR that are well suited for macromolecular drug deliver to hepatocytes. In particular, hepatocytes express millions of copies of ASGPR on their cell surface, which cycle at a rapid rate of every 10-15 min. These properties make a GalNAc-based delivery approach effective even with a presumed endosomal escape rate of <0.01%. By contrast, effective delivery of ASO or RNA to other tissues has not been achieved. No other ligand-receptor system expresses receptors at such a high level as ASGPR, nor cycles into endosomes as rapidly. Indeed, most cell surface receptors are expressed in the range of 10,000-100,000 per cell (or lower), and caveolin and clathrin-mediated endocytosis typically recycles every 90 min. See Juliano, *Nucleic Acids Res.* 44, 6518-6548 (2016).

Endosomal escape remains a problem that applies to all RNA-based therapeutics. Enhancing endosomal escape by developing new chemistries and materials is needed to target the cell or tissue beyond the liver hepatocytes. Small-molecule endosomolytic agents such as chloroquine have been used to disrupt or lyse endosomes, but at the effective concentration these agents invariably lyse all types of endosomes inside the cell resulting in substantial toxicity.

An alternative endosomal escape approach is to conjugate endosomolytic peptides or molecules directly to the RNA, which will strictly limit their action to endosomes containing the RNA therapeutic. Various clinical trials using a two-molecule dynamic polyconjugate (DPC) system containing cholesterol or lytic melittin peptide to escape the endosome were terminated due to toxicity effects. Wooddell, et al., *Mol. Ther.* 21, 973-985 (2013); Hou et al., *Biotechnol. Adv.* 33, 931-940 (2015).

The compositions and methods described below use endosomal release peptides conjugated to oligonucleotides and targeting ligands. The constructs enhance escape of the oligonucleotide cargo into the cytoplasm of cells in a non-toxic manner. The construct of the invention is referred to herein as a "Peptide Docking Vehicle" (PDoV).

SUMMARY OF THE INVENTION

What is provided is a chemical construct containing a Peptide Docking Vehicle (PDoV) covalently linked to (a) a targeting moiety, and (b) a first therapeutic oligonucleotide. The construct may contain a second therapeutic oligonucleotide that is the same as, or different from, the first therapeutic oligonucleotide. The PDoV may contain multiple repeating units of histidine and lysine. In one embodiment the targeting moiety binds to the asialoglycoprotein receptor. The oligonucleotide may contain an siRNA, an antisense oligonucleotide, an miRNA, an saRNA, an shRNA, an aptamer, an RNAzyme, an DNAzyme, a decoy oligonucleotide, or a CpG motif.

In these constructs, the PDoV construct may contain an endosomal release motif that may contain at least two targeting moieties that are the same or different, and/or at least two therapeutic oligonucleotides that are the same or different.

The construct may have one of the structures shown below, where: type X sites are used to conjugate the targeting ligands; Type Y sites are used to conjugate the oligonucleotide, and X and Y can be the same or different; A is a peptide sequence of H, K, R, HH, HHH, HHHH (SEQ ID NO: 1), HHK, HHHK (SEQ ID NO: 2) or any other endosomal releasing short peptide containing up to about 5 amino acids; B is a peptide sequence of H, K, R, HH, HHH, HHHH (SEQ ID NO: 1), HHK, HHHK (SEQ ID NO: 2), or any other short peptide containing up to about 5 amino acids, any other amino acid or combination of amino acids with a linker; D is an oligonucleotide; $R_L$ is ligand; and $R_S$ is a linker to the oligonucleotide.

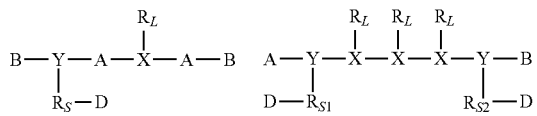

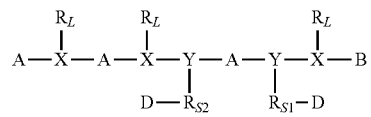

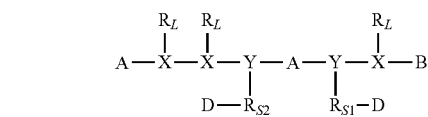

D may be an siRNA, mRNA, or an aptamer.

In these constructs, the PDoV peptide construct may have a structure containing an amino acid sequence selected from the group consisting of KHHHCKH (SEQ ID NO: 3), HKHHHCKH (SEQ ID NO: 4), HHKHHHCKH (SEQ ID NO: 5), HHHKHHHKCHHHKHHH (SEQ ID NO: 6), HHHKHHCKHHH (SEQ ID NO: 7), HHHKHHCRHHH (SEQ ID NO: 8), HKHHCKH (SEQ ID NO: 9), HKHCH (SEQ ID NO: 10), HKHCKH (SEQ ID NO: 11), HKHC (SEQ ID NO: 12), HHHK(S)HHCKHHH (SEQ ID NO: 13), and HHK(S)HHKCHH(S)HHH (SEQ ID NO: 14), where $R_L$ is linked to the side chain of the cysteine residue and $R_S$ is linked to the side chain of the lysine residue, and where (S) is:

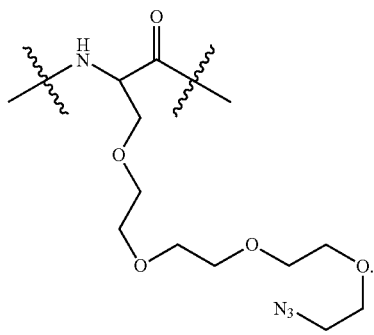 [SMILES: *NC(COCCOCCOCCOCCN=[N+]=[N-])C(*)=O]

In other embodiments, the PDoV peptide construct may have the structure below, in which three of the ligands are conjugated individually on the peptide (SEQ ID NO: 54).

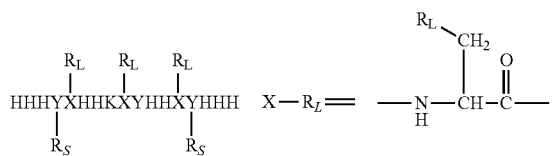

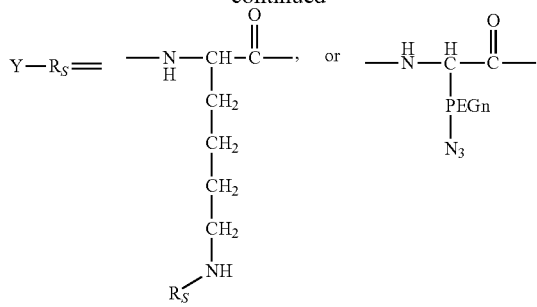

The ligand moiety $R_L$ may contain linker-1, where linker-1 may contain one of the following structures:

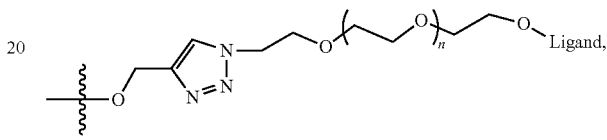

where n is 1, 2, or 3 and is connected to the bridge through a 1, 5-triazol ring with an $OCH_2$ unit; or

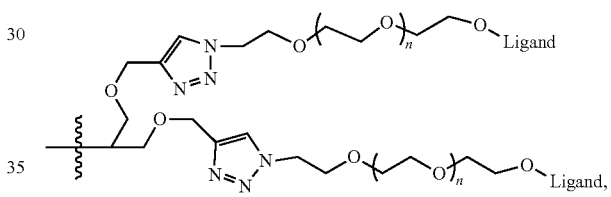

where n is 1, 2, or 3 and is connected to the bridge through a 1, 5-triazol ring with a $CH_2OCH_2$ unit; or

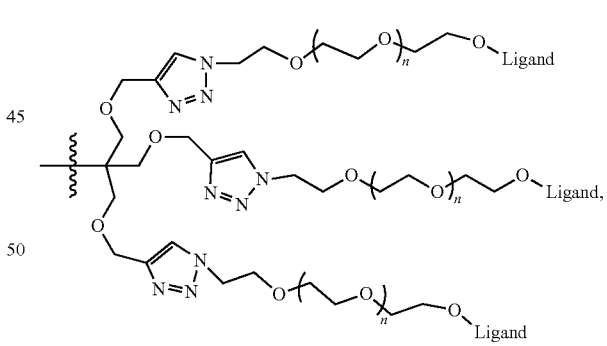

where n is 1, 2, or 3 and is connected to the bridge through a 1, 5-triazol ring with a $CH_2OCH_2$ unit.

The linker between the ligand(s) attached to the PDoV peptide may contain a polyethylene glycol chain $—(CH_2CH_2O)_n—$, or $—(CH_2CH_2)_n—$ chain, where n is an integer from 2-15. The ligand $R_L$ may be linked to the PDoV peptide via a linker that may contain a thioether, an amide, or a triazole linkage.

In other embodiments the oligonucleotide is linked via a moiety having the structure Rs-linker2-oligonucleotide, where linker 2 is an aliphatic chain, a polyethylene glycol chain, a hydrophobic lipid chain or a hydrophilic chain. The group 2 at the end site is the reactive site for the chemical conjugation with the siRNA end.

Linker 2 =

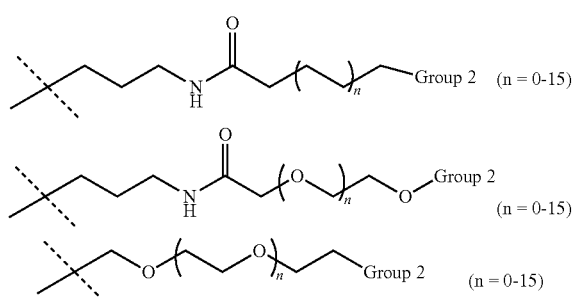

Group 2 =

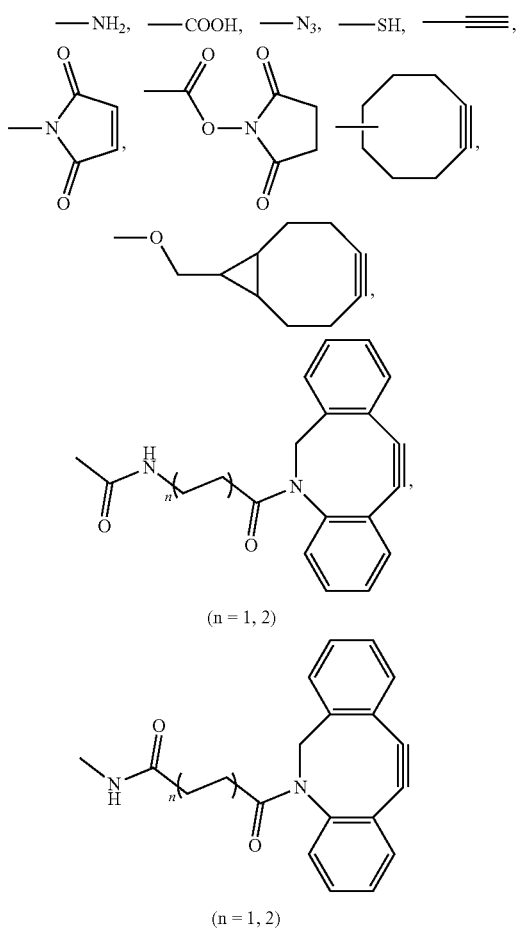

The oligonucleotide may be an RNAi molecule that is single-stranded oligonucleotide with a length of 10-29, or may be a duplex of two complimentary, single-stranded oligonucleotides each with a length between 10-29 bases or 19-27 bases. oligonucleotide may contain deoxyribonucleotides and/or ribonucleotides. The oligonucleotide may contain an siRNA molecule containing at least one or more chemically modified nucleotides at the 2' position, where, for example, the chemically modified nucleotides comprise 2'-O-Methyl or 2'-Fluoro, 2'-O-methoxyethyl, 2'-O-allyl, or 2'-H, modified nucleotides.

In other embodiments, the oligonucleotide may contain an siRNA molecule containing at least one chemically modified linkage that is

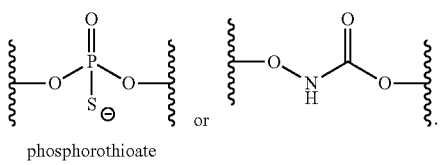 [SMILES: *OP(=O)([S-])O* ; *ONC(=O)O*]

In other embodiments, the siRNA or oligonucleotide is further chemically modified at position 5' or 3' with a linker 3, where Linker 3 contains a complimentary conjugation site group 3 which can covalently react with the linker 2 to link the ligand-PDoV and nucleotides.

In further embodiments, the construct may have a structure as shown below:

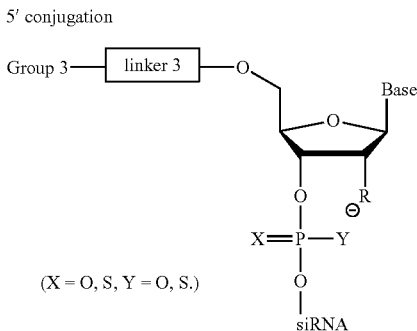

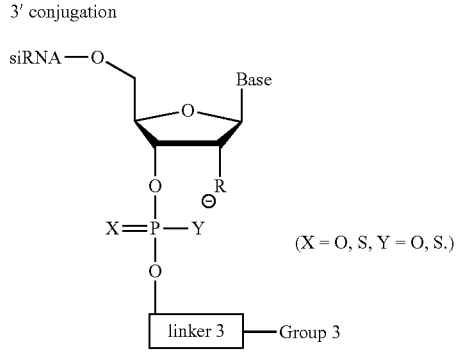

In each of these constructs, the targeting ligand may be selected from the group consisting of N-acetyl-galactosamine (GalNAc), galactose, galactosamine, N-formalgalactosoamine, N-propionyl-galactosamine, N-butanoylgalactosamine and aptamer. In other embodiments the targeting ligand is a peptide selected from the group consisting of cyclic(c) RGD, APRPG (SEQ ID NO: 15), NGR, F3 peptide, CGKRK (SEQ ID NO: 16), LyP-1, iRGD (CRGDRCPDC (SEQ ID NO: 17)), iNGR, T7 peptide (HAIYPRH (SEQ ID NO: 18)), MMP2-cleavable octapeptide (GPLGIAGQ (SEQ ID NO: 19)), CP15 (VHLGYAT (SEQ ID NO: 20)), FSH (FSH-β, 33-53 amino acids, YTRDLVKDPARPKIQKTCTF (SEQ ID NO: 21)), LHRH (QHTSYkcLRP (SEQ ID NO: 22)), gastrin-releasing peptides (GRPs) (CGGNHWAVGHLM (SEQ ID NO: 23)), RVG (YTWMPENPRPGTPCDIFTNSRGKRASNG (SEQ ID NO: 24)), FMDV20 peptide sequence (NAVPNLRGDLQVLAQKVART (SEQ ID NO: 25)), and GLP or is folic acid.

In any of these constructs the peptide may contain an amino acid sequence -HHK, -KHH, -HHH, -HHHK (SEQ ID NO: 2), -KHHH (SEQ ID NO: 26), -HHHHK (SEQ ID NO: 27), -KHHHH (SEQ ID NO: 28), -K(HHHK)n (n=1-8) (SEQ ID NO: 29), -K(HHHHK)n(HHHK)m (n=1-4, m=1-8) (SEQ ID NO: 30), K(HHHHK)n(HHHK)m- (n=1-4, m=1-8) (SEQ ID NO: 31), for example the construct may contain a peptide with a sequence -K(HHHHK)n(HHHK)m (SEQ ID NO: 32), or K(HHHHK)n(HHHK)m-, where n is 1 and m is 3 (SEQ ID NO: 33). The peptide may be an endosomal releasing peptide or may be a cell penetrating peptide.

Also provided is a peptide with the formula $(H_nK_m)_oX_pY_q$, where H is histidine, K is lysine, X and Y are functional units selected from an amino acid and a linker, n is 1-10, m is 1-10, o is 1-10, p is 1-5, and q is 1-4 (SEQ ID NO: 34). The peptide may include at least two conjugation sites for attaching a targeting ligand. Advantageously the conjugation site is lysine or cysteine. The peptide may contain at least two conjugation sites for attaching an oligonucleotide. The construct may contain the peptide of formula $(H_nK_m)_oX_pY_q$ (SEQ ID NO: 34) and at least one targeting ligand linked to the peptide via at least one conjugation site. At least one oligonucleotide may be linked to the peptide via at least one conjugation site. The targeting ligand may be selected from the group consisting of cyclic (c) RGD, APRPG (SEQ ID NO: 15), NGR, F3 peptide, CGKRK (SEQ ID NO: 16), LyP-1, iRGD (CRGDRCPDC (SEQ ID NO: 17)), iNGR, T7 peptide (HAIYPRH (SEQ ID NO: 18)), MMP2-cleavable octapeptide (GPLGIAGQ (SEQ ID NO: 19)), CP15 (VHLGYAT (SEQ ID NO: 20)), FSH (FSH-β, 33-53 amino acids, YTRDLVKDPARPKIQKTCTF (SEQ ID NO: 21)), LHRH (QHTSYkcLRP (SEQ ID NO: 22)), gastrin-releasing peptides (GRPs) (CGGNHWAVGHLM (SEQ ID NO: 23)), RVG (YTWMPENPRPGTPCDIFTNSRGKRASNG (SEQ ID NO: 24)), FMDV20 peptide sequence (NAVPNLRGDLQVLAQKVART (SEQ ID NO: 25)), and GLP. The oligonucleotide may be selected from the group consisting of an siRNA, an antisense oligonucleotide, an miRNA, an saRNA, an shRNA, an aptamer, an RNAzyme, an DNAzyme, a decoy oligonucleotide, and a CpG motif.

Also provided are pharmaceutical compositions containing a construct as described above claim and a pharmaceutically acceptable carrier. The pharmaceutically acceptable carrier may contain histidine -lysine rich polypeptide HKP, HKP(H), or lipofectamine, and/or may contain water and one or more of the group consisting of: potassium phosphate monobasic anhydrous NF, sodium chloride USP, sodium phosphate dibasic heptahydrate USP, glucose, and Phosphate Buffered Saline (PBS).

Also provided are methods of delivering an oligonucleotide to a cell, which include contacting the cell with a construct or pharmaceutical composition as described above.

Also provided are methods of delivering an oligonucleotide to a hepatocyte cell, which include contacting the cell with a construct as described above.

In these methods, the oligonucleotide may be an siRNA molecule and may be delivered to the mammalian cell or hepatocyte in vivo. The cell may be a human cell.

Also provided are methods of gene therapy in a mammal by administering a therapeutically effective amount of a construct as described above to the mammal, where the mammal optionally is a human.

Also provided are methods of treating cancer in a mammal, such as a human, including administering to the mammal a therapeutically effective amount of a construct as described above. The cancer may be a solid tumor. The cancer may be liver cancer, colon cancer, or pancreatic cancer. The liver cancer may be hepatocellular carcinoma, metastatic colon cancer, or metastatic pancreatic cancer. The construct may be injected directly into a tumor containing the cancer cells.

BRIEF DESCRIPTION OF THE FIGURES

FIG. 9C shows how the linker 2 in the conjugation Rs-linker2-siRNA is a chemical spacer between the peptide and the conjugation site, allowing the conjugation site to be attached at the linker's terminal site. The linker 2 can be an aliphatic chain or a polyethylene glycol chain, or other hydrophobic lipid or hydrophilic chain. The group 2 at the end site is the reactive site for the chemical conjugation with the siRNA end.

FIG. 10 shows an example of the linkage selection for the ligand conjugation sites. The linkage for the ligand conjugation $R_L$ can be a selection based on the monovalent GalNAc molecule, bivalent GalNAc molecule and trivalent GalNAc molecule. The conjugation site can be maleimide/thiol or may be selected from the Group 2 list shown in FIG. 9.

FIG. 14 shows a list of some possible siRNA sequence and structure modifications (SEQ ID NOS 43-44, 43-51, 38, and 52-53, respectively, in order of appearance).

DESCRIPTION OF THE INVENTION

Definitions

Figure 1:
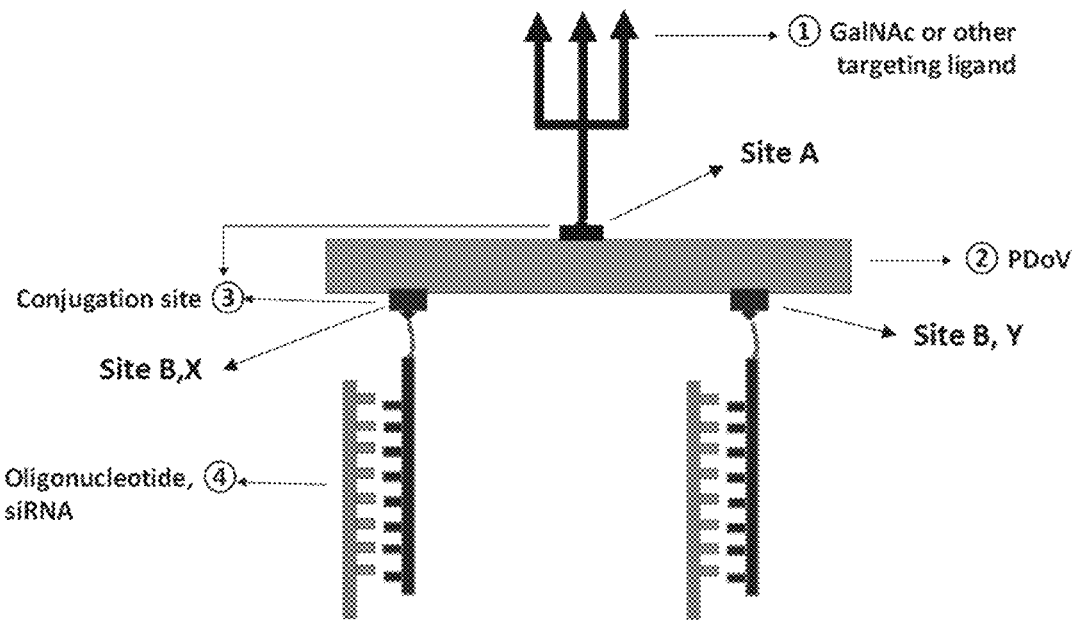
FIG. 1 shows a cartoon representation of the design of the [GalNAc] Peptide Docking Vehicle (G-PDoV). Trivalent GalNAc was covalently conjugated on one docking site A. Oligonucleotide or siRNA was conjugated on the other one or two docking sites B respectively.
Figure 2:
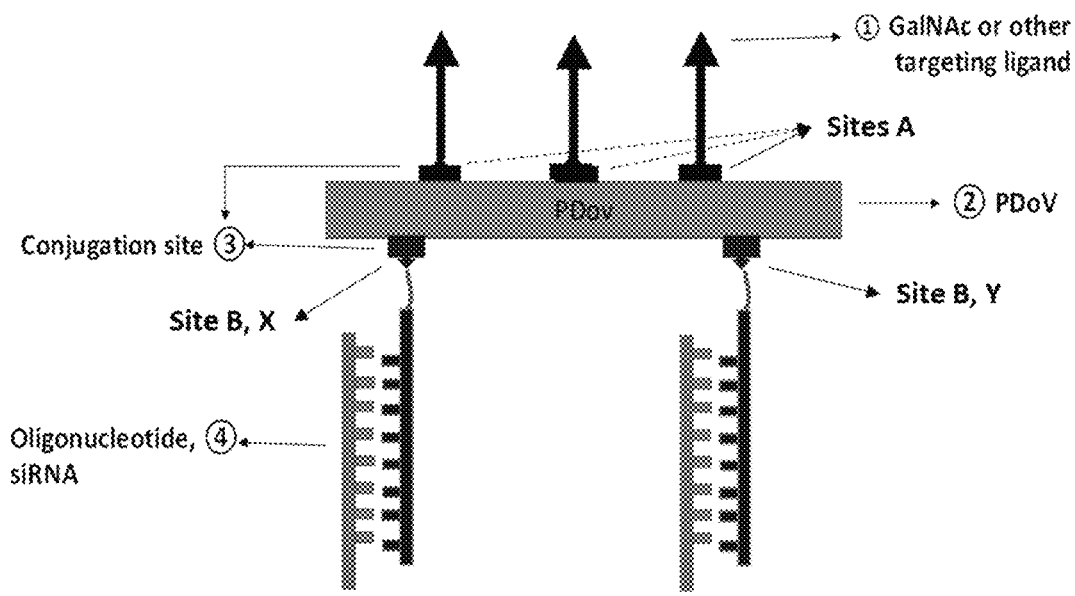
FIG. 2 shows a cartoon representation of an alternative design of a [ligand] Peptide Docking Vehicle. Monovalent GalNAc was covalently conjugated at one to four docking sites A. Oligonucleotide or siRNA were conjugated on the other one or two docking sites B respectively.

As used herein, "oligonucleotide" refers to a chemically modified or unmodified nucleic acid molecule (RNA or DNA) having a length of less than 100 nucleotides (for example less than 50, less than 30, or less than 25 nucleotides). It can be siRNA, microRNA, anti microRNA, microRNA mimics, dsRNA, ssRNA, aptamer, triplex forming oligonucleotides, aptamers. In one embodiment, the oligonucleotide is an RNAi agent. As used herein, an "siRNA molecule" or "RNAi molecule" is a duplex oligonucleotide, that is a short, double-stranded polynucleotide, that interferes with the expression of a gene in a cell, after the molecule is introduced into the cell. For example, an siRNA molecule targets and binds to a complementary nucleotide sequence in a single stranded target RNA molecule. By convention, when an siRNA molecule is identified by a particular nucleotide sequence, the sequence refers to the sense strand of the duplex molecule. One or more of the ribonucleotides comprising the molecule can be chemically modified by techniques known in the art. In addition to being modified at the level of one or more of its individual nucleotides, the backbone of the oligonucleotide can be modified. Additional modifications include the use of small molecules (e.g. sugar molecules), amino acids, peptides, cholesterol, and other large molecules for conjugation onto the siRNA molecule.

"Peptide Docking Vehicle" (PDoV) refers to a synthetic peptide of defined sequence that contains multiple conjugation sites to allow conjugation with one or more targeting ligands and with one or more oligonucleotides. It contains functional groups, such as a hydrophobic chain or a pH sensitive residue, which facilitate the release of the oligonucleotide payload entrapped inside of the endosome of a cell after delivery of the conjugated PDoV to the cell.

Compositions and methods using interfering RNA molecules having enhanced therapeutic benefit are provided. The compositions and methods allow targeted cell/tissue delivery of a therapeutic compound, such as an siRNA molecule, to a subject by linking a targeting ligand to the compound. The subject may be an animal or a human.

In some embodiments, the targeting ligand as described herein may be conjugated to an endosome releasing peptide through an orthogonal bioconjugation method. The targeting ligand may particularly be used to improve the delivery of RNAi molecules to a selected target, such as the liver. In other embodiments, the targeting ligand(s) permit targeted delivery of RNAi molecules into other tissues, for example, in the skin and brain.

The targeting ligands as described herein may include one or more targeting moieties and one or more linkers. The linkers are covalently conjugated with the siRNA and targeting ligands through click chemistry, thiol/maleimide chemistry, or other bioorthogonal chemistry. Linkers advantageously are hydrophilic and can be, for example, a water soluble flexible polyethylene glycol (PEG) which is sufficiently stable and limits the potential interaction between one or more targeting moiety(s). PEG has been validated to be safe and compatible for therapeutic purposes from clinical studies. In some embodiments, the linker can be poly (L-lactide)$_n$ (where n=5-20) of defined molecular weight, where the ester bond is enzymatically or hydrolytically labile.

The targeting ligand may include one or more targeting moieties, one or more groups with a linker reactive connection moiety. They are covalently conjugated with the siRNA and targeting ligands through click chemistry, thiol/maleimide chemistry, or other bioorthogonal chemistry. The linker reactive connection moiety may be, but is not limited to, a thiol-maleimide linkage, a triazol linkage formed by reaction of an alkyne and an azide, and an amide formed from an amine-NHS ester linkage. Each of these linkages is suitable for covalently linking both the targeting ligands and the therapeutic compound.

In some embodiments, the targeting ligands disclosed here include one or more targeting moieties, one or more linkers with reactive connection moiety. The linker contains a thiol moiety, or maleimide moiety, carboxylic acid, or amine, azido group, alkyne group, and the like.

In some embodiments, the targeting specific RNA compound disclosed herein can be directly conjugated to an endosome releasing docking peptide via the 3' or 5' terminal end of the RNA. The targeting ligand (for example N-acetylgalactosamine) also be conjugated with the same docking peptide in a compatible method.

In some embodiments, the targeting specific RNA compound disclosed herein can also be directly conjugated to a targeting ligand (for example N-acetyl-galactosamine), via, for example, the 3' or 5' terminal end of the RNA. In some embodiments, the RNA may contain one or more modified nucleotides such as 3'-OMe, 3'-F, or 3'-MOE. In some embodiments, the RNA can be an RNAi agent, for example a double stranded RNAi agent. In some embodiments, the targeting ligands disclosed herein are linked to the 5' or 3' terminus of the sense strand of a double stranded RNAi agent or the 5' or 3' terminus of the antisense strand of a double stranded RNAi agent. The targeting ligands may alternatively be linked to both 3'/3", 3'/5' or 5'/5' terminal end of the sense and antisense strand of a double stranded RNAi agent.

The targeting ligands may be covalently bonded to the RNAi molecule via, for example, a phosphate, phosphorothioate, or phosphonate group at the 3' or 5' terminus of the sense strand of a double stranded RNAi agent. In some embodiments, the targeting specific RNA compound disclosed herein is a TGF 01 or an ApoB100, mRNA expression-inhibition specific compound.

The PDoV enhances escape of its macromolecular cargo into the cellular cytoplasm in a non-toxic manner. This allow effective delivery of, for example, RNAi therapeutics. An endosomal escape peptide (PDoV) is provided that enhances escape of macromolecular cargo, such as an siRNA molecule, into the cytoplasm in a non-toxic manner. Various examples of the PDoV platform are shown in FIGS. 1-4. In the PDoV the endosomal escaping peptide acts both as the docking site linker for the RNA and the targeting ligands. Multiple RNA molecules can be conjugated with the same construct to achieve codelivery of siRNA molecules against different target mRNAs, thereby providing a synergistic benefit for silencing a multi-disease related gene. The histidine and lysine rich polypeptide or linear histidine and lysine rich peptide has been shown to be an effective cell penetrating and endosomal release agent in the delivery of RNA. The peptide contains a histidine rich domain, where the imidazole rings of the histidine residues are protonated at a lower pH value (pH<~6) and act inside the endosome as a proton sponge, which leads to lysis of the endosome lipid bilayers and release of the RNA. The conjugation sites on the PDoV are described in more detail below.

In the next few sections, each component will be discussed in detail including RNAi agent, targeting ligands, linkers between RNAi and peptide, linkers between ligand and peptide, and endosome releasing docking peptide.

RNAi Agents

The RNAi molecules are double stranded compounds. For example, the double stranded siRNA can be anti-TGFβ1 or anti-ApoB100, and can be unmodified or chemically modified at the 2' position with, for example, 2'-OCH$_3$, 2'-F, or 2'-O-MOE, or at the 5' position with —P(O)$_2$=S. Other chemical modifications are known in the art and can include, for example, pegylation or lipid functionalization to improve the overall stability and bioavailability of the RNAi.

In specific embodiments, the double stranded siRNA may be derived duplexes consisting of 24, 23, 22, 21, 20, 19, 18, 17 or 16 contiguous base pairs of any one or more of the duplexes in FIG. 14.

Targeting Ligands

The targeting ligand moiety may be, for example, N-acetyl-galactosamine (GalNAc), galactose, galactosamine, N-formal-galactosamine, N-propionyl-galactosamine, N-butanoylgalactosamine, cRGD, GLP peptide or other small molecules. The targeting ligands are covalently coupled to the peptide by a covalent bond. The number ligands can be 1, 2, or 3. The targeting ligands disclosed here were has a structure represented by the following:

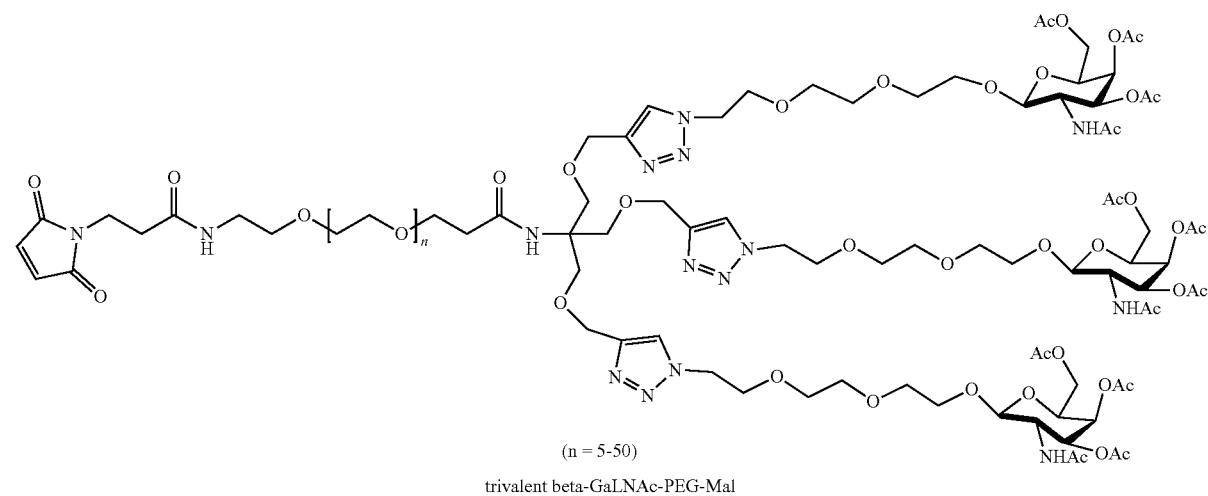

Figure 9A:
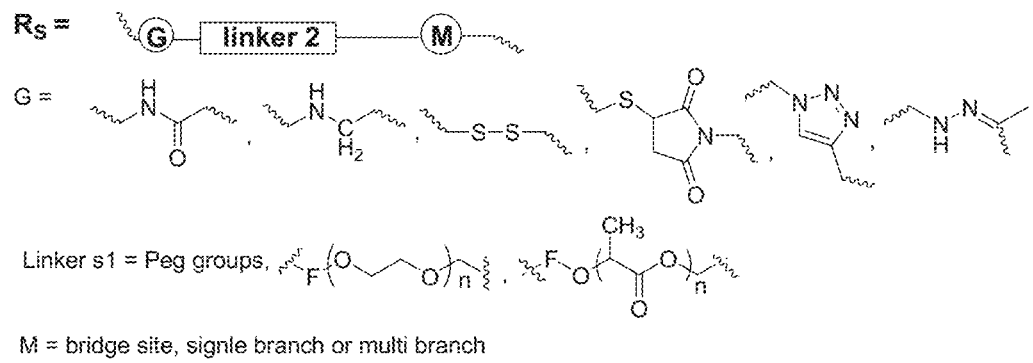
FIG. 9A shows linkage selection for the conjugation sites. Chemical group Rs represents a "click" like reactive moiety to conjugate the oligonucleotide with the PDoV peptide vehicle. The reactive moiety can be amine, hydrazine, N-hydroxysuccinimide, azido, alkyne, carboxylic acid, thiol, maleimide, or other chemical reactive moiety known in the art
Figure 9B:
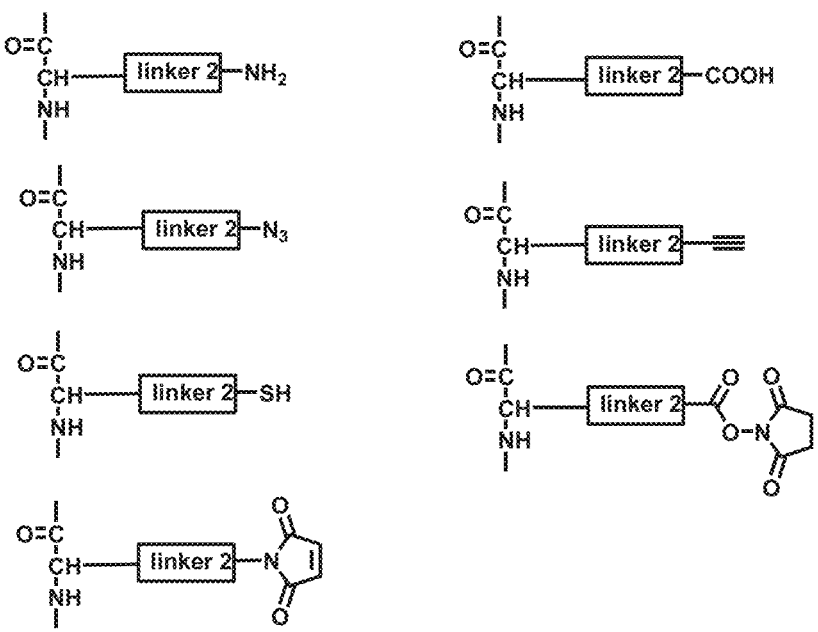
FIG. 9B shows representative examples of the linkage.
Figure 11:
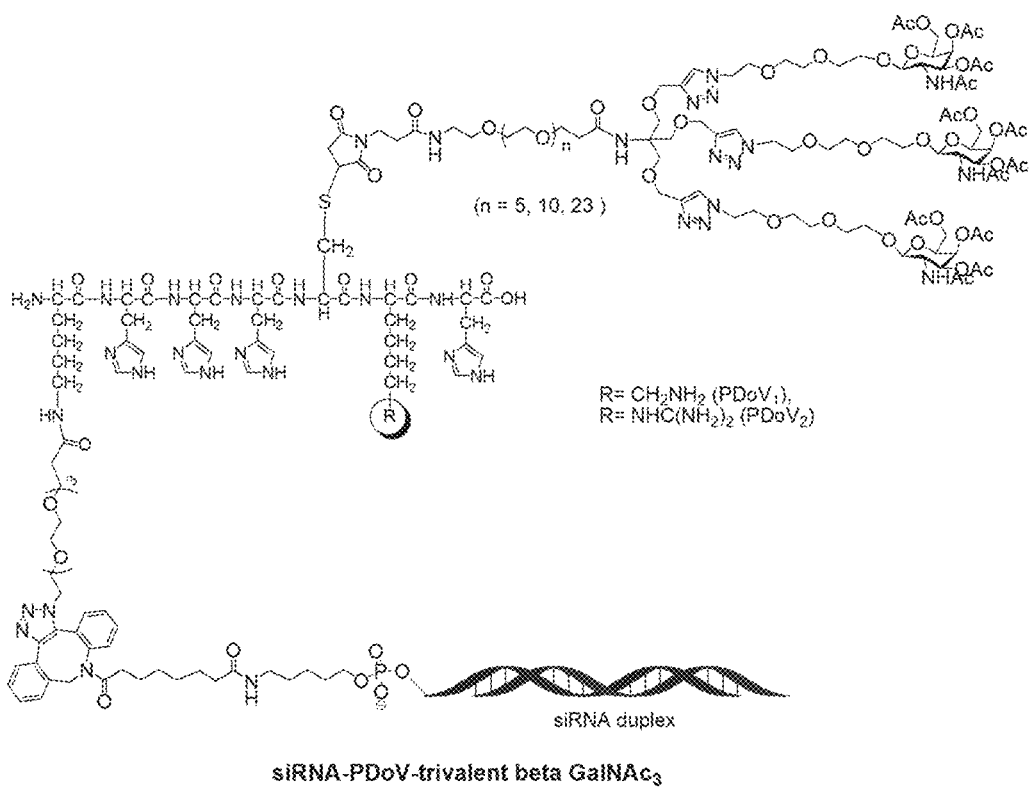
FIG. 11 shows a representative example of the construction of the siRNA-PDoV-ligand compound 1
Figure 12:
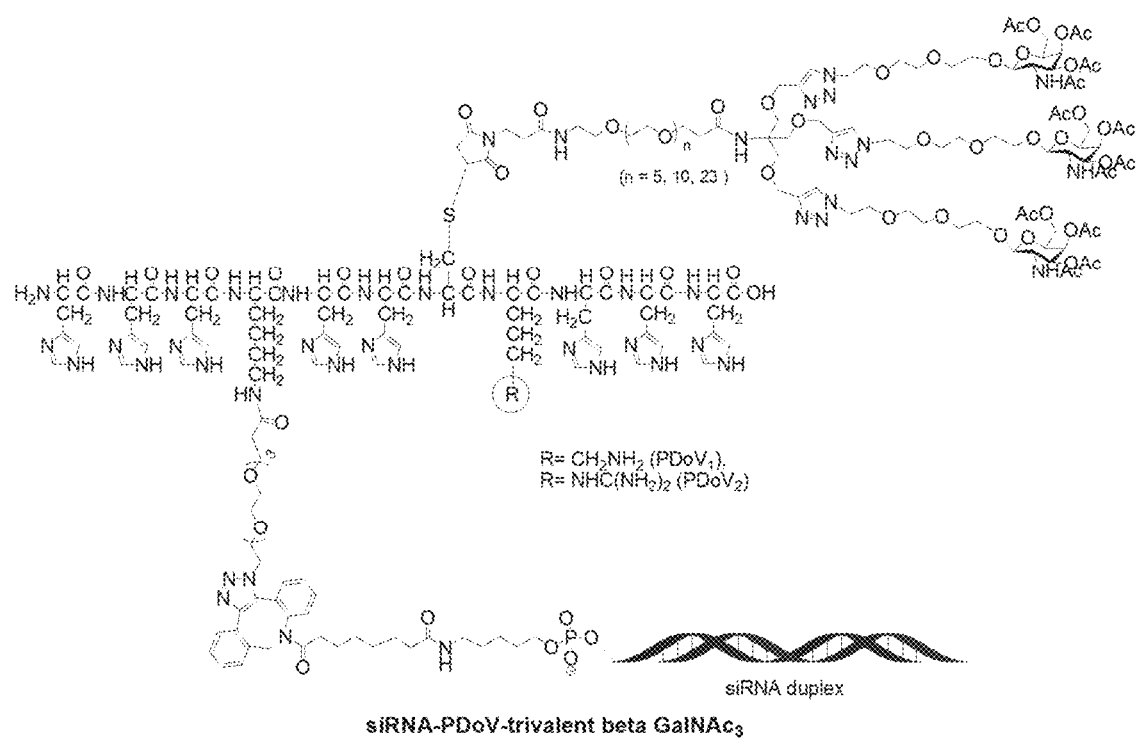
FIG. 12 shows a representative example of construction of the siRNA-PDoV-ligand compound 2.
Figure 13:
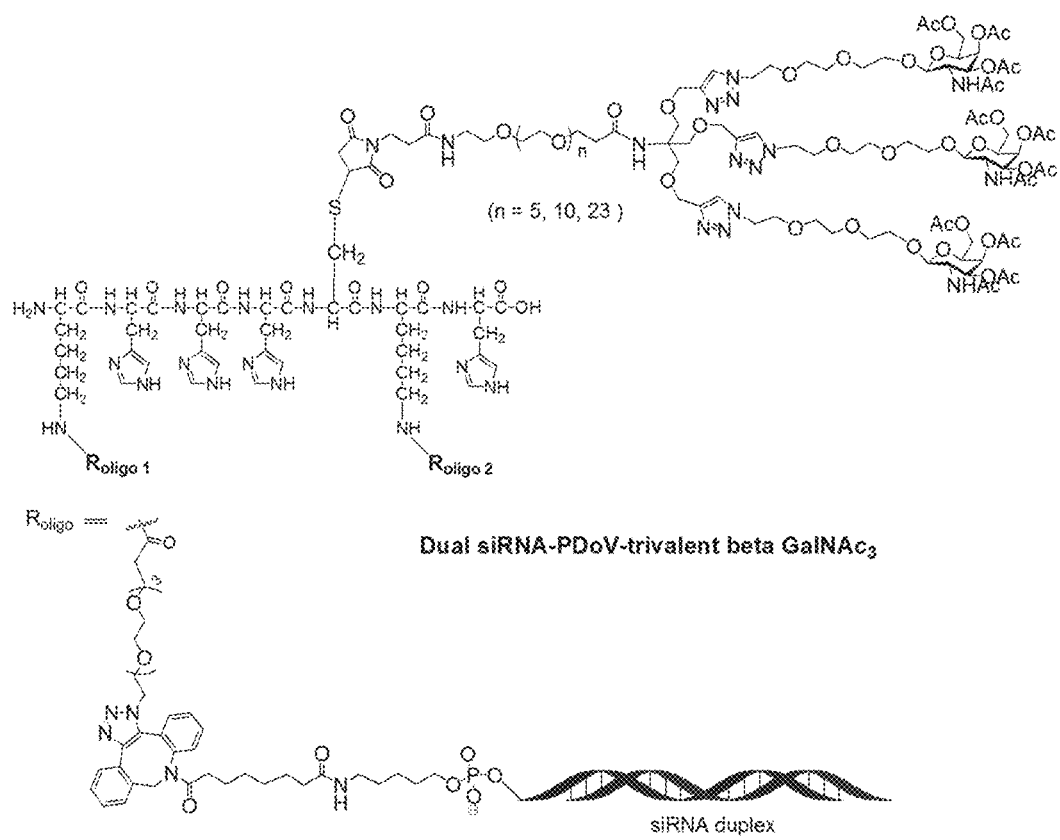
FIG. 13 shows a representative example of construction of the siRNA-PDoV-ligand compound 3.

(n = 5-50)

trivalent beta-GaLNAc-PEG-Mal (n = 5-50)
divalent beta-GaLNAc-PEG-Mal (m = 5-30, n = 1-20)
monovalent beta-GaLNAc-PEG-Mal Linkers Between RNAi and Peptide Linkage for the ligand conjugation Rs: Chemical group Rs may be one of various "click" like reactive moieties used to conjugate the oligonucleotide with the PDoV peptide vehicle. Rs can be amine, hydrazine, N-hydroxysuccinimide, azido, alkyne, carboxylic acid, thiol, or maleimide, or other chemical reactive moieties known in the art. Representative examples are shown in FIG. 9.

The linker 2 in the conjugation Rs-linker2-siRNA is a chemical spacer disposed between the peptide and the conjugation site, which allow the conjugation site to be attached at the linker's terminal site. The linker 2 can be an aliphatic chain or a polyethylene glycol chain, or other hydrophobic lipid or hydrophilic chain. The group 2 at the end site is the reactive site for the chemical conjugation with the siRNA end.

Linkers Between Ligand and Peptide

The targeting ligand and the RNAi moiety disclosed herein contains a linker-1, which directly connect the siRNA (3' or 5' end of the sense strand) and the bridge that contains the linker3-ligands links to the RNAi by the 3' or 5' terminal end the sense strand. The spacing of the linker-1 is a structure of selected from the linear polyethylene glycol, wherein n can be the number of ethylene glycol units in is 1 to 50, or poly(L-lactide) wherein the n can be the number of repeating units of ethyl ester is between from 11 to 50 or average molecular weight from 100 to 3500The conjugation site can be the maleimide/thiol or selected from the Group 2 list in FIG. 10.

Endosome Releasing Docking Peptide

Figure 3:
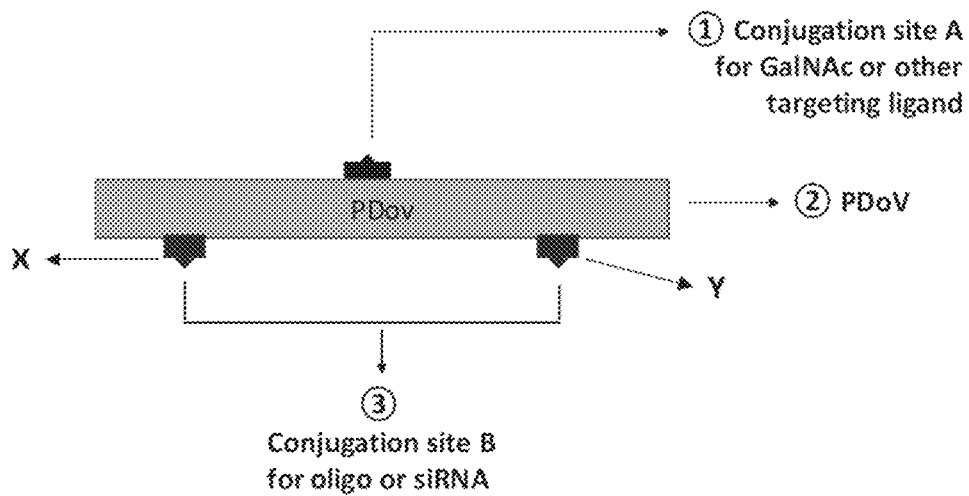
FIG. 3 shows the design of the Peptide Docking Vehicle (PDoV): it has a $(H_nK_m)_oX_pY_q$ peptide backbone with multiple repeating units of histidine (H), lysine (K) and functional units X and Y (amino acid, or functional linker), wherein n=1-10, m=1-10, o=1-10, p=1-5, q=1-5 (SEQ ID NO: 35). HK repeating units have been shown to have good cell penetrating ability, and to facilitate endosome release, the lysine or the various functional unit X or Y will be adopted as the docking sites for the conjugation of ligands and Y will be adopted as the docking sites for the conjugation of oligonucleotide through a different covalent linkage. For example, the site ① will only be able to react in the presence of ligand such as GalNAc or other targeting ligands. The site ③ can only conjugate with oligonucleotide and siRNA under the specific condition.

The Peptide Docking Vehicle (PDoV) advantageously has one ligand conjugation site together with multiple oligonucleotide sites. The PDoV has a peptide backbone with the general structure: $(H_nK_m)_oX_pY_q$ with multiple repeating units of histidine (H), lysine (K) and functional units X and Y (where X or Y is an amino acid, or an amino acid derivative selected from Linker 1 and the functional groups shown in FIG. 10, and where: n=1-10; m=1-10; o=1-10, p=1-5, and q=1-5 (SEQ ID NO: 35). Note that Y in the context of a PDoV does not refer to the amino acid tyrosine—rather it defines a functional amino acid or linker. HK repeating units have been demonstrated to facilitate endosome release. The lysine residues or the functional unit(s) X may be used as docking sites for the conjugation of ligands and Y provides docking sites for the conjugation of oligonucleotide via a different covalent linkage. FIG. 3 shows a schematic of how the PDoV may be conjugated. For example, site ① is only able to react in the presence of ligand such as GalNAc or other targeting ligands. Site ③ can only conjugate with oligonucleotide and siRNA under selected conditions, as exemplified in FIG. 10.

Alternatively, the PDoV may have three ligand conjugation sites and multi oligonucleotide sites (see FIG. 4): a $(H_nK_m)_oX_pY_q$ peptide back bone has multi-repeating units of histidine (H), lysine (K) and functional units X and Y (amino acid, or functional linker), where the n=1-10, m=1-10, o=1-10, p=1-5, q=1-5 (SEQ ID NO: 35). HK repeating units have been demonstrated to have good cell penetrating ability and to facilitate endosome release. The lysine or the various functional units X are adapted as the docking sites for the conjugation of ligands, and Y is adapted the docking sites for the conjugation of oligonucleotides through different covalent linkages. For example, the site (will only be able to react in the presence of a ligand such as GalNAc or other targeting ligands. The site @ can only conjugate with oligonucleotides and siRNAs under specific conditions. See FIG. 4.

Figure 5:
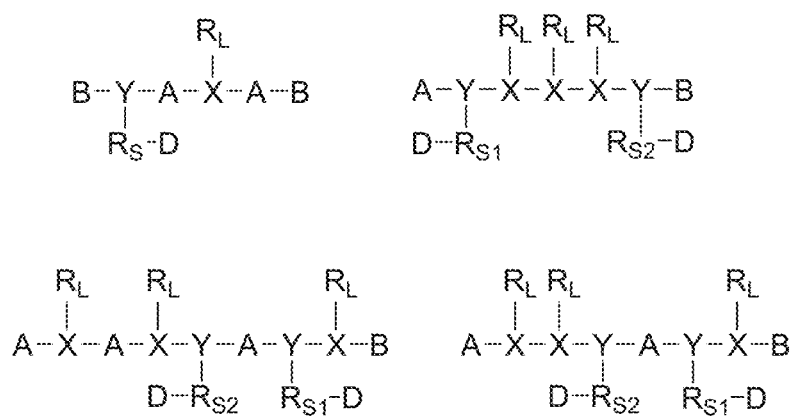
FIG. 5 shows the structure of the PDoV construct. The PDoV construct is a cell penetrating/endosome releasing peptide inserted with multiple conjugation sites X and Y. Site X is used to conjugate the targeting ligand, and site Y is used to conjugate multiple oligonucleotide or nucleic acid. Some construct examples for the PDoV include where: A represents a peptide sequence K, R, H, HH, HHH, HHHH (SEQ ID NO: 1), HHK, HHHK (SEQ ID NO: 2) or other short peptide; B represents a peptide sequence K, R, H, HH, HHH, HHHH (SEQ ID NO: 1), HHK, HHHK (SEQ ID NO: 2), or other short peptide, other amino acid or combination; D represents oligonucleotide, siRNA, mRNA, aptamer; RL represents ligand; and RS represents linker to oligonucleotide.

In the structure design, the PDoV construct is an endosome releasing peptide inserted with multiple conjugation sites X and Y. Site X is used to conjugate the targeting ligand, and site Y is used to conjugate multiple oligonucleotide or nucleic acid. Some examples of the constructs for the PDoV are shown in FIG. 5, where: A represents peptide sequence K, R, H, HH, HHH, HHHH (SEQ ID NO: 1), HHK, HHHK (SEQ ID NO: 2) or other short peptide; B represents peptide sequence K, R, H, HH, HHH, HHHH (SEQ ID NO: 1), HHK, HHHK (SEQ ID NO: 2), or other short peptide or other amino acid or combination; D represents oligonucleotide, siRNA, mRNA, or aptamer; RL represents ligand; and RS represents a linker to the oligonucleotide. In some embodiments, the peptide contains 5-15 amino acids.

Figure 6:
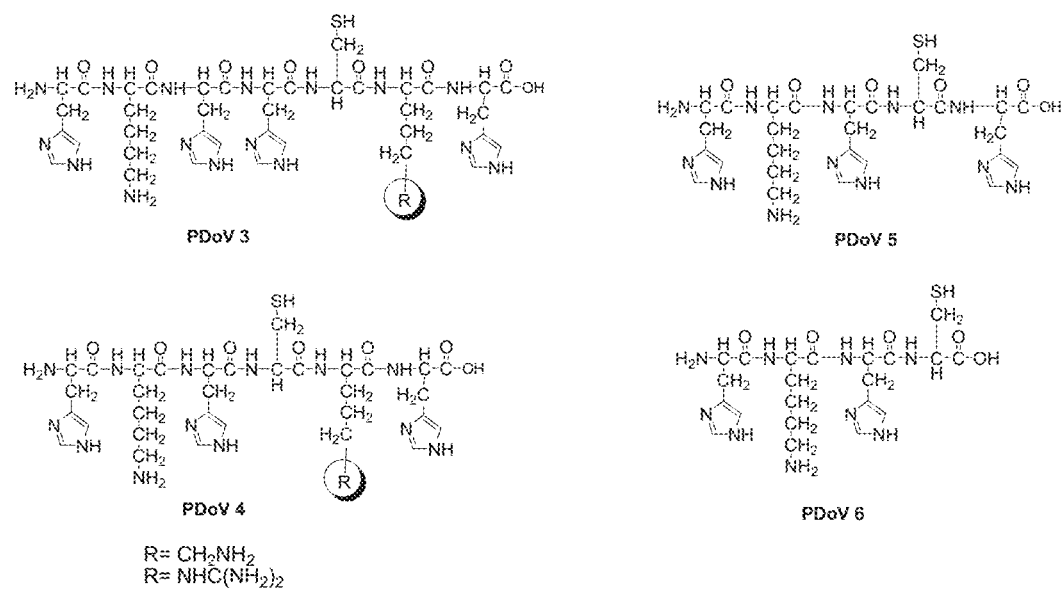
FIG. 6 shows an example of the structure of a first generation PDoV, containing one or two oligonucleotide sites and one ligand conjugation site.

In some embodiments, the PDoV has a structure as shown in FIG. 6.

EXAMPLES
Example 1
Schematic Representative Example of Construction of the siRNA-PDoV-Ligand Compound. One or Two of the siRNA Molecules can be Conjugated with the PDoV Peptide.
Step 1. Peptide Azido Modification:
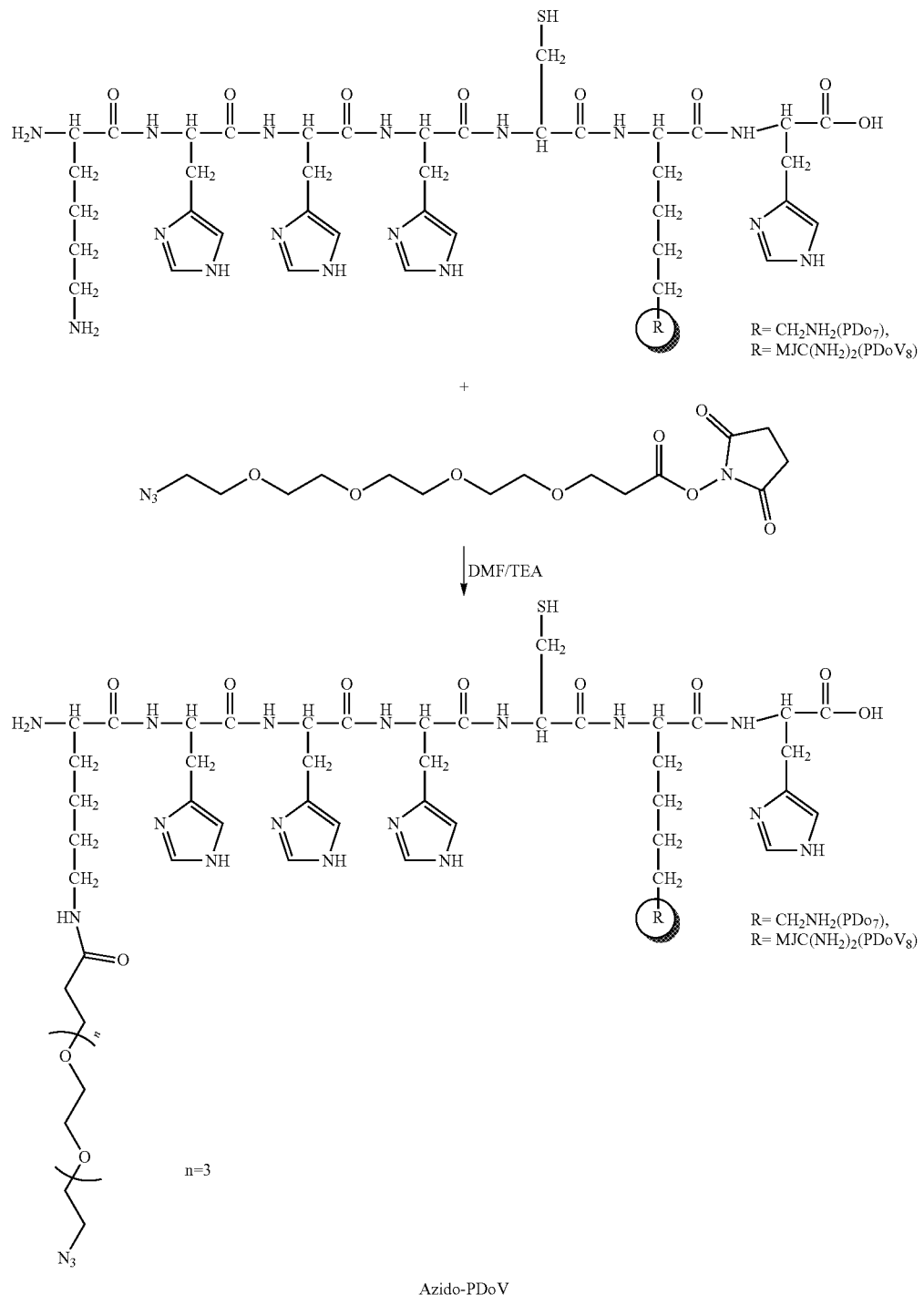
Azido-PDoV
Step 2. Conjugation of Targeting Ligand with the Peptide

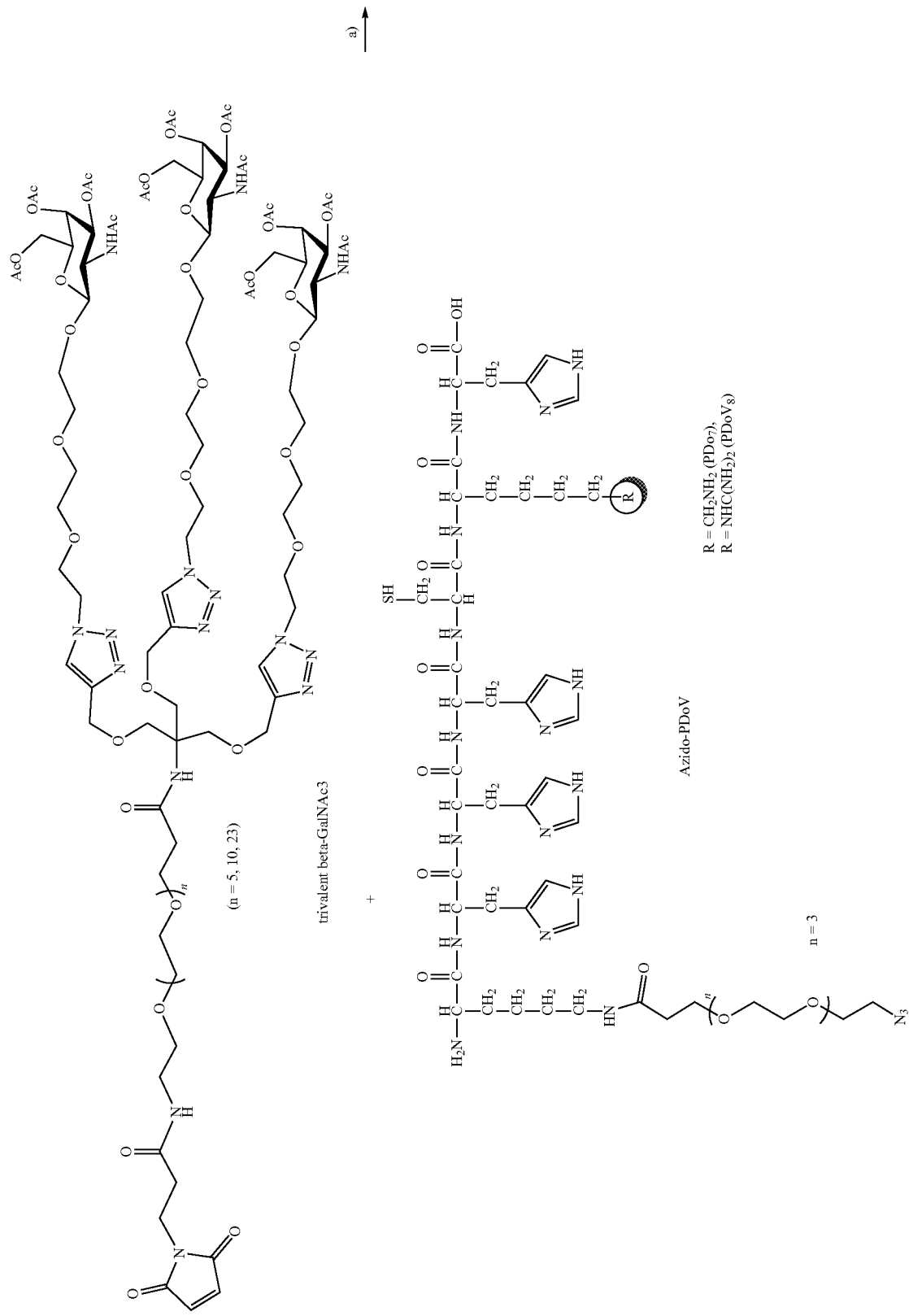

-continued
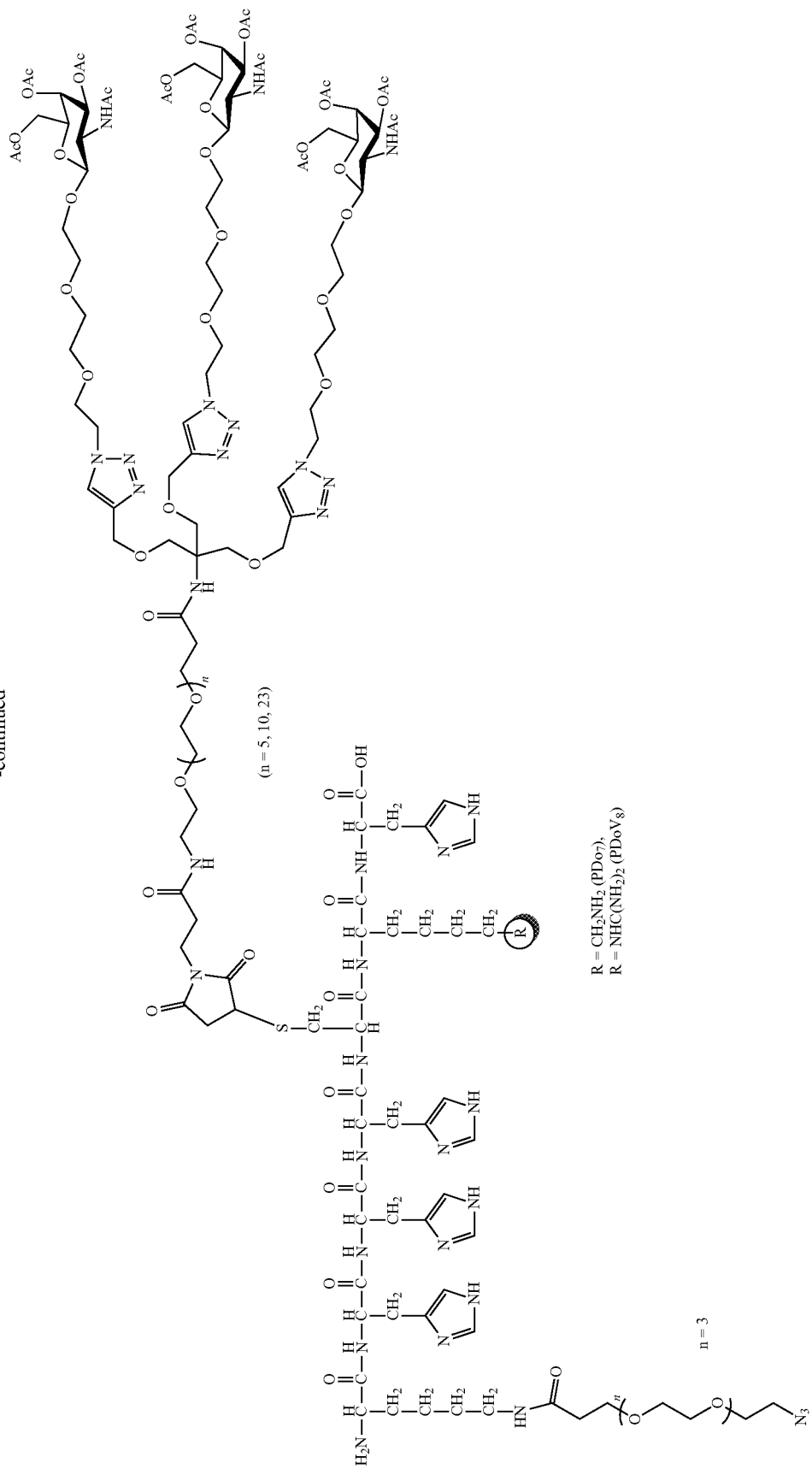
Azido-PDoV-trivalent beta GalNAc3

Step 3 and Step 4. Oligonucleotide Conjugation with the Azido-PDoV-GalNAc3

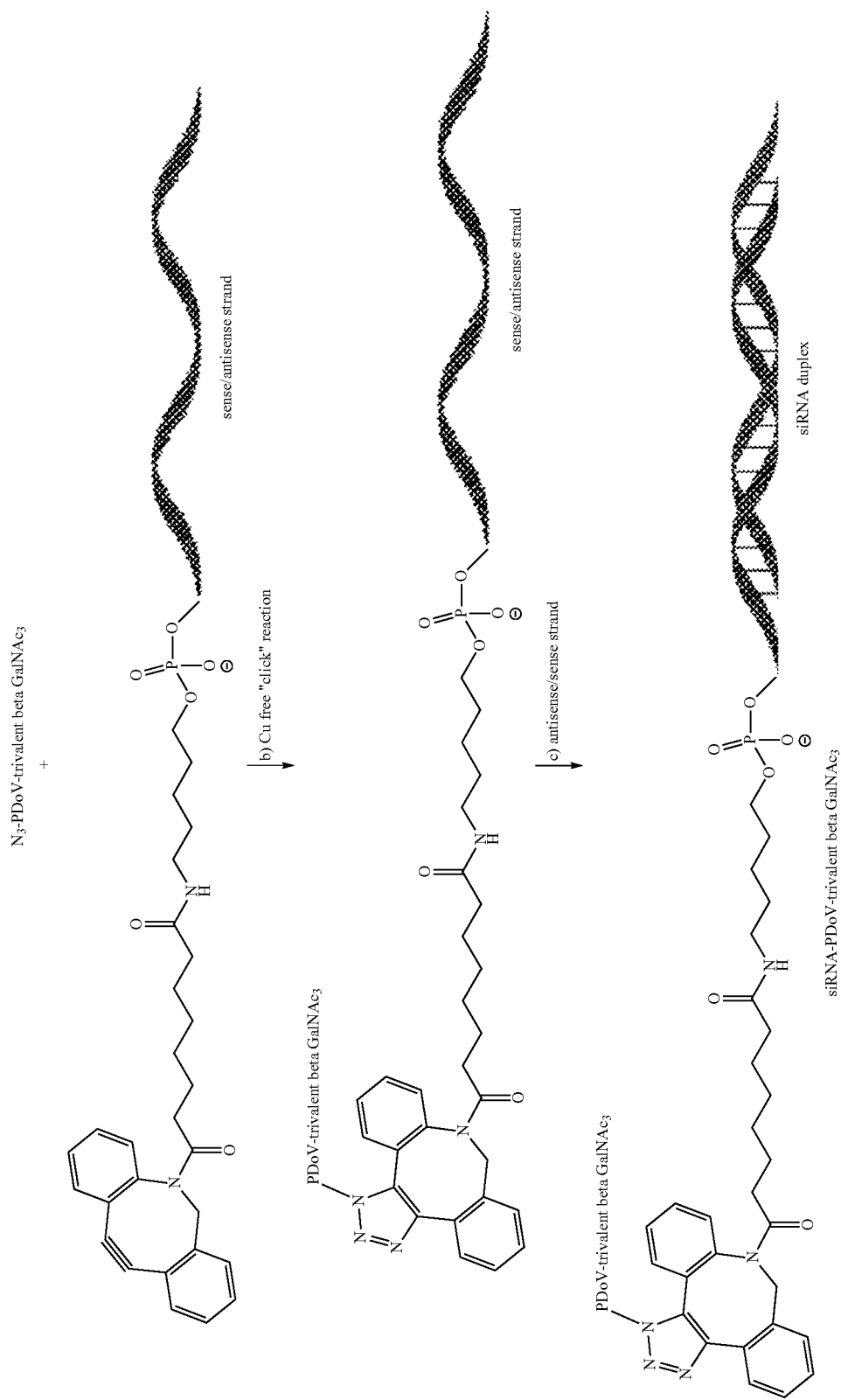

-continued
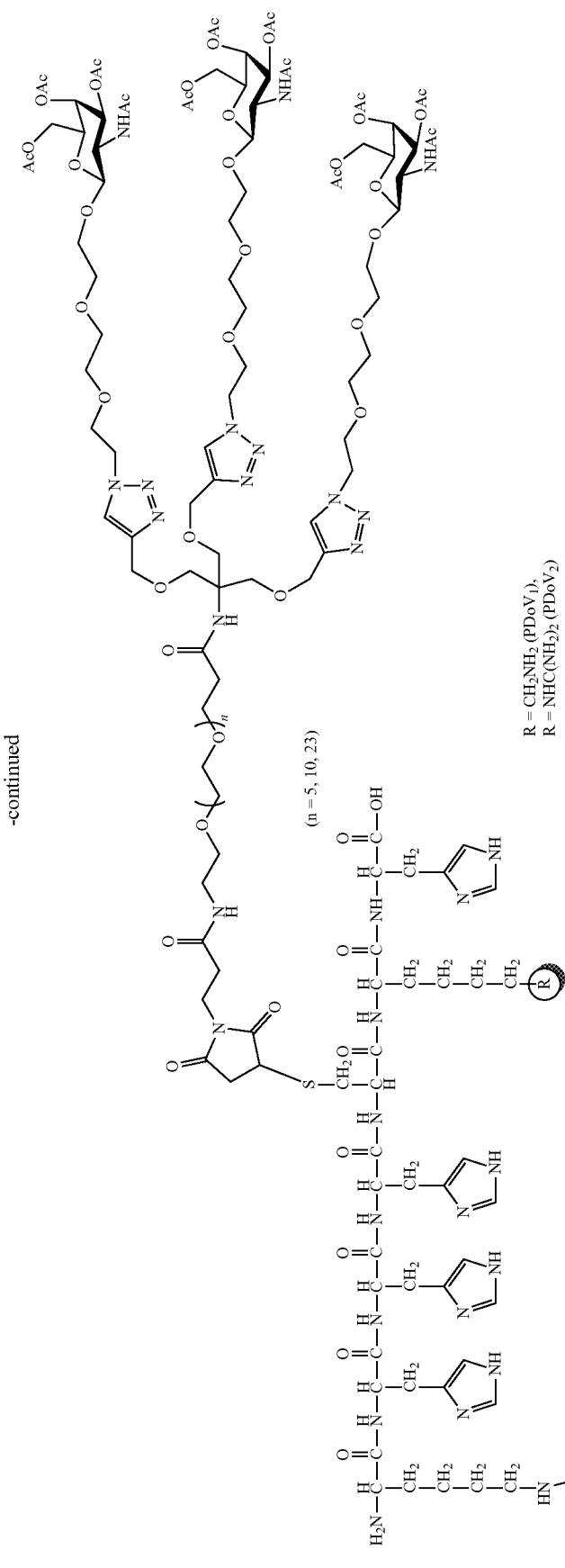
R = CH$_2$NH$_2$ (PDoV$_1$),
R = NHC(NH$_2$)$_2$ (PDoV$_2$)
(n = 5, 10, 23)
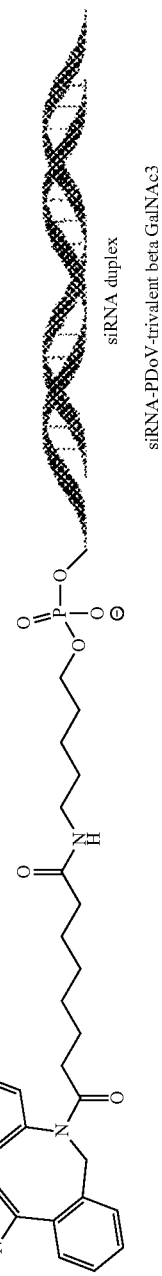
siRNA duplex
siRNA-PDoV-trivalent beta GalNAc3

Example 2
Schematic Representative Example of Construction of the siRNA-PDoV-Ligand Compound.
Step 1. Peptide Azido Modification.
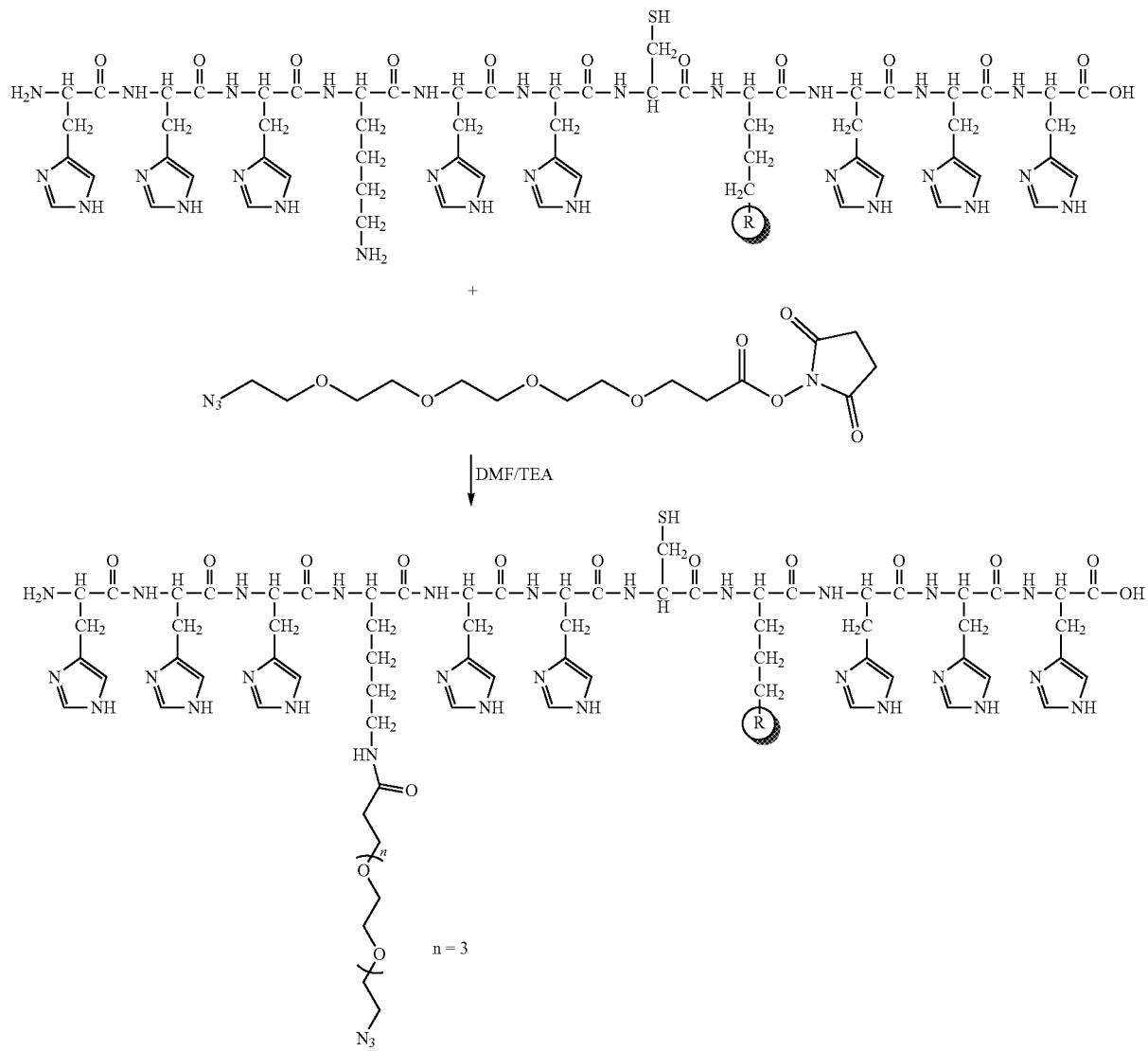
Step 2. Conjugation of Targeting Ligand with the Peptide.

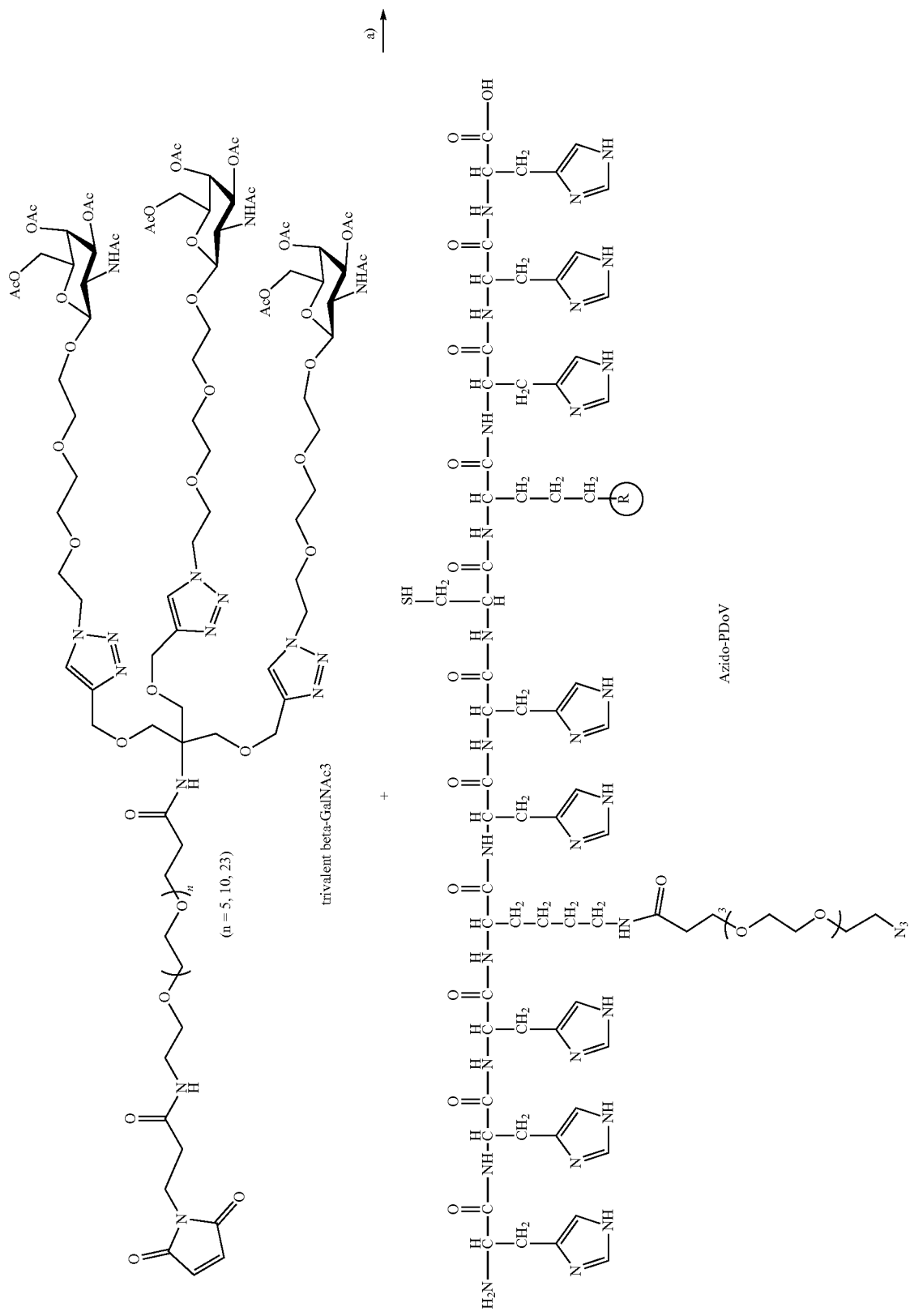

-continued
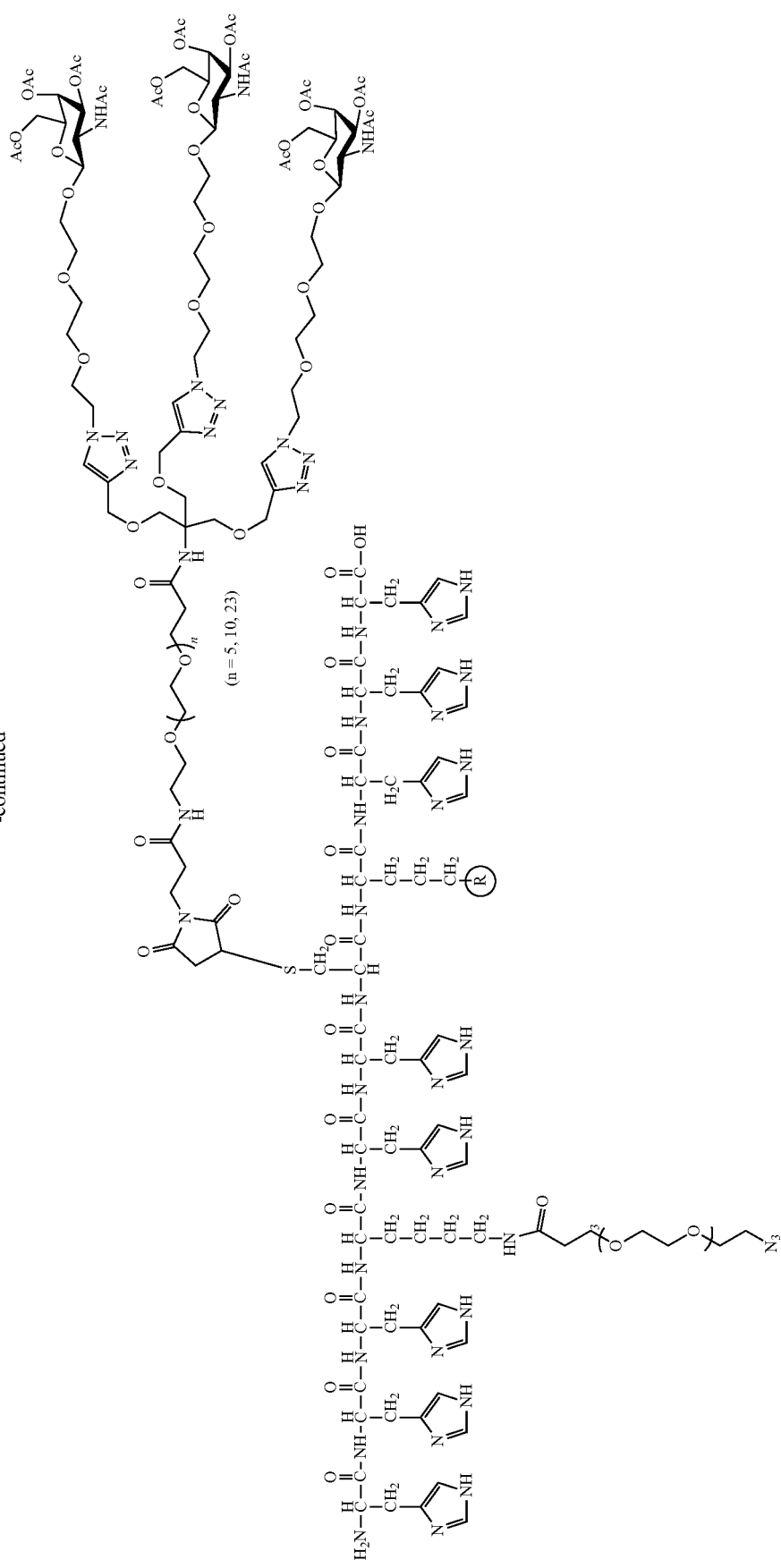
Azido-PDoV-trivalent beta GalNAc3

Step 3 and Step 4. Oligonucleotide Conjugation with the Azido-PDoV-GalNAc3
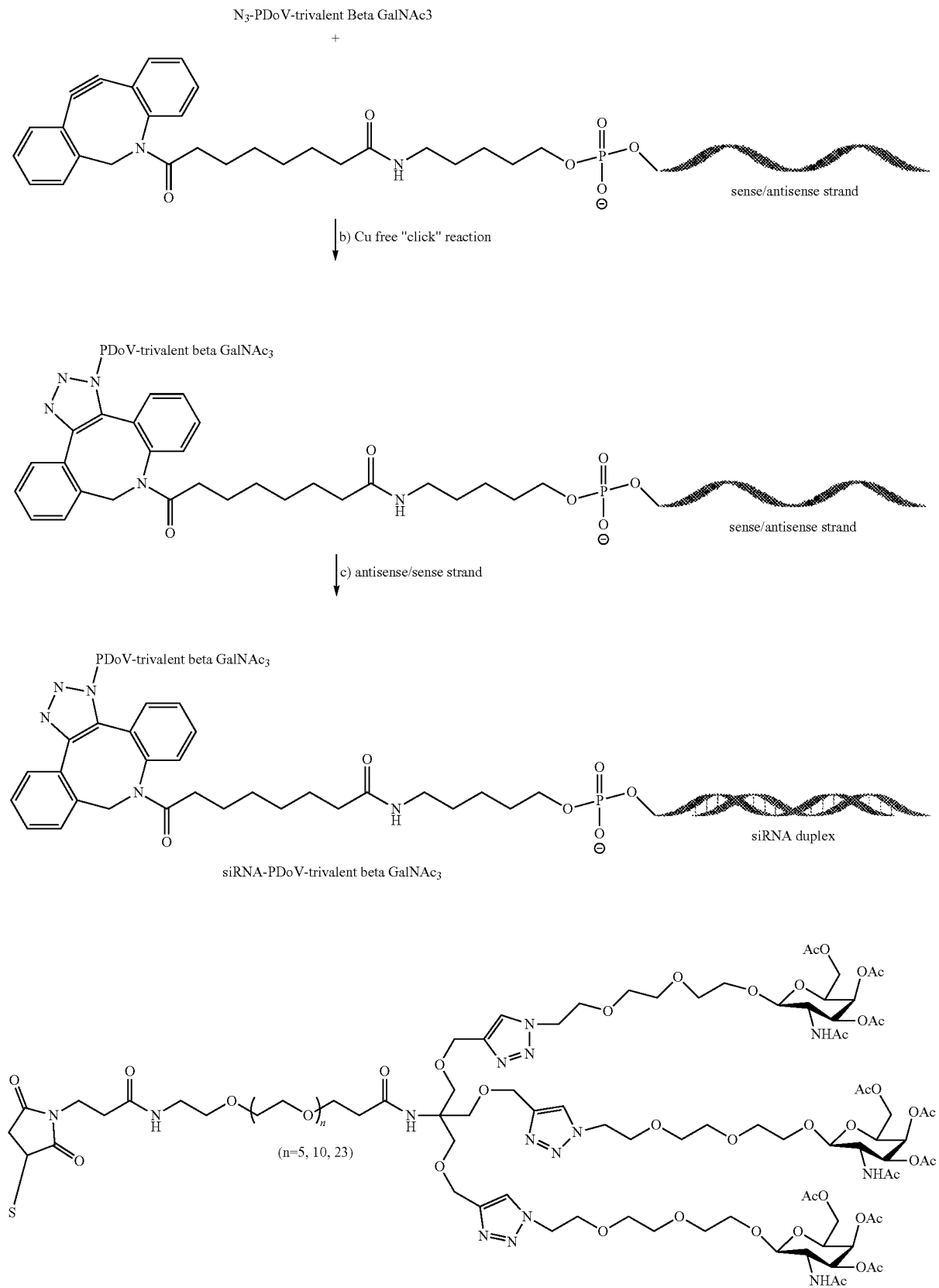

-continued

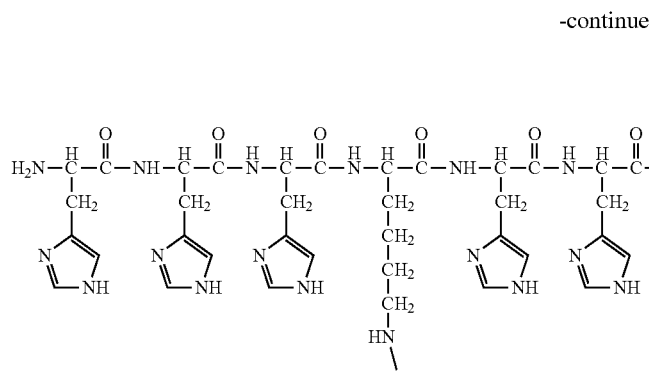
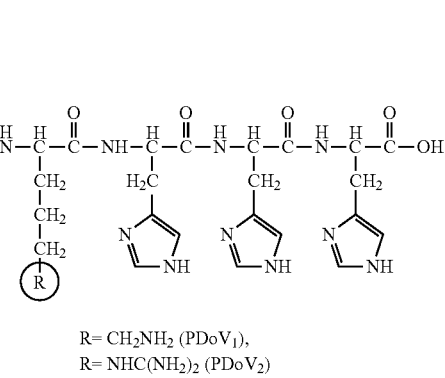

R= CH$_2$NH$_2$ (PDoV$_1$),
R= NHC(NH$_2$)$_2$ (PDoV$_2$)

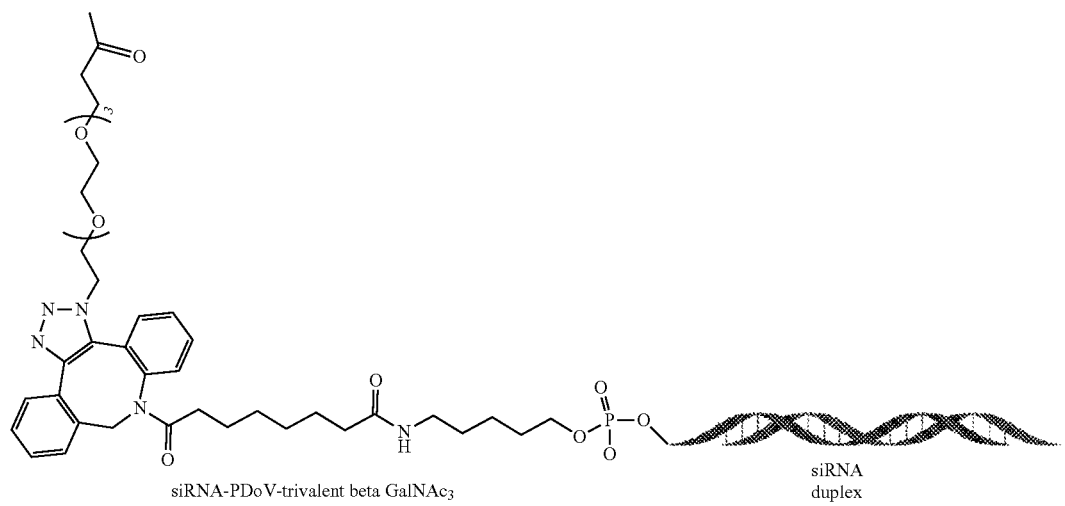

siRNA-PDoV-trivalent beta GalNAc$_3$ siRNA duplex

Example 3

Synthesis and Characterization of Azido-PDoV1 (1)

Peptide Azido-PDoV1 (sequence HHH{LYS(PEG4-N3)}HHCKHHH (SEQ ID NO: 60)) was synthesized by the automated peptide synthesizer by contracted service and using standard amino acids and lysine-PEG4-N3 modifier in the sequence. The peptide was purified by C-18 reverse phase HPLC and characterized by mass spectrometry and $^1$H NMR. The analytical data were all consistent with the expected structure.

Example 4

Synthesis of PDoV2 and Azido-PDoV2

Synthesis of PDoV2 (2), sequence HHHKHHCRHHH (SEQ ID NO: 8). Peptide PDoV2 (HHHKHHCRHHH (SEQ ID NO: 8)) was synthesized by the automated peptide synthesizer by contracted service and using standard amino acids in the sequence. The peptide was purified by C-18 reverse phase HPLC and characterized by mass spectrometry. The analytical data were all consistent with the expected structure.

Synthesis of Azido-PDoV2 (3) (Image discloses SEQ ID NO: 8)

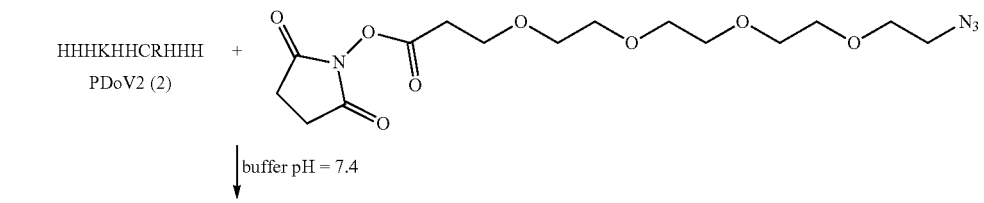

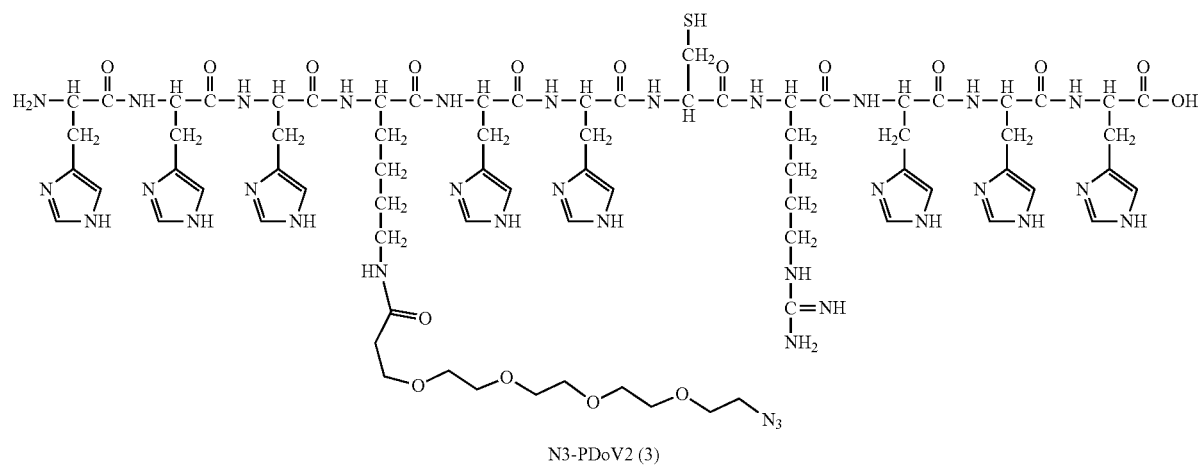

N3-PDoV2 (3)

The azide linker was attached to the Peptide Docking Vehicle 2 (PDoV2) via amide bond formation between the ester activated carboxylic acid of the azide linker and the primary amine of the Lysine side chain of PDoV2 (2) to form compound 3. PDoV2 peptide HHHKHHCRHHH (SEQ ID NO: 8) (42 mg, 0.0280 mmol) was suspended in 1.0 mL DMF. Triethyl amine (39 uL, 10 eq) was added and the mixture was stirred at room temperature for 20 minutes. A solution of Azido-Peg4-NHS ester (54 mg, 0.140 mmol, 5 eq) in 20 uL of DMF was added to the reaction mixture. The reaction mixture slowly turned into a clear solution over 30 minutes and was stirred further at room temperature for 16 hours. The TLC profile of the reaction mixture was monitored by HPLC profile of full complete conversion of PDoV2 (FIG. 1).

The reaction mixture was quenched with water (200 μL), concentrated using a rotary evaporator and the crude material was purified through HPLC on semi-prep RP-C18 column using an increasing gradient of 10-90% of Buffer B (0.1% TFA in Acetonitrile). Azido-PDoV2 (2) was isolated as the major product with a retention time between 10.5 and 11.5 minutes. Sample fractions were lyophilized resulting in a clear residual oil of compound 2 (44 mg, 88% yield). Its proton and MS analysis were as follows: $^1$H NMR (400 MHz, D2O, FIG. 2) δ 8.74 (brd d, 8H) and δ 7.35 (brd d, 8H) are consistent with aromatic hydrogens associated with 8 histidine tetrazoles in the peptide above δ 6.00 ppm. Methine hydrogens at the alpha carbon of all the 11 amino acids at δ 4.75-4.30 (brd t, 11H), ethylene hydrogens associated with polyethylene group at δ 3.90-3.75 (m, 100H); δ 3.6-2.75 (m, 53H) and δ 1.8-1.3 (m, 12H) ethylene hydrogens associated with the side chain protons of Lysine, arginine and cysteine. In total, 104 hydrogens are observed in the non aromatic regions and are in excess by 41 hydrogens. These extra hydrogens are the equivalent of 2 Azido-peg4 groups. The NMR data is consistent with ESI-MS data: expected m/z 1775.9 Da and the observed m/z 2323.5 Da (FIG. 3). The observed mass to charge ratio is 547.6 Da units more than the expected value. The extra mass units are consistent with mass of two Azide-linkers.

Example 5

Synthesis and Characterization of Azido-PDoV3 Peptide (4)

Peptide Azido-PDoV3 ({LYS(PEG4-N3)}HHHCHH (SEQ ID NO: 36)) was synthesized using solid-phase automated synthesis using standard amino acids plus lysine-PEG4-N3 modifier in the sequence. The peptide was purified by C-18 reverse phase HPLC and characterized by H$^1$NMR and mass spectrometry. The analytical data were all consistent with the expected structure.

Example 6

Synthesis and Characterization of PDoV1-GalNAc3 (5). (Image Discloses SEQ ID NOS 60 and 55, Respectively, in Order of Appearance)

After the solvent was removed under reduced pressure, the sample was desalted and purified by PD-10 column to provide the pure product PDoV1-GalNAc3 5 (5.1 mg, white solid, yield 90%). The product was analyzed by HPLC using a reverse phase C18 column, gradient elution by solvent

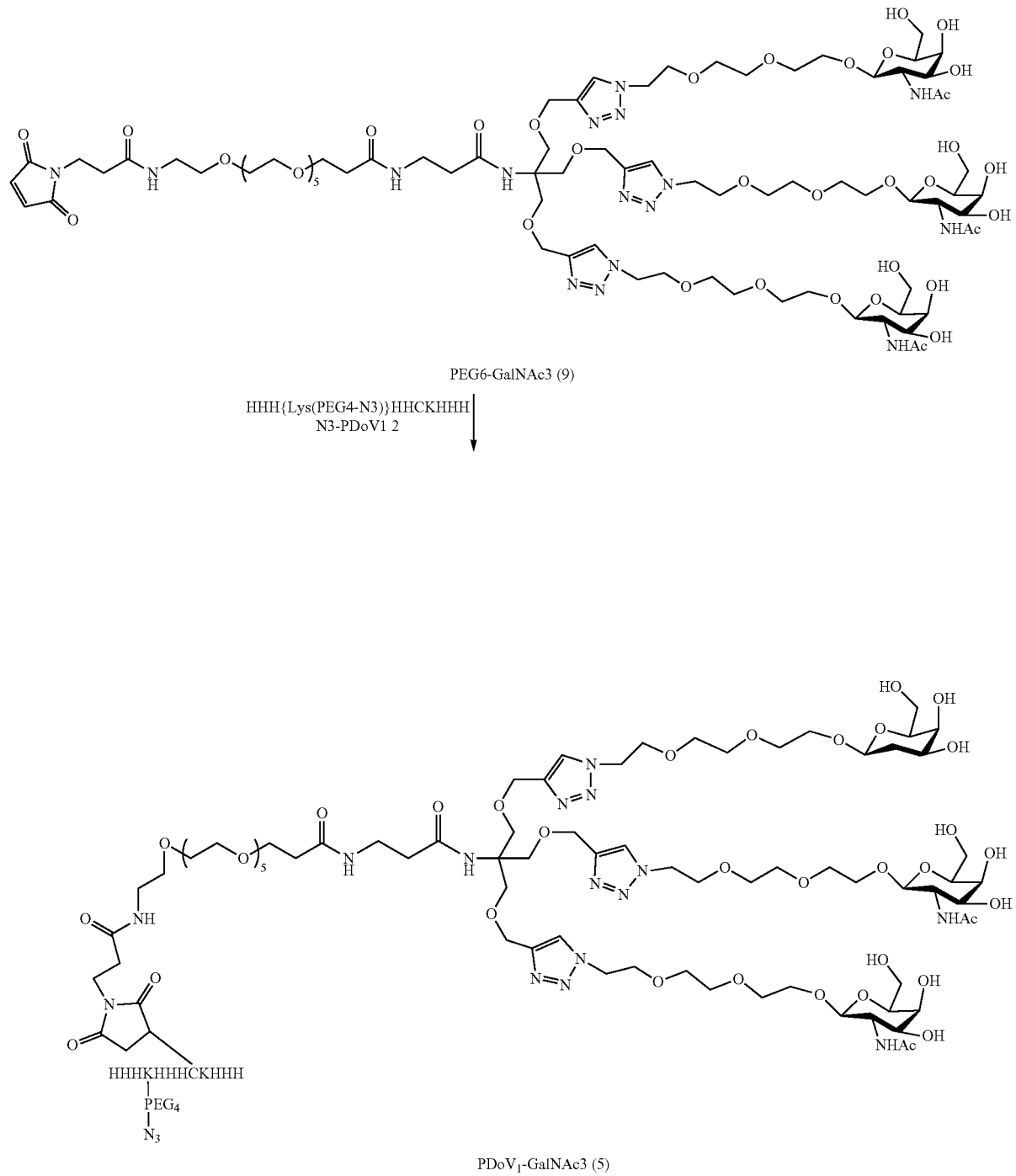

PEG6-GalNAc3 (9) (3.0 mg, 1.56 μmol) in dry DMF (400 uL) was added to the solution of N3-PDoV1 2 (3.54 mg, 2.03 μmol) in phosphate buffer (1 mL, pH=7.4). The resulting mixture was stirred at 25° C. under nitrogen overnight. 0.1% TFA water and 0.1% acetonitrile. Retention time Rt=4.877 min, purity >90%. Mass spectrum analysis (ESI, positive): Calc. for C154H240N48O55S 3673.7 found 3674.8.

Example 7

Synthesis and Characterization of PDoV2-GalNAc3 6 and 7

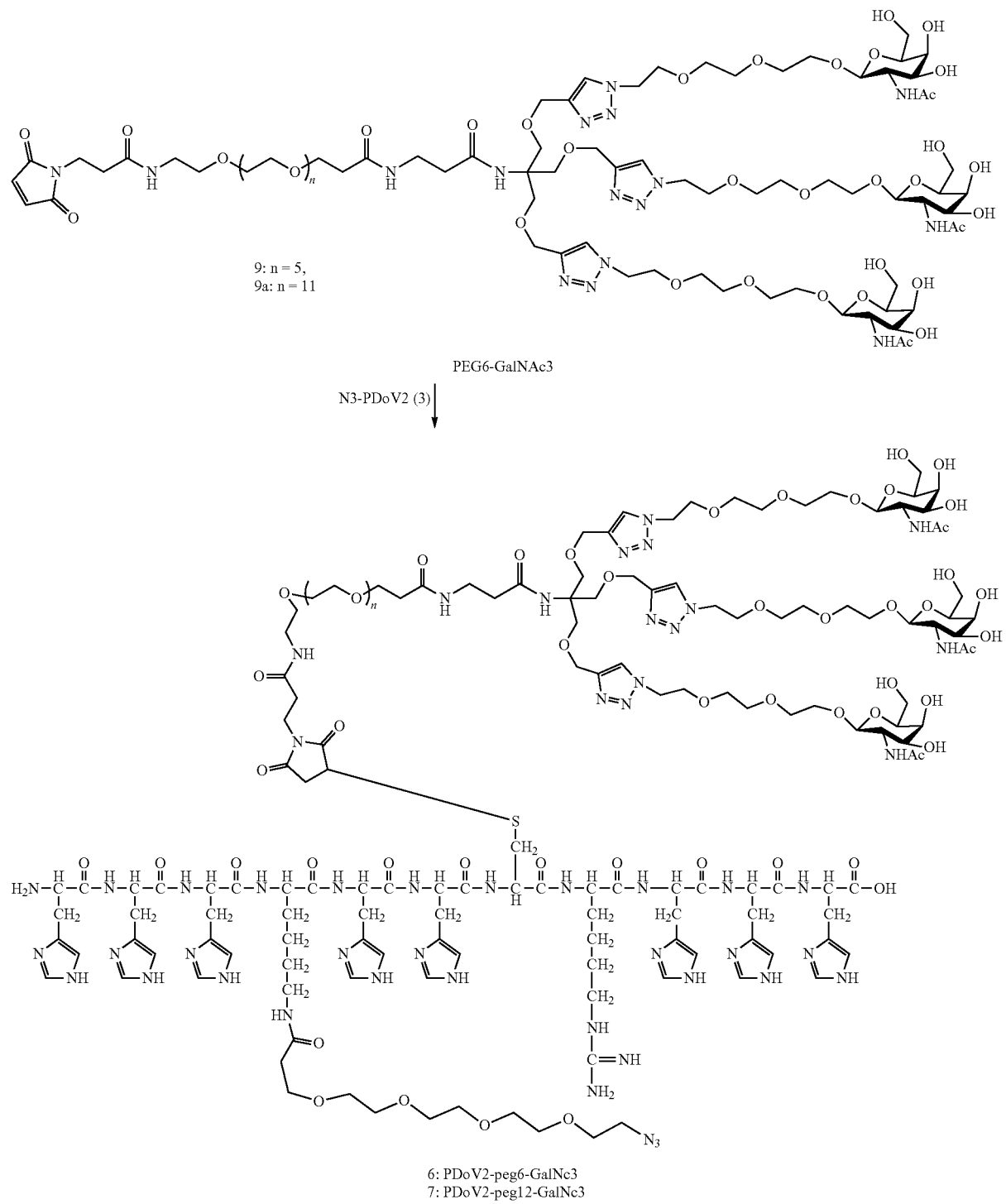

Scheme 2: Preparation of PDoV2-linker-GalNAc3.

6: PDoV2-peg6-GalNc3
7: PDoV2-peg12-GalNc3

Figure 7:
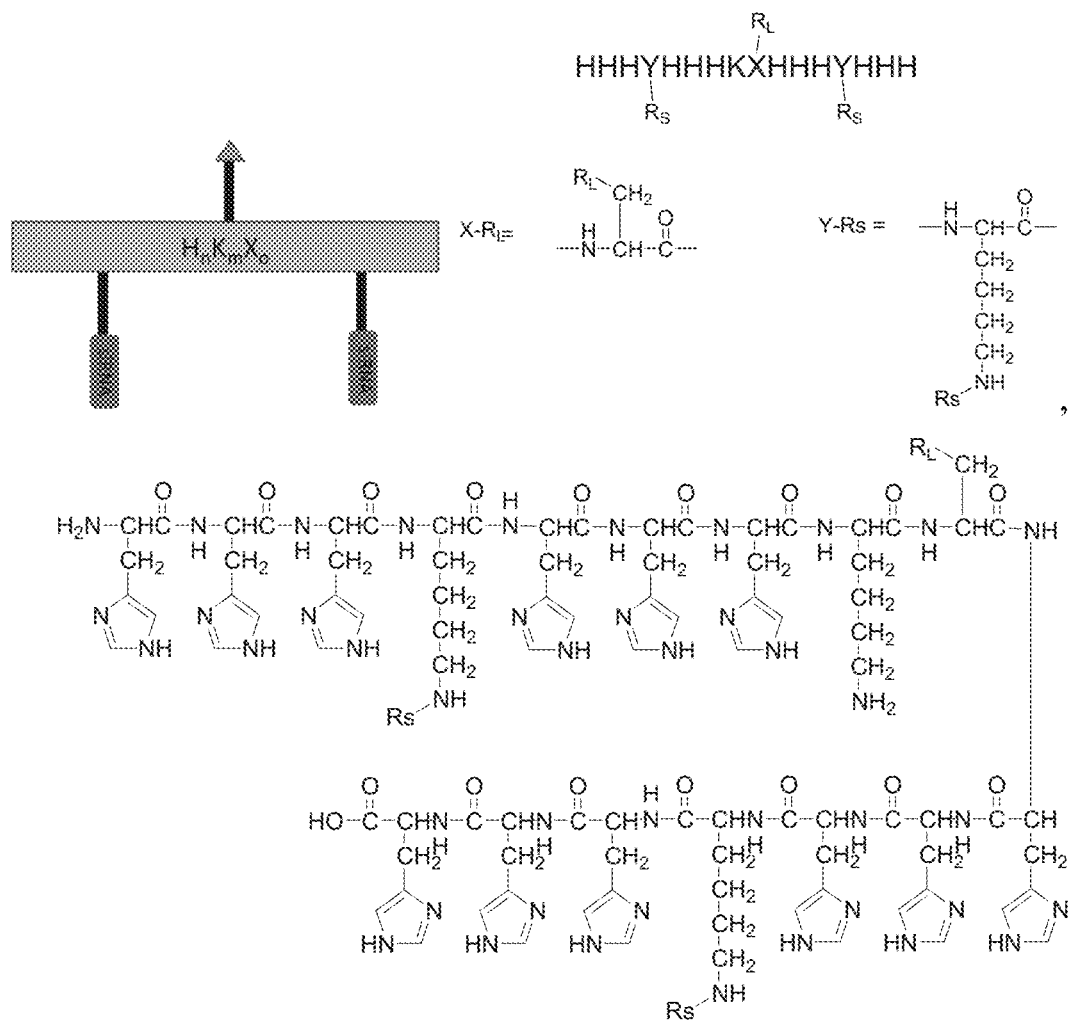
FIG. 7 shows an example of the structure of a second generation PDoV, containing two oligonucleotide sites and one multivalent ligand conjugation site. Figure discloses SEQ ID NO: 58.
Figure 8:
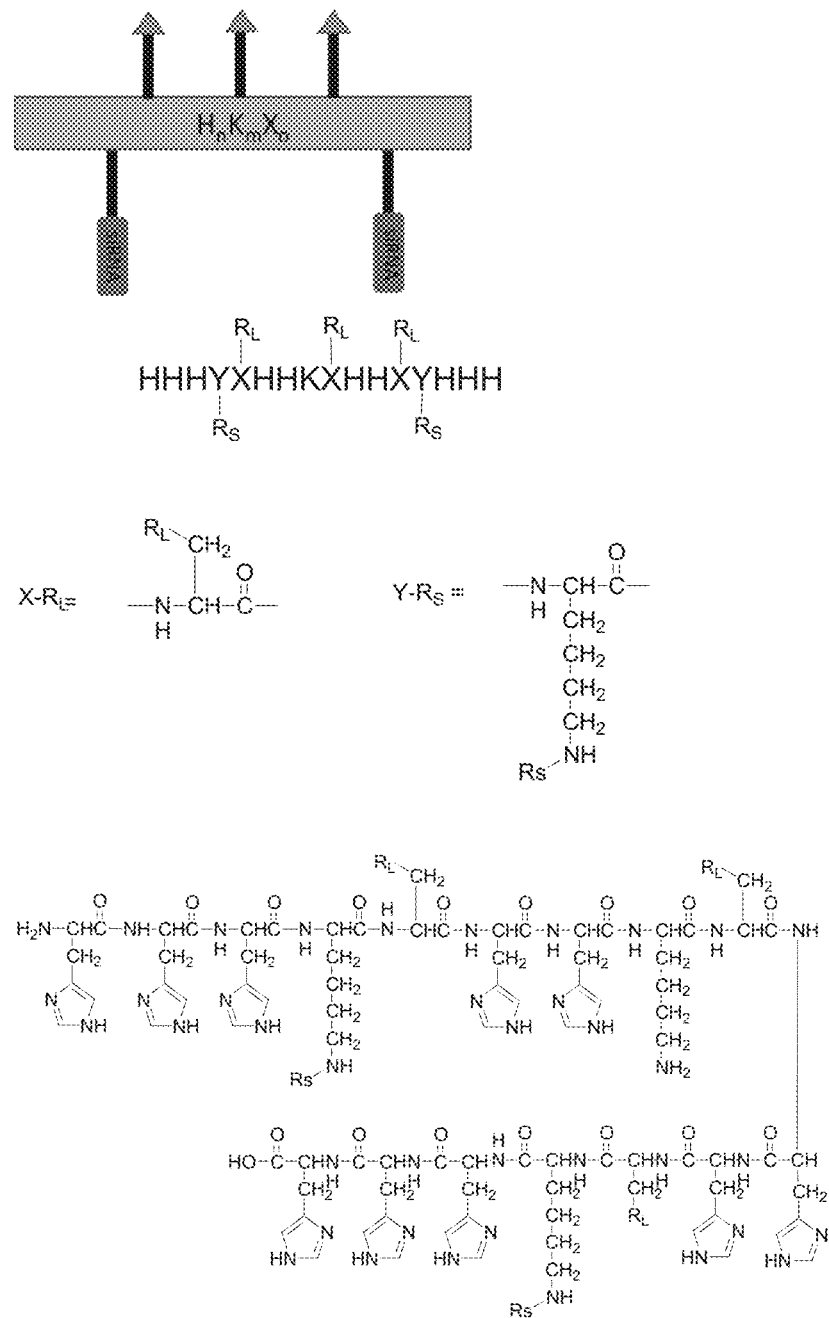
FIG. 8 shows an example of alternative structure of a PDoV, containing two oligonucleotide sites and one multivalent ligand conjugation site. The ligands can be conjugated individually one by one on the PDoV backbone. Figure discloses SEQ ID NO: 54.

Preparation of PDoV2-Peg6-GalNAc3 (compound 6): The nucleophile, Compound 2 (49.8 mg, 0.0243 mmol) was dissolved in 1.0 mL of degassed PBS buffer at pH 7.4. Trivalent GalNAc-ligand (9) (30.8 mg, 0.0160 mmol) was dissolved and delivered in 400 uL of dry DMF. The reaction mixture was again degassed under dry argon and allowed to stir at room temperature overnight. The reaction mixture was quenched with water (100 μL) and desalted through 1.0 μmol Sephadex Nap column following the Glen Research recommended protocols. The eluent was lyophilized, and the crude material was eluted on HPLC through a semi-prep C18 reverse phase column with increasing gradient of 10-90% of Buffer B (0.1% TFA in Acetonitrile and water (FIG. 7). The product had a retention time of 4.0 mins and was isolated as an oil (39 mg, 60% yield). The mass spec of the modified oligos confirmed that synthesis of the PDoV2-peg6-GalNAc3 construct was successful.

Figure 4:
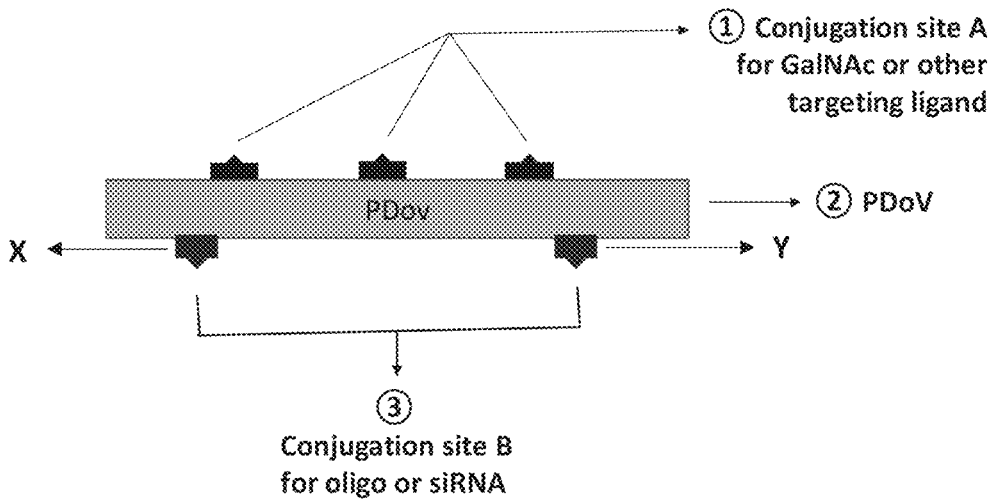
FIG. 4 shows the design of a Peptide Docking Vehicle (PDoV) with three ligand conjugation sites and multi oligonucleotide sites: it has a $(H_nK_m)_oX_pY_q$ peptide backbone with multi-repeating units of histidine (H), lysine (K) and functional units X and Y (amino acid, or functional linker), wherein the n=1-10, m=1-10, o=1-10, p=1-5, q=1-5 (SEQ ID NO: 35). HK repeating units have been demonstrated to have good cell penetrating ability and to facilitate endosome release. The lysine residues or the various functional units X are adapted as the docking sites for conjugation of ligands, and Y is adapted as the docking site(s) for the conjugation of oligonucleotides through different covalent linkages. For example, the site ① will only be able to react in the presence of a ligand such as GalNAc or other targeting ligands. The site ③ can only conjugate with oligonucleotides and siRNAs under specific conditions.

Preparation of PDoV2-Peg12-GalNAc3 (compound 7): Compound 7 azido-PDoV2 (4.9 mg, 2.74 μmol) was dissolved in 1.0 mL of degassed PBS buffer at pH 7.4. GalNAc-ligand (3.0 mg, 1.37 μmol) was dissolved and delivered in 400 uL of dry DMF. The reaction mixture was again degassed under dry nitrogen and allowed to stir at room temperature overnight. The reaction mixture was quenched with water (100 μL) and desalted through 1.0 umol Sephadex Nap column following the Glen Research recommended protocols. The eluent was lyophilized, and the crude material was eluted on HPLC through a semi-prep C18 reverse phase column with increasing gradient of 10-90% of Buffer B (0.1% TFA in Acetonitrile and water (FIG. 4). The product was exclusively formed as a major product with a retention time at 4.2 minute and was isolated as a white powder (4.4 mg, 81% yield). Proton NMR and MS analysis: H NMR (400 MHz, $D_2O$,) δ 7.94 (s, 3H, triazoles), δ 8.57-δ 7.19 (m, 18H, 8 histidine aromatic), δ 4.75-4.30 (m, 14H, amino acids), δ 4.5 (d, 3H, galactose), δ 2.05 (s, 9H) The NMR data is consistent with ESI-MS data. ESI-MS (positive mode, m/z) Calc. 3968.2 for $C_{168}H_{268}N_{50}O_{61}S$, observed 3968.2.

Example 8

Synthesis of PDoV3-GalNAc3 (8). (Image Discloses SEQ ID NO: 36)

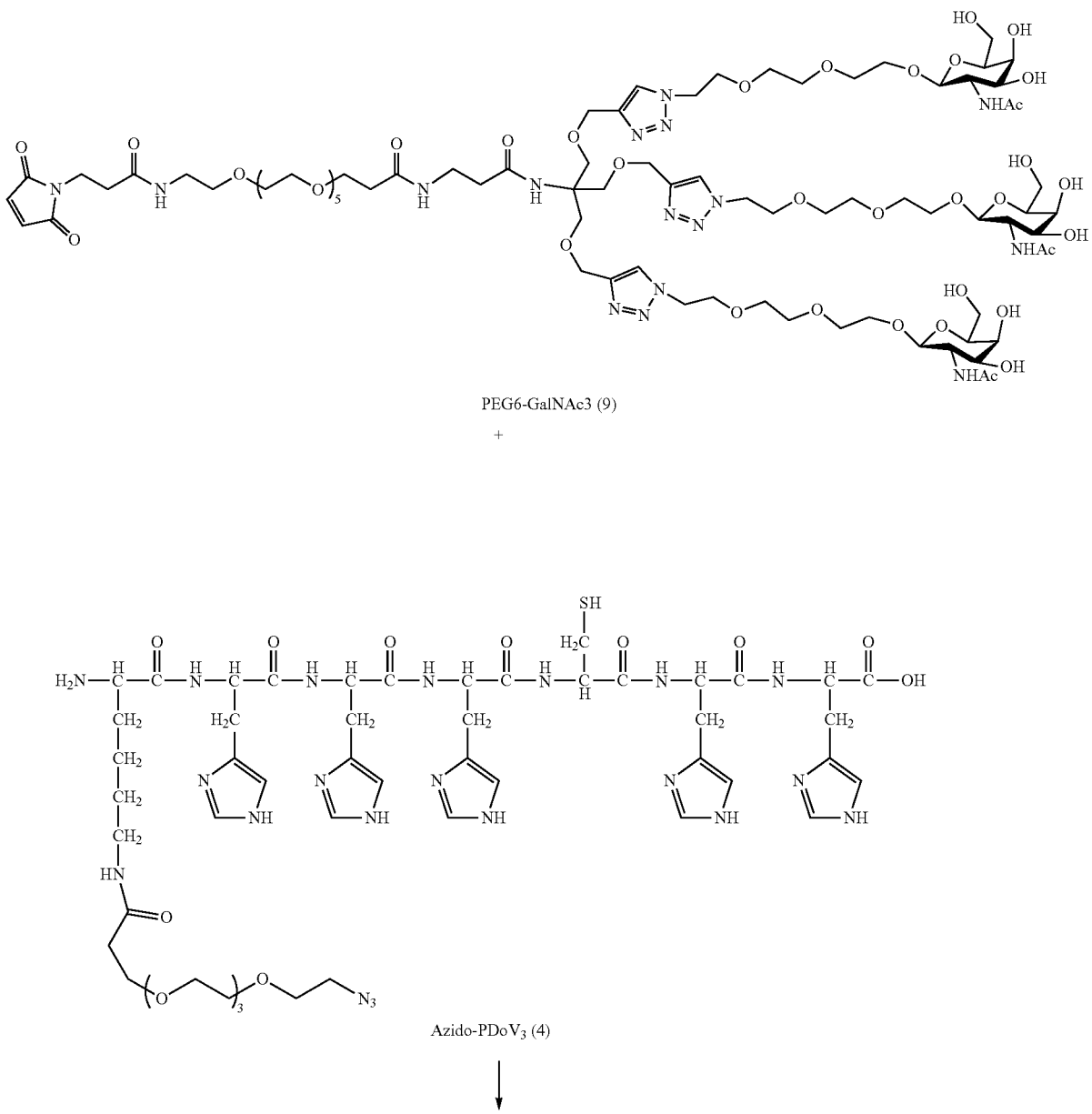

-continued

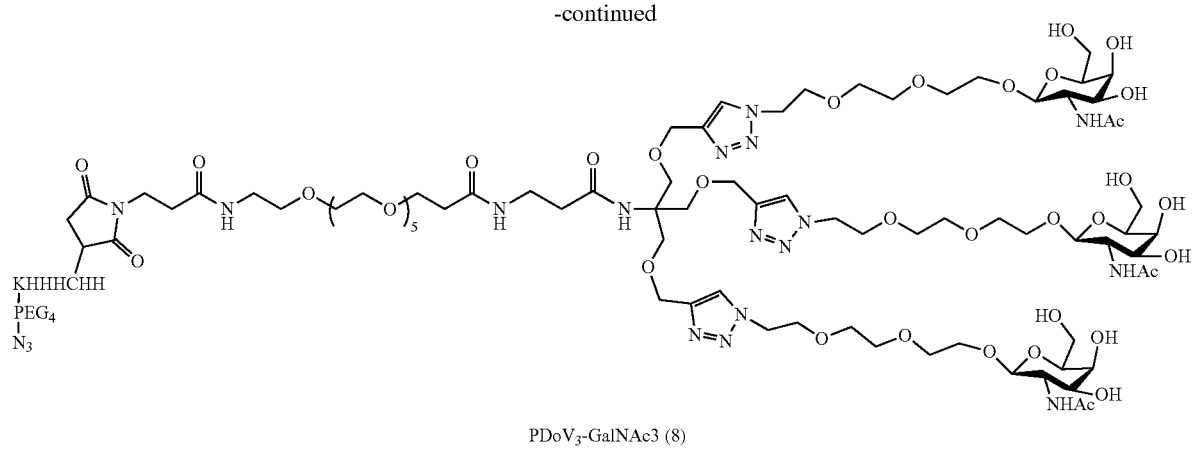

PDoV₃-GalNAc3 (8)

Synthesis of PDoV3-GalNAc3 (compound 8): Azido-PDoV3 compound 4 (47.0 mg, 38.9 µmol) in DMF (1.5 mL) was added to the mixture of trivalent GalNAc (9) (50.0 mg, 25.9 µmol) in phosphate buffer (4 mL, pH 7.4) under nitrogen at 25° C. The resultant reaction mixture was stirred at 25° C. for 12 hours. The reaction was monitored by HPLC until GalNAc 9 was fully consumed. The solvent was removed by lyophilization and the crude material was purified by gel permeation column chromatograph PD-10 column to provide the pure product PDoV3-GalNAc3 compound 8 (70 mg, yield 86.4%). The HPLC was performed on reverse phase C-18 column by gradient elution of solvent 0.1% TFA in water and 0.1% TFA in acetonitrile Rt=5.038 min. MS (ESI, positive mode) Exact Mass: 3134.45 for Formula: $C_{130}H_{207}N_{37}O_{51}S$. Found: 3136.35. The analytical data were all consistent with the expected structure.

Example 9

Synthesis of Control 3-GalNAc3 (11). (Image Discloses SEQ ID NO: 37)

Scheme 4: Synthesis of Control3-GalNAc3 (11).

PEG6-GalNAc3 (9)

+

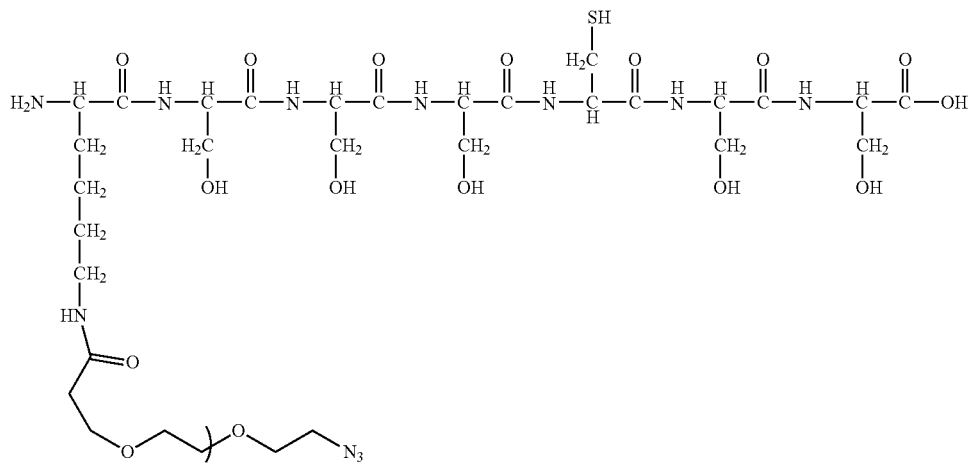

Azido-PDoV₃ (10)

↓

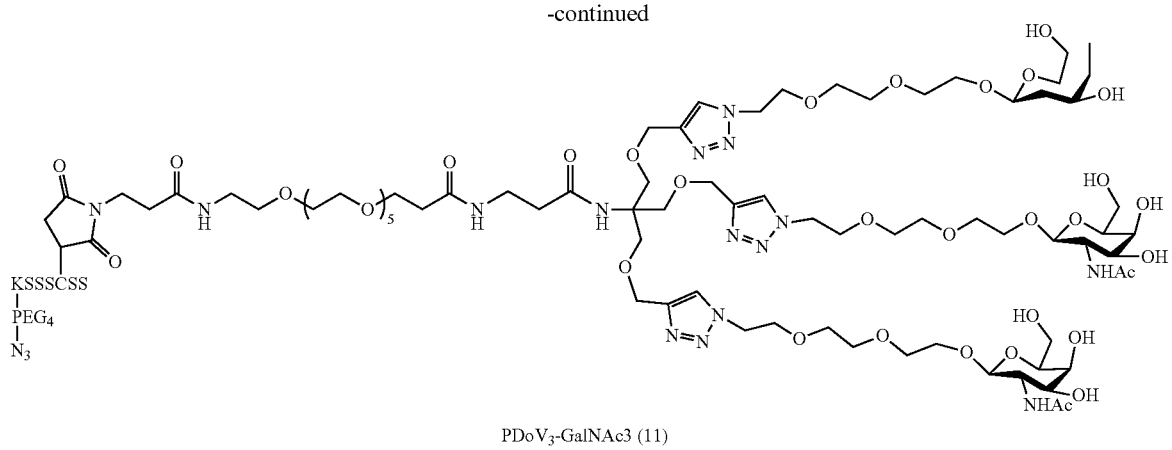

PDoV₃-GalNAc3 (11)

Preparation of PDoV3-control3-GalNAc3:

Compound azido-control3 peptide 11 (sequence {LYS (PEG4-N3)}SSSCSS (SEQ ID NO: 37)) (2.6 mg, 2.59 μmol) was dissolved in 1.0 mL of degassed PBS buffer at pH 7.4. GalNAc-ligand (5.0 mg, 2.59 μmol) was dissolved and delivered in 500 uL of dry DMF. The reaction mixture was again degassed under dry argon and allowed to stir at room temperature overnight. The reaction mixture was quenched with water (100 μL) and desalted through 1.0 μmol Sephadex Nap column. Several eluent fractions were collected and lyophilized to afford the desired compound Control3-GalNAc3 10. This compound was analyzed using analytical HPLC C18 RP column with increasing gradient of 10-90% of Buffer B (0.1% TFA in Acetonitrile and water. The product had a retention time of 3.80 min and was isolated as a clear oil (4.9 mg, 67% yield). The mass spectrum of the modified oligonucleotides confirmed the structure of the PDoV3-Control3-peg6-GalNAc construct.

Example 10

Synthesis and Characterization of ApoB100-PDoV1-GalNAc3 (12). (Image Discloses SEQ ID NOS 51, 56, 51, and 38, Respectively, in Order of Appearance)

Scheme 5. Synthesis of ApoB100-PDoV1-GalNAc3 (12).

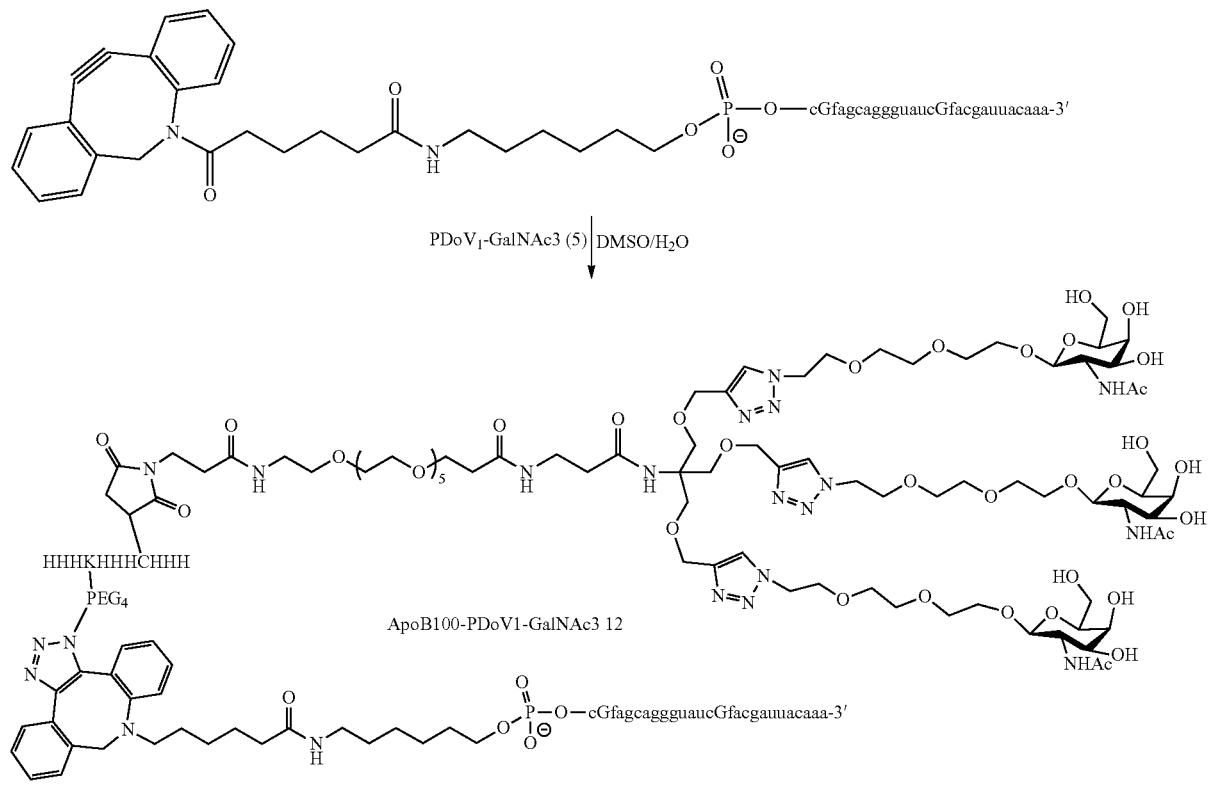

ApoB100-PDoV1-GalNAc3 12

ApoB100 sense (5' end DBCO modification)
Antisense- 5'-uuuGfTaaugucgauAfcccugcucg-3'
Lower case x = 2'-OMe, upper case X = normal nueleotide, Xf = 2'-F PDoV1-GalNAc3 5 (381 μg, 0.104 μmol) in DMF (95 μL) was added to a solution of ApoB100-sense-5'-DBCO (500 ug, 0.069 μmol) in RNAse free water (250 μL). The resultant mixture was stirred at 25° C. for 2 hours. After solvent was removed under reduced pressure, the crude material was purified by Glen Gel PaK column chromatograph to provide the pure product sense ApoB100-PDoV3-GalNAc3 compound 12 (0.66 mg, yield 88%). The HPLC was performed on PA200 ion exchange column using phosphate buffer at pH=11, Rt=13.015 min., purity >85%. MS (ESI, positive mode) Calc. 10911.66 for Formula: $C_{388}H_{510}N_{125}O_{208}P_{22}S$. Found: 10929.3 [M+H2O]. After performing the 1:1 annealing (95° C. for 5 min, cool down by around 1° C./min to room temperature, then store under −20° C.) with the ApoB100 antisense strand it provided the final conjugate duplex ApoB100-PDoV1-GalNAc3 (12). The dye Alex-647 labeled ApoB100-PDoV1-GalNAc3 was prepared by replacing the ApoB100 antisense with the dye labeled antisense ApoB100-Alexa647 (5'-uuuGfTaaucgucgauAfcccugcucg-Alexia647-3' (SEQ ID NO: 38)). The product was characterized by HPLC and MS. The analytical data were all consistent with the expected structure.

Example 11

Synthesis and Characterization of ApoB100-PDoV2-GalNAc3

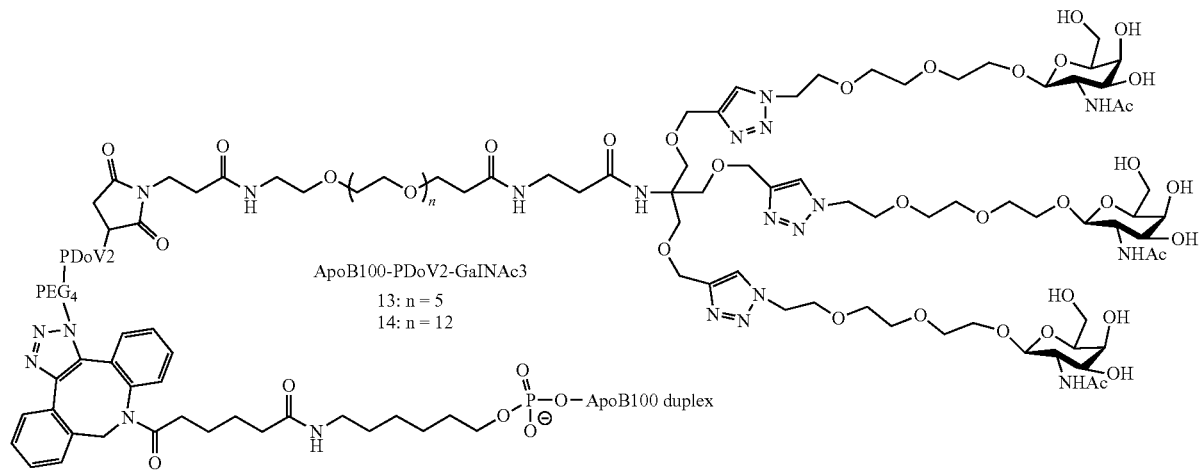

ApoB100-PDoV2-GalNAc3 13 was prepared by the similar method as for ApoB100-PDoV1-GalNAc3 12 by reacting PDoV2-GalNAc (6, or 7, 0.0341 μmol, 1.5 equiv.) and APOB100-SS-5'C6NHS(DBCO) (0.0227 μmol). The azido-PDoV2-GalNAc was first dissolved in DMSO in the ratio of 1 mg of azide per 150 μL of DMSO. The resultant azide solution was then added to 10 OD of 5'-DBCO labeled oligo in 100 μL of RNAse free water. The reaction solution mixture was then incubated at room temperature for 3-4 hours. The conjugated oligo was then desalted on a Glen Gel-Pak™ desalting column to remove organic solvent and any unconjugated peptide. Taken as an example, when PDoV2-PEG12-GalNAc 7 was the reactant, the final ApoB100-PDoV2-GalNAc3 14 was provided as a white solid in 77% yield. The HPLC was performed on PA200 ion exchange column using phosphate buffer at pH=11, Rt=12.077 min., purity >85%. MS (ESI, positive mode) Calc. Cal. 11551.4, Found: 11553.5. 1:1 annealing (95° C. for 5 min, cool down by around 1° C./min to room temperature, then store at −20° C.) with the antisense provided the final conjugate duplex ApoB100-PDoV2-GalNAc3 (14).

The dye Alexa-647 labeled ApoB100-PDoV1-GalNAc3 was prepared by replacing the ApoB100 antisense with the dye labeled antisense ApoB100-Alexa647 (5'-uuuGfTaaucgucgauAfcccugcucg-Alexia647-3' (SEQ ID NO: 38)). The product was characterized by HPLC and MS. The analytical data were all consistent with the expected structure.

Example 12

Synthesis and Characterization of ApoB100-PDoV3-GalNAc3 15. (Image Discloses SEQ ID NOS 51, 36, 51, and 38, Respectively, in Order of Appearance)

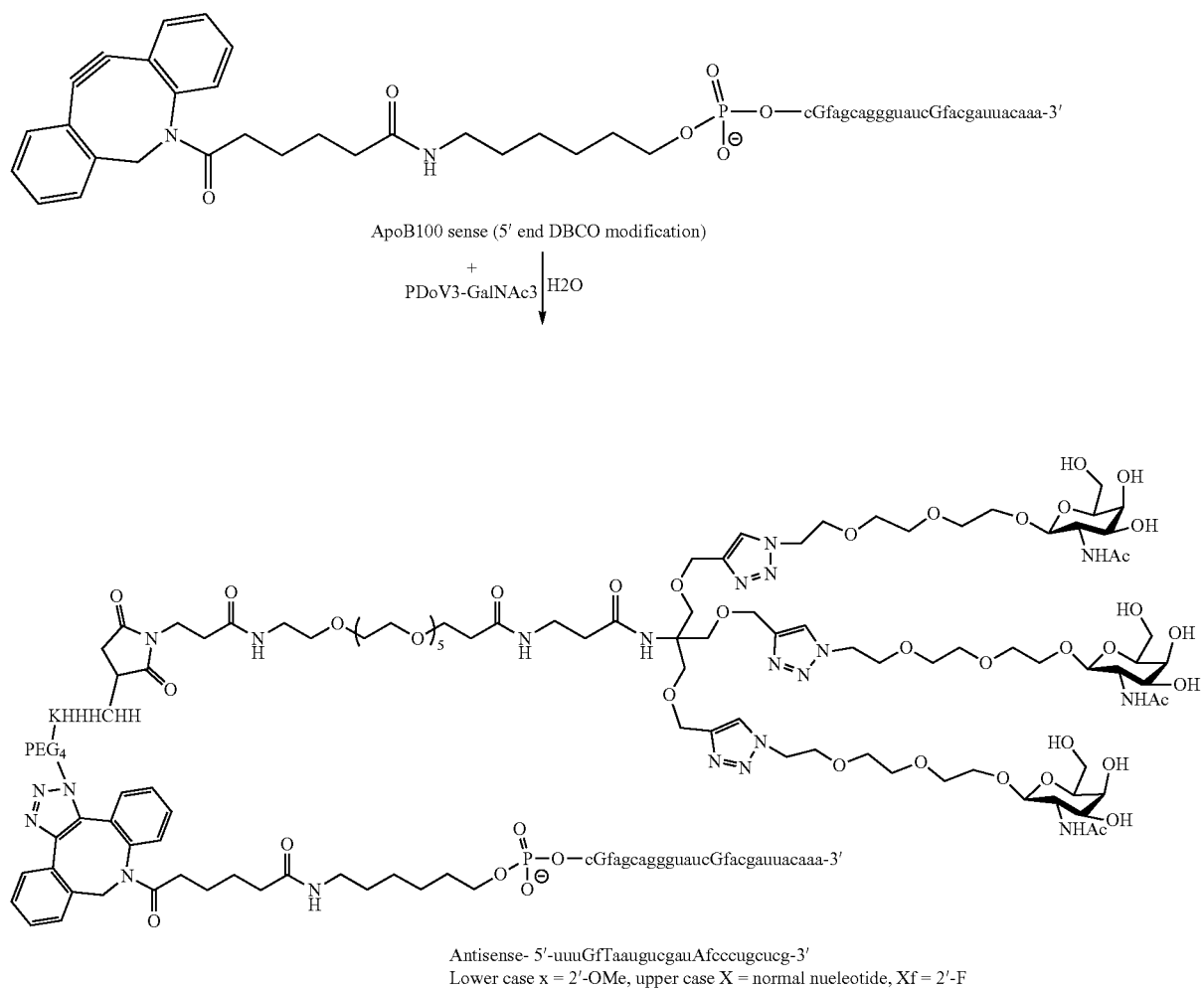

PDoV3-GalNAc3 8 (150 µg, 0.148 µmol) was added to the solution of 5'-DBCO-C6HN-APOB100 sense strand (230.7 µg, 0.0319 µmol) in RNAse free water (200 µL). The mixture was stirred at 25° C. for 3 hours. After solvent was removed by lyophilization, the crude material was purified by Glen Gel Pak column to provide the pure product sense ApoB100-PDoV3-GalNAc3 compound 15 (298 µg, yield 90%). The HPLC was performed on PA200 ion exchange column using phosphate buffer at pH=11, Rt=12.002 min., purity >89%. 1:1 annealing (95° C. for 5 min, cool down by around 1° C./min to room temperature, then store under −20° C.) with the antisense provided the final conjugate duplex ApoB100-PDoV3-GalNAc3. The dye Alexa-647 labeled ApoB100-PDoV1-GalNAc3 was prepared by replacing the ApoB100 antisense with the dye labeled antisense ApoB100-Alexa647 (5'-uuuGfTaaucgucgauAfcccug-cucg-Alexia647-3' (SEQ ID NO: 38)). The product was characterized by HPLC and MS. The analytical data were all consistent with the expected structure.

Example 13

Synthesis and Characterization of mTTR1-PDoV2-GalNAc3 (16) (Image Discloses SEQ ID NOS 47, 57, and 47-48, Respectively, in Order of Appearance)

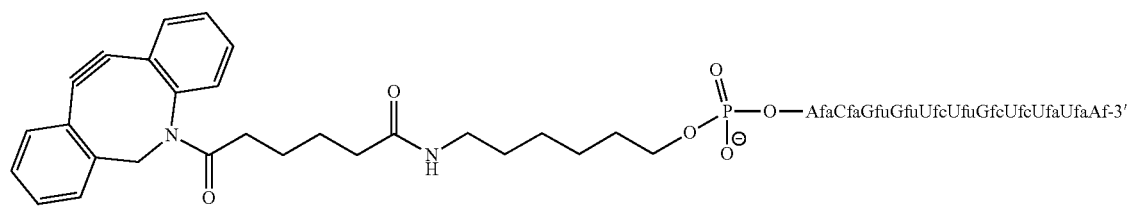

mTTR sense (5' end DBCO modification)

PDoV2-GalNAc3 (6)

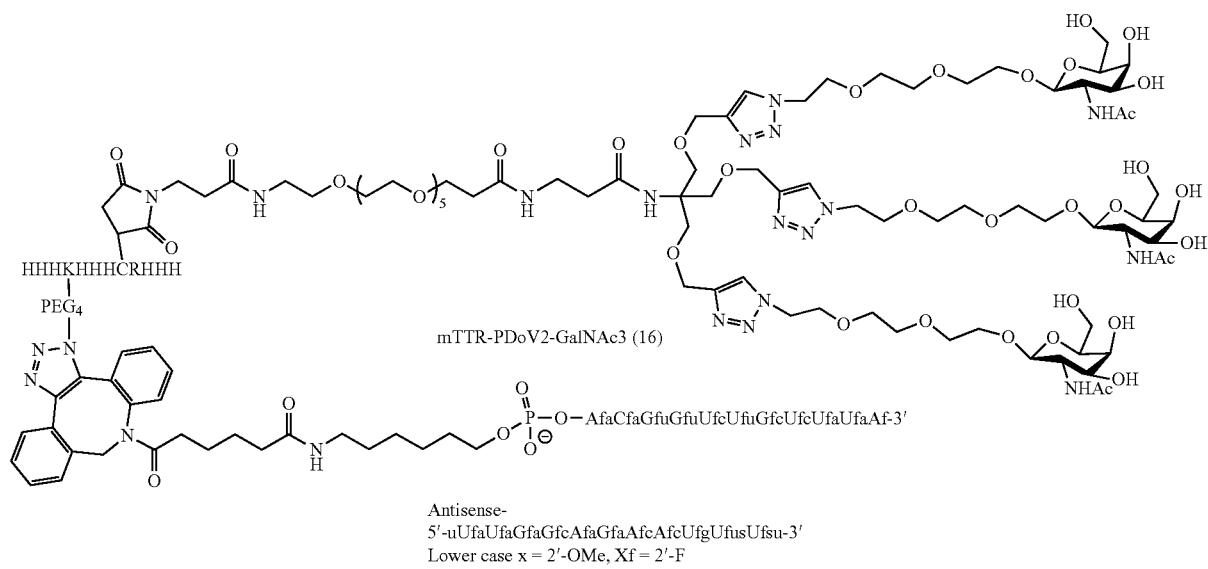

mTTR-PDoV2-GalNAc3 (16)

Antisense-
5'-uUfaUfaGfaGfcAfaGfaAfcAfcUfgUfusUfsu-3'
Lower case x = 2'-OMe, Xf = 2'-F mTTR1-PDoV2-GalNAc3 was prepared by following a similar procedure as with synthesis of mTTR1-PDoV3-GalNAc3 by using PDoV2-peg6-GalNAc 6 (0.547 mg, 0.1374 μmol) and DBCO-labeled mTTR1 sense strand (0.5 mg, 0.0687 μmol) in DMSO/water solvent. The crude material was purified by gel permeation column chromatograph G25 column to provide the pure product. The yield was about 78%. After 1:1 annealing (95° C. for 5 min, cool down by around 1° C./min to room temperature, then store under −20° C.) with the antisense strand it provided the final conjugate duplex mTTR1-PDoV2-GalNAc3 (16).

Example 14

Synthesis and Characterization of mTTR1-PDoV3-GalNAc3 17 (Image Discloses SEQ ID NOS 36, 47, 36, and 47-48, Respectively, in Order of Appearance)

solvent was removed under reduced pressure, the crude material was purified by gel permeation column chromatograph PD-10 column to provide the pure product sense mTTR1-PDoV3-GalNAc3 compound 17 (mg, yield 85%). The HPLC was performed on PA200 ion exchange column using phosphate buffer at pH=11, Rt=14.744 min., purity

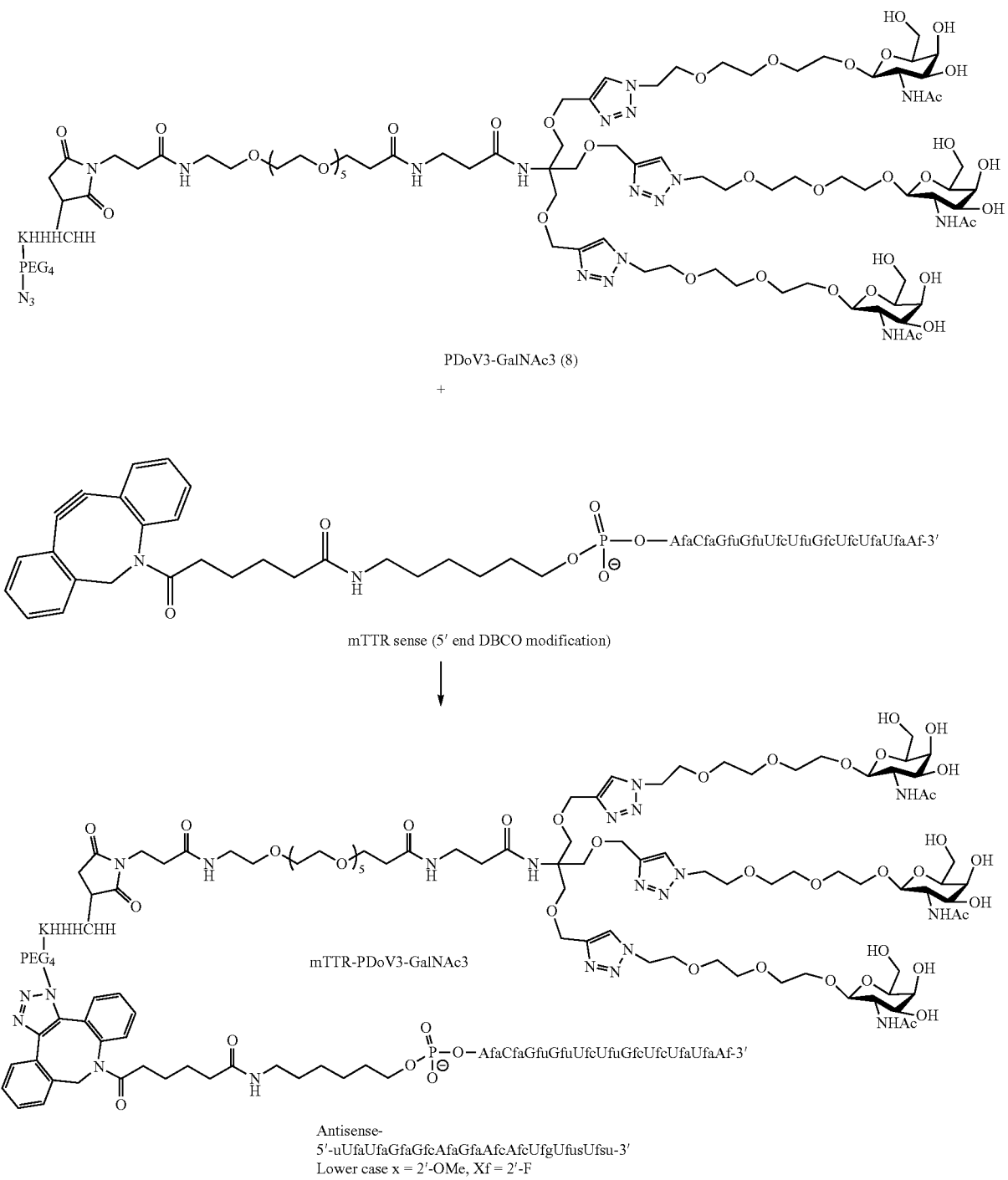

PDoV3-GalNAc3 (8)

+ mTTR sense (5′ end DBCO modification)

mTTR-PDoV3-GalNAc3

Antisense-
5′-uUfaUfaGfaGfcAfaGfaAfcAfcUfgUfusUfsu-3′
Lower case x = 2′-OMe, Xf = 2′-F PDoV3-GalNAc3 8 (996 µg, 0.317 µmol) in DMSO (99.6 µL) was added to a solution of mTTR1-sense-5′-DBCO (1.54 mg, 0.212 µmol) in RNAse free water (100 µL). The resultant mixture was stirred at 25° C. for 2 hours. After >85%. 1:1 annealing (95° C. for 5 min, cool down by around 1° C./min to room temperature, then store under −20° C.) with the antisense strand provided the final conjugate duplex mTTR1-PDoV3-GalNAc3.

Example 15

In Vitro Study of Conjugates of APOB100-PDoVn-GalNAc3

Alexa 647 labeled siRNA-GalNAc conjugates (ApoB100-PDoV1-GalNAc3-Alexa647, ApoB100-PDoV2-GalNAc3-Alexa647, ApoB100-PDoV2-GalNAc3-Alexa647) were used in the in vitro cell uptake experiment. Lipofectamine-delivered Alexa 647 labeled siRNA was used as a control. HepG2 cells and Huh7 cells with ASGPR overexpression were used to compare with the wild type cells in the transfection experiment. 5000 Cells were plated in a 96 well plate overnight. Cells were transfected with 50 nM siRNA for 2 h, 24, and 48 hours. Nuclei were stained with Hoechst dye and cells were imaged in Cytation imaging station in PBS. Images were taken at ×20 magnification. The data obtained showed that HepG2 cells overexpressing ASGPR showed much greater uptake of fluorescent labeled material than wild type HepG2 cells lacking overexpressed ASGPR.

Huh7 cells overexpressing ASGPR also showed an increased uptake compared with Huh7 cells not overexpressing ASGPR receptors but the labeling was not as intense as in wild type HepG2 cells.

PDOV1 and PDOV2 both demonstrated delivery of labeled siRNA to HepG2 cells overexpressing ASGPR but little or no labeling of wild type cells. In the absence of GalNac on the constructs we did not see any uptake into the ASGPR overexpressing cells.

In a subsequent experiment we examined delivery with PDOV1, 2 and 3 variations in Huh7 overexpressing ASGPR. PDoV2 and 3 showed some specificity of uptake into these cells compared with Wild type cells. PDoV1 also showed some delivery to these cells but was not as great as PDoV2 and PDoV3. PDoV2 showed significant uptake after 24 h exposure.

Example 16

In Vitro Study of mTTR-PDoVx-GalNAc in Primary Mouse Hepatocytes

Dose-response screens for GalNAc-conjugated siRNAs (mTTR1-PDoV3-GalNAc3, mTTR1-PDoV2-GalNAc3, mTTR2-GalNAc3 positive control, mTTR2-GalNAc3 positive control) were performed using primary mouse hepatocytes for target TTR. The cell density was 40000 cells/96 well. The concentration was from: highest at 1 µM in 5-fold dilutions to lowest at 3 µM. Cells were transfected by direct incubation for 72 hours. The data was read out by bDNA assay. The data was analyzed by XLfit software. TTR signal normalized to gapdh, mean of quadruplicates, mock-treated cells set=1, Xlfit for calculation of IC50 values. The primary hepatocytes used were purchased from Primacyt, Germany (lot MH181219), derived from CD 1 mice, and treated with siRNA right after thawing.

The two siRNAs were both conjugated to trivalent GalNAc clusters at the 3' end (mTTR2 siRNA sequence was a fully modified sequence and 4 more additional PS linkages modification on the oligonucleotides than mTTR1. (Nair, et al., *J. Am. Chem. Soc.* 136:16958-16961(2014). Aha1-GaNAc3 positive control was used as a standard control, targeted to the housekeeper ahsa1. This was used as both negative and positive control, hybridizing the cell lysates either to the screening target or to an ahsa1-specific probe. Table e1 lists the sequences of the 2 control siRNAs and the structure of the GalNAc cluster. Table e1. Control siRNA sequence and targets. (Images discloses SEQ ID NOS 36, 47-48, 59, and 47-48, respectively, in order of appearance)

TABLE e1

Control siRNA sequence and targets. (Images discloses SEQ ID NOS 36, 47-48, 59, and 47-48, respectively, in order of appearance)

| conjugates | target | sequence |
|---|---|---|
| mTTR2-GaNAc3 positive control | mouse TTR | Sense: 5'-AfsasCfaGfuGfuUfCfUfuGfcUfcUfaUfaAf(NHC6)(GalNAc3)-3' (SEQ ID NO: 39)<br>Antisense: 5'-usUfsaUfaGfaGfcAfagaAfcAfcUfgUfususu-3' (SEQ ID NO: 40) |
| Aha1-GaNAc3 positive control | AHSA1 | Sense: 5'-uscsUfcGfuGfgCfcUfuAfaUfgAfaAf(NHC6)(GalNAc3)-3' (SEQ ID NO: 41)<br>Antisense: 5'-UfsUfsuCfaUfuAfaGfgCfcAfcGfaGfasusu-3' (SEQ ID NO: 42) |
| Trivalent GalNAc3 ligand on the control conjugate | | 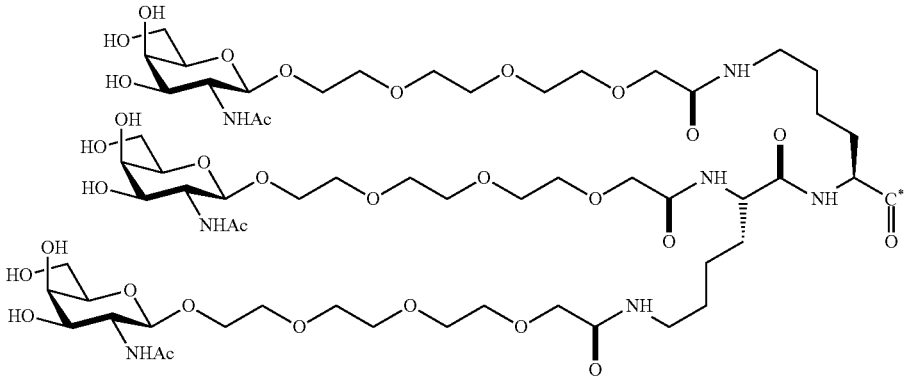 |

TABLE e1-continued

Control siRNA sequence and targets. (Images discloses SEQ ID NOS 36, 47-48, 59, and 47-48, respectively, in order of appearance)

| conjugates | target | sequence |
|---|---|---|

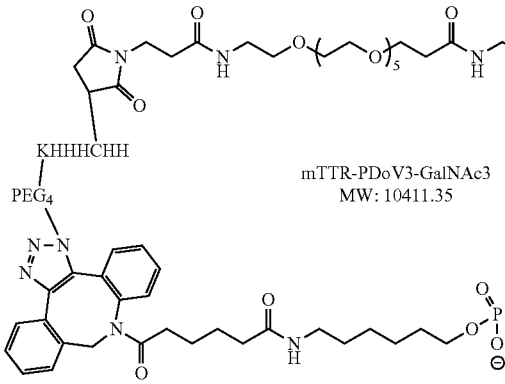

mTTR-PDoV3-GalNAc3
MW: 10411.35 mTTR sense (5' end DBCO modification)
Antisense - 5'-uUfaUfaGfaGfcAfaGfaAfcAfcUfgUfusUfsu-3'
Lower case x = 2'-OMe, Xf = 2'-F

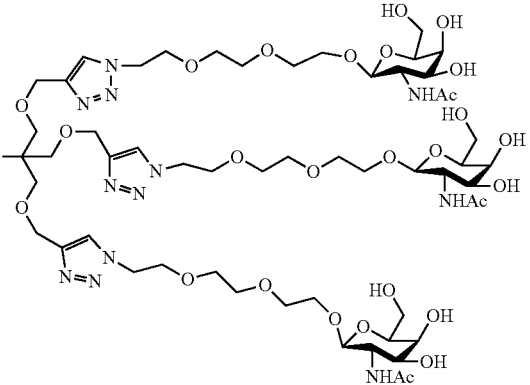

mTTR-PDoV3-GalNAc3 mTTR sense (5' end DBCO modification)
Antisense - 5'-uUfaUfaGfaGfcAfaGfaAfcAfcUfgUfusUfsu-3'
Lower case x = 2'-OMe, Xf = 2'-F TABLE e2

Dose-response summary for GalNAc-conjugated siRNAs in vitro screening.

| Compound | IC$_{50}$ (μM) | IC$_{80}$ (μM) | Max. KD (%) |
|---|---|---|---|
| mTTR1-PDoV3-GalNAc3 | 0.0018 | 0.0048 | 97% |
| mTTR1-PDoV2-GalNAc3 | 0.0026 | 0.0071 | 97% |
| mTTR2-GalNAc3 positive control | 0.0001 | 0.0003 | 96% |
| aha1-GalNAc3 positive control | 0.0015 | 0.0059 | 96% |

Figure 15A:
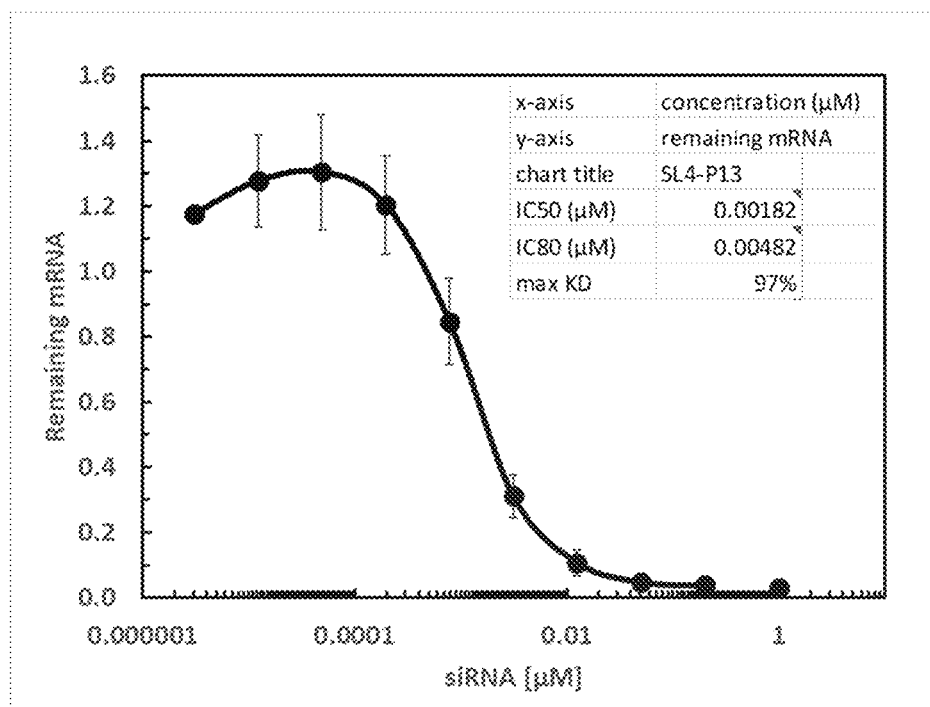
FIG. 15A shows in vitro serial dilution data for the conjugate of mTTR1-PDoV3-GalNAc3.
Figure 15B:
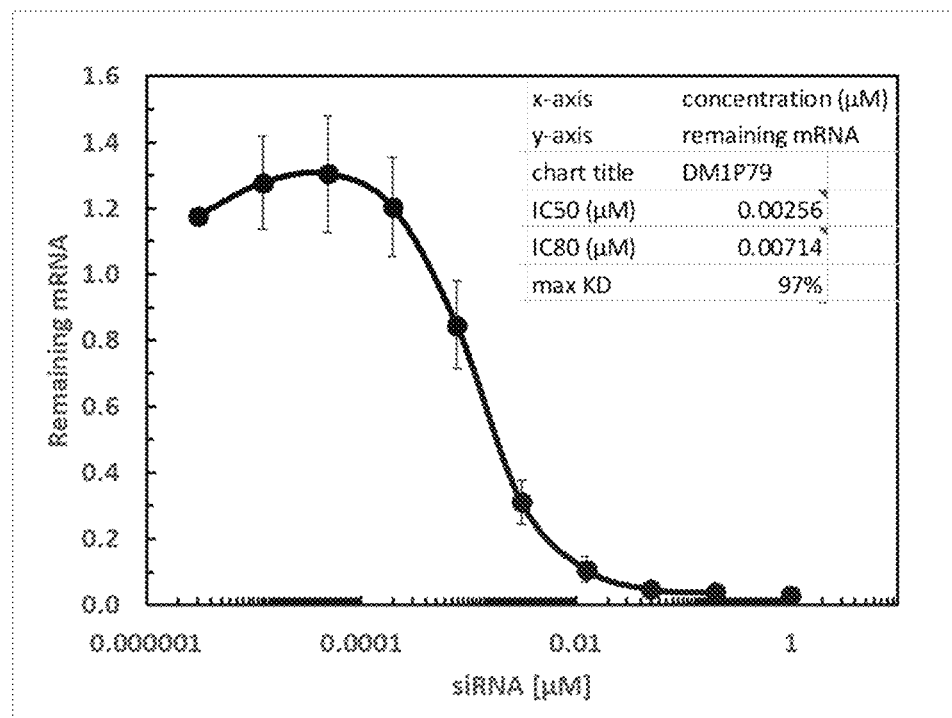
FIG. 15B shows in vitro serial dilution data for the mTTR1-PDoV2-GalNAc3 conjugate.
Figure 15C:
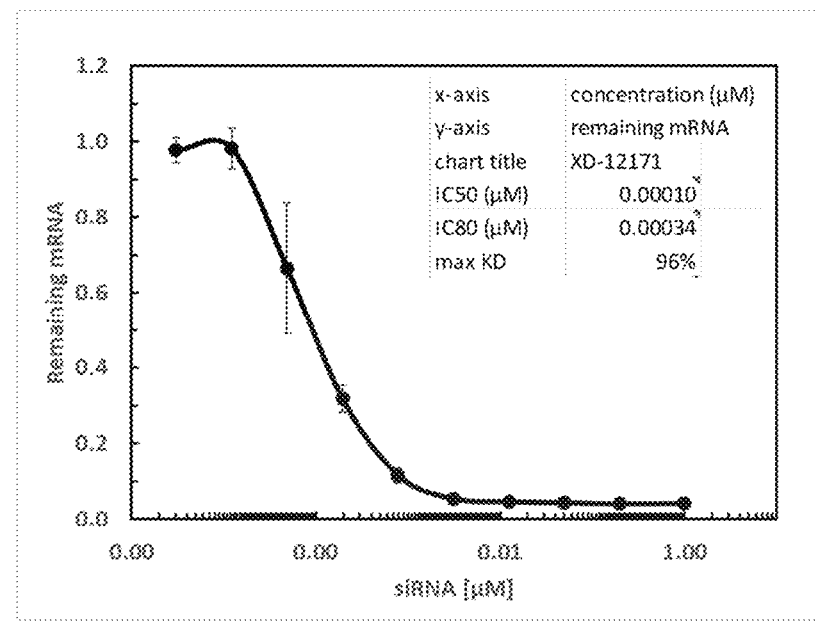
FIG. 15C shows serial dilution data for the mTTR2-GalNAc3 positive control conjugate.
Figure 15D:
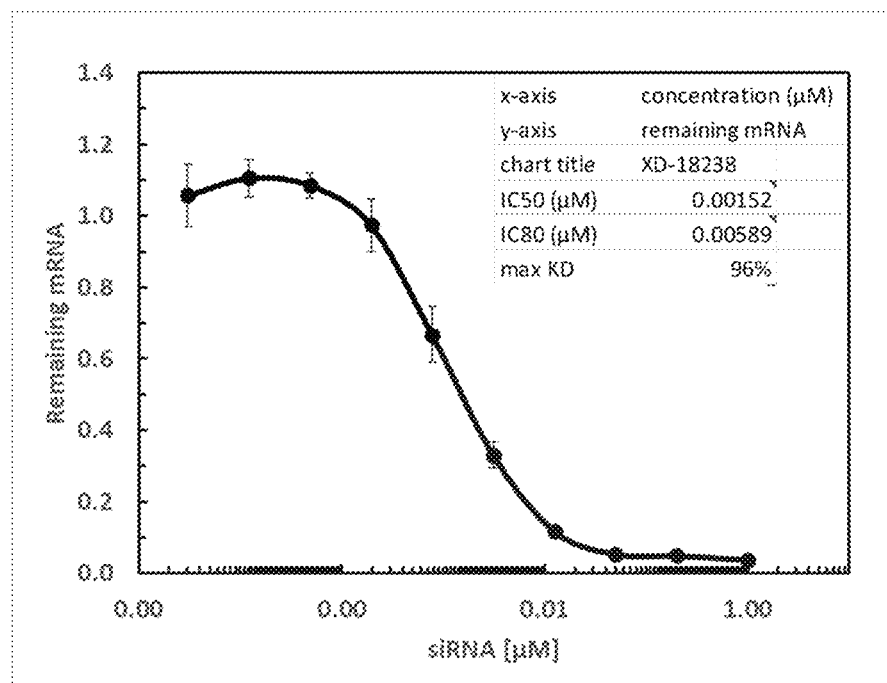
FIG. 15D shows in vitro serial dilution data for the Aha1-GalNAc3 positive control conjugate.

Conjugate of mTTR1-PDoV3-GalNAc3 in vitro serious dilution data—see FIG. 15A: the IC$_{50}$=1.82 nM is comparable with the literature report of IC$_{50}$=1.39 nM for the same siRNA sequence 21 and chemical modification on the oligonucleotides (Nair et al., supra.) FIG. 15B shows in vitro, serial dilution data for the mTTR1-PDoV2-GalNAc3 conjugate. FIG. 15C shows serial dilution data for the mTTR2-GalNAc3 positive control conjugate in vitro serial dilution data: mTTR2 siRNA sequence is a fully modified sequence and has 4 more additional PS linkages modification on the oligonucleotides (Nair, supra.) FIG. 15D shows in vitro serial dilution data for the Aha1-GalNAc3 positive control conjugate.

All publications identified herein, including issued patents and published patent applications, and all database entries identified by url addresses or accession numbers are incorporated herein by reference in their entireties.

Although this invention has been described in relation to certain embodiments thereof, and many details have been set forth for purposes of illustration, it will be apparent to those

The invention claimed is:

1. A chemical construct comprising a peptide construct covalently linked to: (a) a targeting ligand; and (b) a first therapeutic oligonucleotide; and, optionally (c) a second therapeutic oligonucleotide that may be the same or different than the first,
wherein the amino acid sequence of said peptide construct is selected from the group consisting of: KHHHCKH (SEQ ID NO: 3); HKHHHCKH (SEQ ID NO: 4); HHKHHHCKH (SEQ ID NO: 5); HHHKHHHKCHHHKHHH (SEQ ID NO: 6); HHHKHHCKHHH (SEQ ID NO: 7); HHHKHHCRHHH (SEQ ID NO: 8); HKHHCKH (SEQ ID NO: 9); HKHCH (SEQ ID NO: 10); HKHCKH (SEQ ID NO: 11); HKHC (SEQ ID NO: 12); HHHK(S)HHCKHHH (SEQ ID NO: 13); and HHHK(S)HHKCHH(S)HHH (SEQ ID NO: 14),
wherein the targeting ligand is linked to the side chain of the cysteine residue and the first oligonucleotide is linked to the side chain of a lysine residue, and wherein (S) is

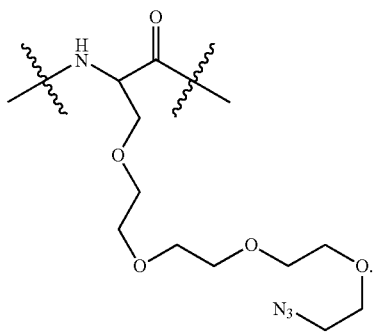 [SMILES: *NC(COCCOCCOCCOCCN=[N+]=[N-])C(*)=O]

2. The construct of claim 1, wherein the targeting ligand binds to the asialoglycoprotein receptor.

3. The construct of claim 1, wherein the targeting ligand is linked to the peptide via linker-1, wherein linker-1 comprises one of the following structures:

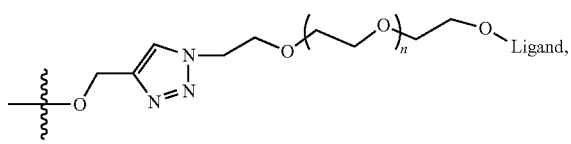

wherein n is 1, 2, or 3 and is connected to the bridge through a 1, 5-triazol ring with an OCH$_2$ unit; or

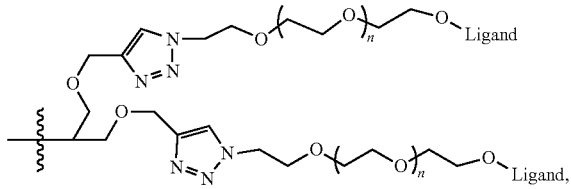

wherein n is 1, 2, or 3 and is connected to the bridge through a 1, 5-triazol ring with a CH$_2$OCH$_2$ unit; or

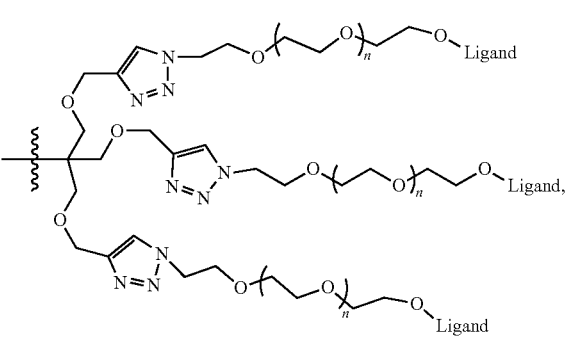

wherein n is 1, 2, or 3 and is connected to the bridge through a 1, 5-triazol ring with a CH$_2$OCH$_2$ unit.

4. The construct of claim 1, wherein the oligonucleotide is linked to the peptide via Linker 2, wherein Linker 2 comprises an aliphatic chain, a polyethylene glycol chain, a hydrophobic lipid chain or a hydrophilic chain.

5. The construct of claim 4, wherein Linker 2 is covalently linked to the oligonucleotide via a reactive moiety Group 2, wherein:

Linker 2 =

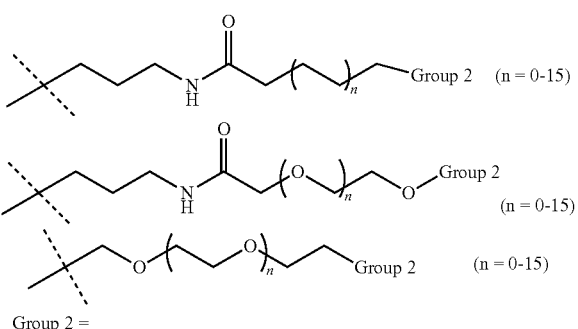

6. The construct of claim 1, wherein the oligonucleotide is an siRNA molecule comprising a duplex of two complimentary, single-stranded oligonucleotides each with a length between 10-29 bases or 19-27 bases.

7. The construct of claim 1, wherein the oligonucleotide comprises either deoxyribonucleotides or ribonucleotides.

8. The construct of claim 5, wherein the oligonucleotide is further chemically modified at the 5' or 3' position with a Linker 3, wherein Linker 3 contains a complimentary conjugation site group 3 which covalently reacts with the linker 2 to link the ligand-peptide conjugate and the nucleotides.

9. The construct of claim 8, comprising a structure as shown below:

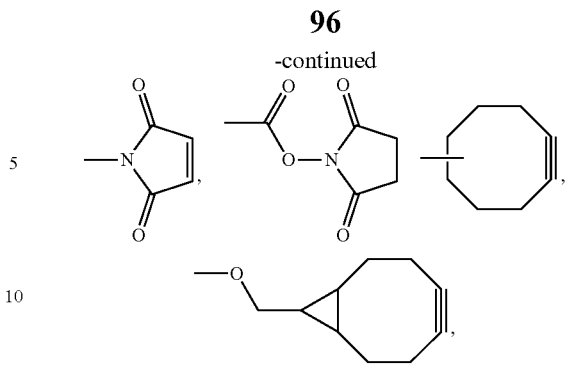

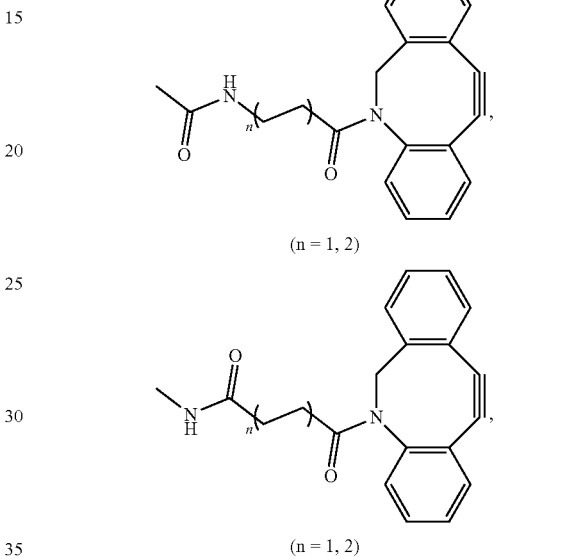

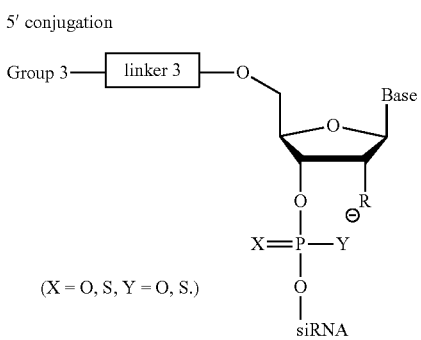

-continued

3' conjugation

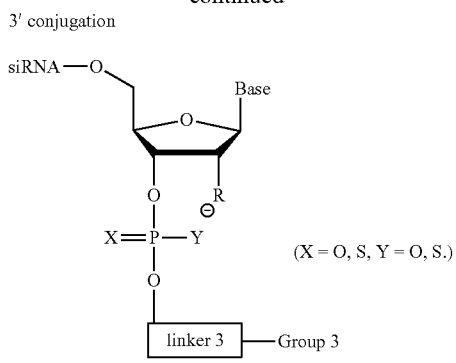

(X = O, S, Y = O, S.)

10. The construct of claim 2, wherein the targeting ligand is selected from the group consisting of N-acetyl-galactosamine (GalNAc), galactose, galactosamine, N-formal-galactosoamine, N-propionyl-galactosamine, and N-butanoylgalactosamine.

11. The construct of claim 1, wherein the targeting ligand is folic acid or is a peptide selected from the group consisting of cyclic RGD, APRPG (SEQ ID NO: 15), NGR, F3 peptide, CGKRK (SEQ ID NO: 16), LyP-1, iRGD (CRGDRCPDC (SEQ ID NO: 17)), iNGR, T7 peptide (HAIYPRH (SEQ ID NO: 18)), MMP2-cleavable octapeptide (GPLGIAGQ (SEQ ID NO: 19)), CP15 (VHLGYAT (SEQ ID NO: 20)), FSH (FSH-β, 33-53 amino acids, YTRDLVKDPARPKIQKTCTF (SEQ ID NO: 21)), LHRH (QHTSYkcLRP (SEQ ID NO: 22)), gastrin-releasing peptides (GRPs) (CGGNHWAVGHLM (SEQ ID NO: 23)), RVG (YTWMPENPRPGTPCDIFTNSRGKRASNG (SEQ ID NO: 24)), FMDV20 peptide sequence (NAVPNLRGDLQVLAQKVART (SEQ ID NO: 25)), and GLP.

12. The chemical construct of claim 1, wherein the oligonucleotide is selected from the group consisting of an siRNA, an antisense oligonucleotide, an miRNA, an saRNA, an shRNA an aptamer, an RNAzyme, an DNAzyme, a decoy oligonucleotide, and a CpG motif.

13. A method for treating cancer in a mammal, comprising administering to the mammal a therapeutically effective amount of the construct of claim 1.

* * * * *

```
                              SEQUENCE LISTING

<160> NUMBER OF SEQ ID NOS: 60

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

His His His His
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

His His His Lys
1

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys His His His Cys Lys His
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

His Lys His His His Cys Lys His
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

His His Lys His His His Cys Lys His
1               5

<210> SEQ ID NO 6
<211> LENGTH: 16
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 6

His His His Lys His His His Lys Cys His His His Lys His His His
1               5                   10                  15

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

His His His Lys His His Cys Lys His His His
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

His His His Lys His His Cys Arg His His His
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

His Lys His His Cys Lys His
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

His Lys His Cys His
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

His Lys His Cys Lys His
1               5

```
<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

His Lys His Cys
1

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ser([(CH2)O]3(CH2)2N3)

<400> SEQUENCE: 13

His His His Lys Ser His His Cys Lys His His His
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ser([(CH2)O]3(CH2)2N3)
<220> FEATURE:
<221> NAME/KEY: MOD_RES
<222> LOCATION: (11)..(11)
<223> OTHER INFORMATION: Ser([(CH2)O]3(CH2)2N3)

<400> SEQUENCE: 14

His His Lys Ser His His Lys Cys His His Ser His His His
1               5                   10

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Pro Arg Pro Gly
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16
```

Cys Gly Lys Arg Lys
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Cys Arg Gly Asp Arg Cys Pro Asp Cys
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

His Ala Ile Tyr Pro Arg His
1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Pro Leu Gly Ile Ala Gly Gln
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Val His Leu Gly Tyr Ala Thr
1               5

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Tyr Thr Arg Asp Leu Val Lys Asp Pro Ala Arg Pro Lys Ile Gln Lys
1               5                   10                  15

Thr Cys Thr Phe
            20

<210> SEQ ID NO 22

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(7)
<223> OTHER INFORMATION: D-amino acid

<400> SEQUENCE: 22

Gln His Thr Ser Tyr Lys Cys Leu Arg Pro
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Cys Gly Gly Asn His Trp Ala Val Gly His Leu Met
1               5                   10

<210> SEQ ID NO 24
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Tyr Thr Trp Met Pro Glu Asn Pro Arg Pro Gly Thr Pro Cys Asp Ile
1               5                   10                  15

Phe Thr Asn Ser Arg Gly Lys Arg Ala Ser Asn Gly
            20                  25

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asn Ala Val Pro Asn Leu Arg Gly Asp Leu Gln Val Leu Ala Gln Lys
1               5                   10                  15

Val Ala Arg Thr
            20

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Lys His His His
1
```

```
<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

His His His His Lys
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Lys His His His His
1               5

<210> SEQ ID NO 29
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(33)
<223> OTHER INFORMATION: This region may encompass 1-8 "His His His Lys"
      repeating units

<400> SEQUENCE: 29

Lys His His His Lys His His His Lys His His His Lys His His His
1               5                   10                  15

Lys His His His Lys His His His Lys His His His Lys His His His
                20                  25                  30

Lys

<210> SEQ ID NO 30
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(21)
<223> OTHER INFORMATION: This region may encompass 1-4 "His His His His
      Lys" repeating units
<220> FEATURE:
<221> NAME/KEY: SITE
<222> LOCATION: (22)..(53)
<223> OTHER INFORMATION: This region may encompass 1-8 "His His His Lys"
      repeating units

<400> SEQUENCE: 30

Lys His His His His Lys His His His His Lys His His His His Lys
1               5                   10                  15

His His His His Lys His His His Lys His His His Lys His His His
                20                  25                  30

Lys His His His Lys His His His Lys His His His Lys His His His
```

```
                 35                  40                  45
Lys His His His Lys
         50

<210> SEQ ID NO 31
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(21)
<223> OTHER INFORMATION: This region may encompass 1-4 "His His His His
      Lys" repeating units
<220> FEATURE:
<221> NAME/KEY: SITE
<222> LOCATION: (22)..(53)
<223> OTHER INFORMATION: This region may encompass 1-8 "His His His Lys"
      repeating units

<400> SEQUENCE: 31

Lys His His His His Lys His His His His Lys His His His His Lys
1               5                   10                  15

His His His His Lys His His His His Lys His His His His Lys His His
                20                  25                  30

Lys His His His Lys His His His Lys His His His Lys His His His
         35                  40                  45

Lys His His His Lys
         50

<210> SEQ ID NO 32
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 32

Lys His His His His Lys His His His Lys His His His Lys His His
1               5                   10                  15

His Lys

<210> SEQ ID NO 33
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 33

Lys His His His His Lys His His His Lys His His His Lys His His
1               5                   10                  15

His Lys

<210> SEQ ID NO 34
<211> LENGTH: 209
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(10)
<223> OTHER INFORMATION: This region may encompass 1-10 repeating
      residues
<220> FEATURE:
<221> NAME/KEY: SITE
<222> LOCATION: (11)..(20)
<223> OTHER INFORMATION: This region may encompass 1-10 repeating
      residues
<220> FEATURE:
<221> NAME/KEY: SITE
<222> LOCATION: (21)..(30)
<223> OTHER INFORMATION: This region may encompass 1-10 repeating
      residues
<220> FEATURE:
<221> NAME/KEY: SITE
<222> LOCATION: (31)..(40)
<223> OTHER INFORMATION: This region may encompass 1-10 repeating
      residues
<220> FEATURE:
<221> NAME/KEY: SITE
<222> LOCATION: (41)..(50)
<223> OTHER INFORMATION: This region may encompass 1-10 repeating
      residues
<220> FEATURE:
<221> NAME/KEY: SITE
<222> LOCATION: (51)..(60)
<223> OTHER INFORMATION: This region may encompass 1-10 repeating
      residues
<220> FEATURE:
<221> NAME/KEY: SITE
<222> LOCATION: (61)..(70)
<223> OTHER INFORMATION: This region may encompass 1-10 repeating
      residues
<220> FEATURE:
<221> NAME/KEY: SITE
<222> LOCATION: (71)..(80)
<223> OTHER INFORMATION: This region may encompass 1-10 repeating
      residues
<220> FEATURE:
<221> NAME/KEY: SITE
<222> LOCATION: (81)..(90)
<223> OTHER INFORMATION: This region may encompass 1-10 repeating
      residues
<220> FEATURE:
<221> NAME/KEY: SITE
<222> LOCATION: (91)..(100)
<223> OTHER INFORMATION: This region may encompass 1-10 repeating
      residues
<220> FEATURE:
<221> NAME/KEY: SITE
<222> LOCATION: (101)..(110)
<223> OTHER INFORMATION: This region may encompass 1-10 repeating
      residues
<220> FEATURE:
<221> NAME/KEY: SITE
<222> LOCATION: (111)..(120)
<223> OTHER INFORMATION: This region may encompass 1-10 repeating
      residues
<220> FEATURE:
<221> NAME/KEY: SITE
<222> LOCATION: (121)..(130)
<223> OTHER INFORMATION: This region may encompass 1-10 repeating
      residues
<220> FEATURE:
<221> NAME/KEY: SITE
<222> LOCATION: (131)..(140)
<223> OTHER INFORMATION: This region may encompass 1-10 repeating
      residues
<220> FEATURE:
<221> NAME/KEY: SITE
<222> LOCATION: (141)..(150)
<223> OTHER INFORMATION: This region may encompass 1-10 repeating
```

```
                                  -continued
      residues
<220> FEATURE:
<221> NAME/KEY: SITE
<222> LOCATION: (151)..(160)
<223> OTHER INFORMATION: This region may encompass 1-10 repeating
      residues
<220> FEATURE:
<221> NAME/KEY: SITE
<222> LOCATION: (161)..(170)
<223> OTHER INFORMATION: This region may encompass 1-10 repeating
      residues
<220> FEATURE:
<221> NAME/KEY: SITE
<222> LOCATION: (171)..(180)
<223> OTHER INFORMATION: This region may encompass 1-10 repeating
      residues
<220> FEATURE:
<221> NAME/KEY: SITE
<222> LOCATION: (181)..(190)
<223> OTHER INFORMATION: This region may encompass 1-10 repeating
      residues
<220> FEATURE:
<221> NAME/KEY: SITE
<222> LOCATION: (191)..(200)
<223> OTHER INFORMATION: This region may encompass 1-10 repeating
      residues
<220> FEATURE:
<221> NAME/KEY: SITE
<222> LOCATION: (1)..(200)
<223> OTHER INFORMATION: This region may encompass 1-10 "(H)n(K)m"
      units, wherein n = 1-10 and m = 1-10
<220> FEATURE:
<221> NAME/KEY: SITE
<222> LOCATION: (201)..(205)
<223> OTHER INFORMATION: This region may encompass 1-5 repeating
      residues or be absent in its entirety
<220> FEATURE:
<221> NAME/KEY: MOD_RES
<222> LOCATION: (201)..(209)
<223> OTHER INFORMATION: Any amino acid or absent
<220> FEATURE:
<221> NAME/KEY: SITE
<222> LOCATION: (206)..(209)
<223> OTHER INFORMATION: This region may encompass 1-4 repeating
      residues or be absent in its entirety
<220> FEATURE:
<223> OTHER INFORMATION: See specification as filed for detailed
      description of substitutions and preferred embodiments

<400> SEQUENCE: 34

His His His His His His His His His Lys Lys Lys Lys Lys Lys
1               5                   10                  15

Lys Lys Lys Lys His His His His His His His His Lys Lys
            20                  25                  30

Lys Lys Lys Lys Lys Lys Lys Lys His His His His His His His
        35                  40                  45

His His Lys Lys Lys Lys Lys Lys Lys Lys Lys His His His His
    50                  55                  60

His His His His His His Lys Lys Lys Lys Lys Lys Lys Lys Lys
65                  70                  75                  80

His His His His His His His His Lys Lys Lys Lys Lys
                85                  90                  95

Lys Lys Lys Lys His His His His His His His His Lys Lys
            100                 105                 110

Lys Lys Lys Lys Lys Lys Lys His His His His His His
        115                 120                 125

His His Lys Lys Lys Lys Lys Lys Lys Lys His His His His
    130                 135                 140

His His His His His His Lys Lys Lys Lys Lys Lys Lys Lys Lys
```

```
            145                 150                 155                 160
His His His His His His His His His His Lys Lys Lys Lys Lys Lys
                    165                 170                 175

Lys Lys Lys Lys His His His His His His His His His His Lys Lys
        180                 185                 190

Lys Lys Lys Lys Lys Lys Lys Xaa Xaa Xaa Xaa Xaa Xaa Xaa
        195                 200                 205

Xaa

<210> SEQ ID NO 35
<211> LENGTH: 210
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(10)
<223> OTHER INFORMATION: This region may encompass 1-10 repeating
      residues
<220> FEATURE:
<221> NAME/KEY: SITE
<222> LOCATION: (11)..(20)
<223> OTHER INFORMATION: This region may encompass 1-10 repeating
      residues
<220> FEATURE:
<221> NAME/KEY: SITE
<222> LOCATION: (21)..(30)
<223> OTHER INFORMATION: This region may encompass 1-10 repeating
      residues
<220> FEATURE:
<221> NAME/KEY: SITE
<222> LOCATION: (31)..(40)
<223> OTHER INFORMATION: This region may encompass 1-10 repeating
      residues
<220> FEATURE:
<221> NAME/KEY: SITE
<222> LOCATION: (41)..(50)
<223> OTHER INFORMATION: This region may encompass 1-10 repeating
      residues
<220> FEATURE:
<221> NAME/KEY: SITE
<222> LOCATION: (51)..(60)
<223> OTHER INFORMATION: This region may encompass 1-10 repeating
      residues
<220> FEATURE:
<221> NAME/KEY: SITE
<222> LOCATION: (61)..(70)
<223> OTHER INFORMATION: This region may encompass 1-10 repeating
      residues
<220> FEATURE:
<221> NAME/KEY: SITE
<222> LOCATION: (71)..(80)
<223> OTHER INFORMATION: This region may encompass 1-10 repeating
      residues
<220> FEATURE:
<221> NAME/KEY: SITE
<222> LOCATION: (81)..(90)
<223> OTHER INFORMATION: This region may encompass 1-10 repeating
      residues
<220> FEATURE:
<221> NAME/KEY: SITE
<222> LOCATION: (91)..(100)
<223> OTHER INFORMATION: This region may encompass 1-10 repeating
      residues
<220> FEATURE:
<221> NAME/KEY: SITE
<222> LOCATION: (101)..(110)
<223> OTHER INFORMATION: This region may encompass 1-10 repeating
      residues
<220> FEATURE:
<221> NAME/KEY: SITE
<222> LOCATION: (111)..(120)
```

```
<223> OTHER INFORMATION: This region may encompass 1-10 repeating
      residues
<220> FEATURE:
<221> NAME/KEY: SITE
<222> LOCATION: (121)..(130)
<223> OTHER INFORMATION: This region may encompass 1-10 repeating
      residues
<220> FEATURE:
<221> NAME/KEY: SITE
<222> LOCATION: (131)..(140)
<223> OTHER INFORMATION: This region may encompass 1-10 repeating
      residues
<220> FEATURE:
<221> NAME/KEY: SITE
<222> LOCATION: (141)..(150)
<223> OTHER INFORMATION: This region may encompass 1-10 repeating
      residues
<220> FEATURE:
<221> NAME/KEY: SITE
<222> LOCATION: (151)..(160)
<223> OTHER INFORMATION: This region may encompass 1-10 repeating
      residues
<220> FEATURE:
<221> NAME/KEY: SITE
<222> LOCATION: (161)..(170)
<223> OTHER INFORMATION: This region may encompass 1-10 repeating
      residues
<220> FEATURE:
<221> NAME/KEY: SITE
<222> LOCATION: (171)..(180)
<223> OTHER INFORMATION: This region may encompass 1-10 repeating
      residues
<220> FEATURE:
<221> NAME/KEY: SITE
<222> LOCATION: (181)..(190)
<223> OTHER INFORMATION: This region may encompass 1-10 repeating
      residues
<220> FEATURE:
<221> NAME/KEY: SITE
<222> LOCATION: (191)..(200)
<223> OTHER INFORMATION: This region may encompass 1-10 repeating
      residues
<220> FEATURE:
<221> NAME/KEY: SITE
<222> LOCATION: (1)..(200)
<223> OTHER INFORMATION: This region may encompass 1-10 "(H)n(K)m"
      units, wherein n = 1-10 and m = 1-10
<220> FEATURE:
<221> NAME/KEY: SITE
<222> LOCATION: (201)..(205)
<223> OTHER INFORMATION: This region may encompass 1-5 repeating
      residues or be absent in its entirety
<220> FEATURE:
<221> NAME/KEY: MOD_RES
<222> LOCATION: (201)..(210)
<223> OTHER INFORMATION: Any amino acid or absent
<220> FEATURE:
<221> NAME/KEY: SITE
<222> LOCATION: (206)..(210)
<223> OTHER INFORMATION: This region may encompass 1-5 repeating
      residues or be absent in its entirety
<220> FEATURE:
<223> OTHER INFORMATION: See specification as filed for detailed
      description of substitutions and preferred embodiments

<400> SEQUENCE: 35

His His His His His His His His His Lys Lys Lys Lys Lys Lys
1               5                   10                  15

Lys Lys Lys Lys His His His His His His His His His Lys Lys
            20                  25                  30

Lys Lys Lys Lys Lys Lys Lys Lys His His His His His His His
        35                  40                  45

His His Lys Lys Lys Lys Lys Lys Lys Lys Lys His His His His
    50                  55                  60
```

His His His His His His Lys Lys Lys Lys Lys Lys Lys Lys Lys Lys
65                  70                  75                  80

His His His His His His His His His His Lys Lys Lys Lys Lys Lys
                85                  90                  95

Lys Lys Lys Lys His His His His His His His His His His Lys Lys
            100                 105                 110

Lys Lys Lys Lys Lys Lys Lys His His His His His His His His His
            115                 120                 125

His His Lys Lys Lys Lys Lys Lys Lys Lys Lys His His His His His
    130                 135                 140

His His His His His Lys Lys Lys Lys Lys Lys Lys Lys Lys Lys Lys
145                 150                 155                 160

His His His His His His His His Lys Lys Lys Lys Lys Lys Lys Lys
                165                 170                 175

Lys Lys Lys Lys His His His His His His His His His His Lys Lys
            180                 185                 190

Lys Lys Lys Lys Lys Lys Lys Xaa Xaa Xaa Xaa Xaa Xaa Xaa Xaa
            195                 200                 205

Xaa Xaa
    210

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(PEG4-N3)

<400> SEQUENCE: 36

Lys His His His Cys His His
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(PEG4-N3)

<400> SEQUENCE: 37

Lys Ser Ser Ser Cys Ser Ser
1               5

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 38

```
uuugtaaucg ucgauacccu gcucg                                        25
```

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39

```
aacaguguuc uugcucuaua a                                            21
```

<210> SEQ ID NO 40
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40

```
uuauagagca agaacacugu uuu                                          23
```

<210> SEQ ID NO 41
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41

```
ucucguggcc uuaaugaaa                                               19
```

<210> SEQ ID NO 42
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42

```
uuucauuaag gccacgagau u                                            21
```

<210> SEQ ID NO 43
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43

```
ggaaucuuau auuugaucca a                                            21
```

<210> SEQ ID NO 44
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
uuggaucaaa uauaagauuc ccu 23

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
ggaaucuuau auuugaucca a 21

<210> SEQ ID NO 46
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
uuggaucaaa uauaagauuc ccu 23

<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
aacaguguuc uugcucuaua a 21

<210> SEQ ID NO 48
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
uuauagagca agaacacugu uuu 23

<210> SEQ ID NO 49
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
aacaguguuc uugcucuaua a 21

<210> SEQ ID NO 50
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
uuauagagca agaacacugu uuu 23

```
<210> SEQ ID NO 51
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
cgagcagggu aucgacgauu acaaa                                           25

<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
caggguaucg acgauuacaa a                                               21

<210> SEQ ID NO 53
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
uuuguaaucg ucgauacccu g                                               21

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: modified Lys
<220> FEATURE:
<221> NAME/KEY: MOD_RES
<222> LOCATION: (5)..(5)
<223> OTHER INFORMATION: modified Cys
<220> FEATURE:
<221> NAME/KEY: MOD_RES
<222> LOCATION: (9)..(9)
<223> OTHER INFORMATION: modified Cys
<220> FEATURE:
<221> NAME/KEY: MOD_RES
<222> LOCATION: (12)..(12)
<223> OTHER INFORMATION: modified Cys
<220> FEATURE:
<221> NAME/KEY: MOD_RES
<222> LOCATION: (13)..(13)
<223> OTHER INFORMATION: modified Lys
<220> FEATURE:
<223> OTHER INFORMATION: See specification as filed for detailed
      description of substitutions and preferred embodiments

<400> SEQUENCE: 54

His His His Lys Cys His His Lys Cys His His Cys Lys His His His
1               5                   10                  15

<210> SEQ ID NO 55
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Lys(PEG4-N3)

<400> SEQUENCE: 55

His His His Lys His His His Cys Lys His His His
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Lys(PEG4-N3)

<400> SEQUENCE: 56

His His His Lys His His His Cys His His His
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Lys(PEG4-N3)

<400> SEQUENCE: 57

His His His Lys His His His Cys Arg His His His
1               5                   10

<210> SEQ ID NO 58
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: modified Lys
<220> FEATURE:
<221> NAME/KEY: MOD_RES
<222> LOCATION: (9)..(9)
<223> OTHER INFORMATION: modified Cys
```

```
<220> FEATURE:
<221> NAME/KEY: MOD_RES
<222> LOCATION: (13)..(13)
<223> OTHER INFORMATION: modified Lys
<220> FEATURE:
<223> OTHER INFORMATION: See specification as filed for detailed
      description of substitutions and preferred embodiments

<400> SEQUENCE: 58

His His His Lys His His His Lys Cys His His Lys His His His
1               5                  10              15

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Lys(PEG4-N3)

<400> SEQUENCE: 59

His His His Lys His His Cys Arg His His His
1               5                  10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Lys(PEG4-N3)

<400> SEQUENCE: 60

His His His Lys His His Cys Lys His His His
1               5                  10
```